United States Patent
Berglund et al.

(10) Patent No.: US 11,135,283 B2
(45) Date of Patent: Oct. 5, 2021

(54) RETROVIRAL VECTOR FOR THE ADMINISTRATION AND EXPRESSION OF REPLICON RNA EXPRESSING HETEROLOGOUS NUCLEIC ACIDS

(71) Applicant: IMMUNE DESIGN CORP., Seattle, WA (US)

(72) Inventors: Peter Lars Aksel Berglund, Seattle, WA (US); Jacob Freeman Archer, Seattle, WA (US); Tsai-Yu Lin, Seattle, WA (US)

(73) Assignee: Immune Design Corp., Seattle, WA (US)

( * ) Notice: Subject to any disclaimer, the term of this patent is extended or adjusted under 35 U.S.C. 154(b) by 534 days.

(21) Appl. No.: 15/774,465

(22) PCT Filed: Nov. 9, 2016

(86) PCT No.: PCT/US2016/061092
§ 371 (c)(1),
(2) Date: May 8, 2018

(87) PCT Pub. No.: WO2017/083356
PCT Pub. Date: May 18, 2017

(65) Prior Publication Data
US 2020/0254087 A1 Aug. 13, 2020

Related U.S. Application Data

(60) Provisional application No. 62/252,865, filed on Nov. 9, 2015.

(51) Int. Cl.
*C12N 15/00* (2006.01)
*C12N 15/86* (2006.01)
*A61K 39/21* (2006.01)

(52) U.S. Cl.
CPC .............. *A61K 39/21* (2013.01); *C12N 15/86* (2013.01); *C12N 2740/15034* (2013.01); *C12N 2740/15043* (2013.01)

(58) Field of Classification Search
None
See application file for complete search history.

(56) References Cited

U.S. PATENT DOCUMENTS 4,569,794 A 2/1986 Smith et al.
4,703,004 A 10/1987 Hopp et al.
(Continued)

FOREIGN PATENT DOCUMENTS

GB 2220211 A 1/1990
WO 90/14837 A1 12/1990
(Continued)

OTHER PUBLICATIONS

Philpott et al., Use of nonintegrating lentiviral vectors for gene therapy, Human Gene. Therapy, 18:483-9 (2007).
(Continued)

*Primary Examiner* — M Franco G Salvoza
(74) *Attorney, Agent, or Firm* — Andrew W. Custer; Anna L. Cocuzzo

(57) ABSTRACT

The present disclosure relates generally to gene delivery using a chimeric, retroviral-RNA replicon vector particle for increased expression of transgenes in a host cell. In particular, the chimeric vectors described herein can be used in any of a variety of settings including gene therapy and vaccine settings.

20 Claims, 12 Drawing Sheets

Specification includes a Sequence Listing.

(56) References Cited

U.S. PATENT DOCUMENTS

| | | | |
|---|---|---|---|
| 4,886,499 | A | 12/1989 | Cirelli et al. |
| 4,937,190 | A | 6/1990 | Palmenberg et al. |
| 5,057,540 | A | 10/1991 | Kensil et al. |
| 5,168,062 | A | 12/1992 | Stinski |
| 5,279,552 | A | 1/1994 | Magnet |
| 5,328,483 | A | 7/1994 | Jacoby |
| 5,385,839 | A | 1/1995 | Stinski |
| 5,510,474 | A | 4/1996 | Quail et al. |
| 5,848,991 | A | 12/1998 | Gross et al. |
| 5,997,501 | A | 12/1999 | Gross et al. |
| 6,218,181 | B1 | 4/2001 | Verma et al. |
| 6,494,865 | B1 | 12/2002 | Alchas |
| 6,569,143 | B2 | 5/2003 | Alchas et al. |
| 6,670,349 | B1 | 12/2003 | Nyce |
| 6,689,118 | B2 | 2/2004 | Alchas et al. |
| 6,776,776 | B2 | 8/2004 | Alchas et al. |
| 6,780,171 | B2 | 8/2004 | Gabel et al. |
| 6,808,506 | B2 | 10/2004 | Lastovich et al. |
| 6,971,999 | B2 | 12/2005 | Py et al. |
| 7,047,070 | B2 | 5/2006 | Wilkinson et al. |
| 7,083,592 | B2 | 8/2006 | Lastovich et al. |
| 7,083,599 | B2 | 8/2006 | Alchas et al. |
| 7,108,679 | B2 | 9/2006 | Alchas |
| 7,115,108 | B2 | 10/2006 | Wilkinson et al. |
| 7,241,275 | B2 | 7/2007 | Alchas et al. |
| 8,187,872 | B2 | 5/2012 | Allen et al. |
| 8,821,856 | B2 | 9/2014 | Baltimore et al. |
| 9,163,248 | B2 | 10/2015 | Chen et al. |
| 2008/0011895 | A1 | 1/2008 | Bleshoy |
| 2008/0118956 | A1 | 5/2008 | Pages |
| 2008/0131466 | A1 | 6/2008 | Reed et al. |
| 2015/0050243 | A1 | 2/2015 | Kaczmarczyk et al. |

FOREIGN PATENT DOCUMENTS

| | | |
|---|---|---|
| WO | 98/32869 A1 | 7/1998 |
| WO | 2009/035528 A2 | 3/2009 |
| WO | 2009/076524 A2 | 6/2009 |
| WO | 2013/149167 A1 | 10/2013 |

OTHER PUBLICATIONS

Powell et al., Sequence and structural determinants required for priming of plus-strand DNA synthesis by the human immunodeficiency virus type 1 polypurine tract, J. Virol. 70:5288-96 (1996).
Renkvist et al., A listing of human tumor antigens recognized by T cells, Cancer Immunology Immunotherapy, 50:3-15 (2001).
Rong Xu et al: "Characterization of immune Responses Elicited in Macaques Immunized Sequentially with Chimeric VEE/SIN Alphavirus Replicon Particles Expressing SIVGag and/or HIVEnv and with Recombinant HIVgp140Env Protein", AIDS Research and Human Retroviruses, Mary Ann Li Ebert, US, vol. 22, No. 10, Oct. 1, 2006 (Oct. 1, 2006), pp. 1022-1030.
Roselli et al., Brachyury, a driver of the epithelial-mesenchymal transition, is overexpressed in human lung tumors: an opportunity for novel interventions against lung cancer, Clin. Cancer Res., 18:3868-79 (2012).
Singer-Sam et al., Sequence of the promoter region of the gene for human X-linked 3-phosphoglycerate kinase, Gene., 32:409-417 (1984).
Stoute et al., A preliminary evaluation of a recombinant circumsporozoite protein vaccine against Plasmodium falciparum malaria. RTS,S Malaria Vaccine Evaluation Group, N. Engl. J. Med., 336:86-91 (1997).
Strauss et al., The alphaviruses: gene expression, replication, and evolution, Microbiol. Rev., 58:491-562 (1994).
Szymczak et al., Correction of multi-gene deficiency in vivo using a single 'self-cleaving' 2A peptide-based retroviral vector, Nat. Biotechnol., 22:589-594 (2004).
Taganov et al., MicroRNAs and immunity: tiny players in a big field, Immunity 26:133-137 (2007).
Tamberg et al., Insertion of EGFP into the replicase gene of Semliki Forest virus results in a novel, genetically stable marker virus, J.Gen.Virol., 88:1225-30 (2007).
Tareen et al., Design of a novel integration-deficient lentivector technology that incorporates genetic and posttranslational elements to target human dendritic cells, Molecular Therapy, 22:575-587 (2014).
Thomsen et al., Promoter-regulatory region of the major immediate early gene of human cytomegalovirus, Proc. Natl. Acad. Sci. USA., 81:659-63 (1984).
Tiemann et al., RNAi-based therapeutics-current status, challenges and prospects, EMBO Mol. Med., 1:142051 (2009).
Trang et al., MicroRNAs as potential cancer therapeutics, Oncogene Suppl., 2:S52-7 (2008).
Wang et al., High-affinity laminin receptor is a receptor for Sindbis virus in mammalian cells, J. Virol., 66:4992-5001 (1992).
West et al., Mutations in the endodomain of Sindbis virus glycoprotein E2 define sequences critical for virus assembly, J. Virol., 80:4458-4468 (2006).
Wigler et al., DNA-mediated transfer of the adenine phosphoribosyltransferase locus into mammalian cells, Proc. Natl. Acad. Sci. USA., 76:1373-76 (1979).
Zufferey et al., Self-inactivating lentiviral vector for safe and efficient in vivo gene delivery, Multiply attenuated lentiviral vector achieves efficient gene delivery in vivo, J. Virol., 72:9873-9880 (1998).
Zufferey et al., Woodchuck Hepatitis Virus Posttranscriptional Regulatory Element Enhances Expression of Transgenes Delivered by Retroviral Vectors, J. Virol., 73:2886-2892 (1999).
Adra et al., Cloning and expression of the mouse pgk-1 gene and the nucleotide sequence of its promoter, Gene., 60:65-74 (1987).
Apolonia, Thesis submitted to University College London, 82-97 (2009).
Banchereau et al., Dendritic cells as vectors for therapy, Cell., 106:271-274 (2001).
Bear et al., Heparin-binding and patterns of virulence for two recombinant strains of Sindbis virus, Virology, 347:183-190 (2006).
Bernard et al., Mutations in the E2 glycoprotein of Venezuelan equine encephalitis virus confer heparan sulfate interaction, low morbidity, and rapid clearance from blood of mice, Virology, 276:93-103 (2000).
Boon et al., Tumor antigens recognized by T lymphocytes, Annual Review of Immunology, 12:337-365 (1994).
Boshart et al., A very strong enhancer is located upstream of an immediate early gene of human cytomegalovirus, Cell, 41:521-30 (1985).
Brown et al., Structure-based mutagenesis of the human immunodeficiency virus type 1 DNA attachment site: effects on integration and cDNA synthesis, J. Virol. 73:9011-20 (1999).
Cavrois et al., A sensitive and specific enzyme-based assay detecting HIV-1 virion fusion in primary T lymphocytes, Nat. Biotechnol., 20:1151-1154 (2002).
Chang et al., Adjuvant activity of incomplete Freund's adjuvant, Advanced Drug Delivery Reviews, 32:173-186 (1998).
Chen et al., Oncology meets immunology: the cancer-immunity cycle, Immunity, 39:1-10 (2013).
Coffin et al., Retroviruses, Cold Spring Harbor Laboratory Press, N.Y. (1997).
Communication pursuant to Article 94(3) EPC, EP. App. No. 16798347.7, dated Feb. 14, 2019, 5 pages.
Dahlberg et al., Micromanagement during the innate immune response, Sci. STKE, 387:pe25 (2007).
De Felipe et al., Targeting of proteins derived from self-processing polyproteins containing multiple signal sequences, Traffic, 5:616-626 (2004).
Deglon et al., Self-inactivating lentiviral vectors with enhanced transgene expression as potential gene transfer system in Parkinson's disease, Hum. Gene. Ther., 11:179-190 (2000).
Dobson et al., Conservation of high efficiency promoter sequences in *Saccharomyces cerevisiae*, Nucleic Acids Res., 10:2625-2637 (1982).
Drose et al., Bafilomycins and concanamycins as inhibitors of V-ATPases and P-ATPases, J. Exp. Biol., 200:1-8 (1997).

(56) References Cited

OTHER PUBLICATIONS

Engelman et al., Multiple effects of mutations in human immunodeficiency virus type 1 integrase on viral replication, J. Virol., 69:2729-36 (1995).
Fang et al., Stable antibody expression at therapeutic levels using the 2A peptide, Nat. Biotech., 23:584-590 (2005).
Fire et al., Potent and specific genetic interference by double-stranded RNA in Caenorhabditis elegans, Nature, 391:806-11 (1998).
Gardner et al., Infection of human dendritic cells by a sindbis virus replicon vector is determined by a single amino acid substitution in the E2 glycoprotein, J. Virol., 74:11849-57 (2000).
Geijtenbeek et al., et al., Self- and nonself-recognition by C-type lectins on dendritic cells, Annu. Rev. Immunol., 22:33-54 (2004).
Graham et al., A new technique for the assay of infectivity of human adenovirus 5 DNA, Virol., 52:456-67 (1973).
Griffin et al., Binding of Sindbis virus to cell surface heparan sulfate, J. Virol., 72:7349-56 (1998).
Gunning et al., A human beta-actin expression vector system directs high-level accumulation of antisense transcripts, Proc. Natl. Acad. Sci. USA, 84:4831-4835 (1989).
Hamilton et al., Cancer vaccines targeting the epithelial-mesenchymal transition: tissue distribution of brachyury and other drivers of the mesenchymal-like phenotype of carcinomas, Semin. Oncal., 39:358-66 (2012).
International Preliminary Report on Patentability received for PCT Patent Application No. PCT/US16/61092, dated May 24, 2018, 10 pages.
International Search Report and Written Opinion received for PCT Patent Application No. PCT/US16/61092, dated Mar. 27, 2017, 15 pages.
Iwakuma et al., Self-inactivating lentiviral vectors with U3 and U5 modifications, Virology, 261:120-132 (1999).
Klimstra et al., Adaptation of Sindbis virus to BHK cells selects for use of heparan sulfate as an attachment receptor, J. Virol., 72:7357-66 (1998).
Klimstra et al., DC-SIGN and L-SIGN can act as attachment receptors for alphaviruses and distinguish between mosquito cell- and mammalian cell-derived viruses, J. Virol., 77:12022-12032 (2003).
Kung et al., A Murine Leukemia Virus (MuLV) Long Terminal Repeat Derived from Rhesus Macaques in the Context of a Lentivirus Vector and MuLV gag Sequence Results in High-Level Gene Expression in Human T Lymphocytes, J. Virol., 74:3668-3681 (2000).
Lieberman et al., Recognition of a small number of diverse epitopes dominates the cytotoxic T lymphocytes response to HIV type 1 in an infected individual, AIDS Res. Hum. Retroviruses., 13:383-392 (1997).
Livingston et al., The hepatitis B virus-specific CTL responses induced in humans by lipopeptide vaccination are comparable to those elicited by acute viral infection, J. Immunol., 159:1383-1392 (1997).
McCullough et al., Self-replicating Replicon-RNA Delivery to Dendritic Cells by Chitosan-nanoparticles for Translation In Vitro and In Vivo, Molecular Therapy—Nucleic Acids 3:e173 (2014).
McWilliams et al., Mutations in the 5' end of the human immunodeficiency virus type 1 polypurine tract affect RNase H cleavage specificity and virus titer, J. Virol., 77:11150-11157 (2003).
Meissner et al., Development of an inducible pol III transcription system essentially requiring a mutated form of the TATA-binding protein, Nucleic Acids Research, 29:1672-1682 (2001).
Menendez-Arias et al., Cytotoxic T-lymphocyte responses to HIV-1 reverse transcriptase (review), Viral Immunol., 11:167-181 (1998).
Miyoshi et al., Development of a self-inactivating lentivirus vector, J. Virol., 72:8150-7 (1998).
Moore et al., HIV-1 RNA dimerization: It takes two to tango, AIDS Rev., 11:91-102 (2009).
Mukhopadhyay et al., A structural perspective of the flavivirus life cycle, Nature Rev. Microbiol., 3:13-22 (2005).
Navaratnarajah et al., Functional characterization of the sindbis virus E2 glycoprotein by transposon linker-insertion mutagenesis, J. Virol., 363:124-147 (2007).
Niesters et al., Mutagenesis of the conserved 51-nucleotide region of Sindbis virus, J. Virol., 64:1639-47 (1990).
Nightingale et al., Transient gene expression by nonintegrating lentiviral vectors, Mol. Ther., 13:1121-32 (2006).
Ohkawa et al., Control of the functional activity of an antisense RNA by a tetracycline-responsive derivative of the human U6 snRNA promoter, Human Gene Therapy, 11:577-585 (2000).
Palena et al., Overexpression of the EMT driver brachyury in breast carcinomas: association with poor prognosis, J. Natl. Cancer Inst., 9:106 (2014).
Pardoll, The blockade of immune checkpoints in cancer immunotherapy, Nature, 12:252-264 (2012).
Paule et al., Survey and summary: transcription by RNA polymerases I and III, Nucleic Acids Research, 28:1283-1298 (2000).
Pfeifer et al., Gene therapy: promises and problems, Annu. Rev. Genomics Hum. Genet., 2:177-211 (2001).

FIGURE 2
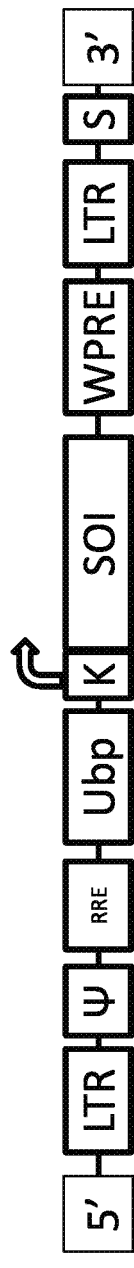
2A Typical Lentiviral Vector Genome
Chimeric Lentiviral-RNA Replicon Vector Genomes
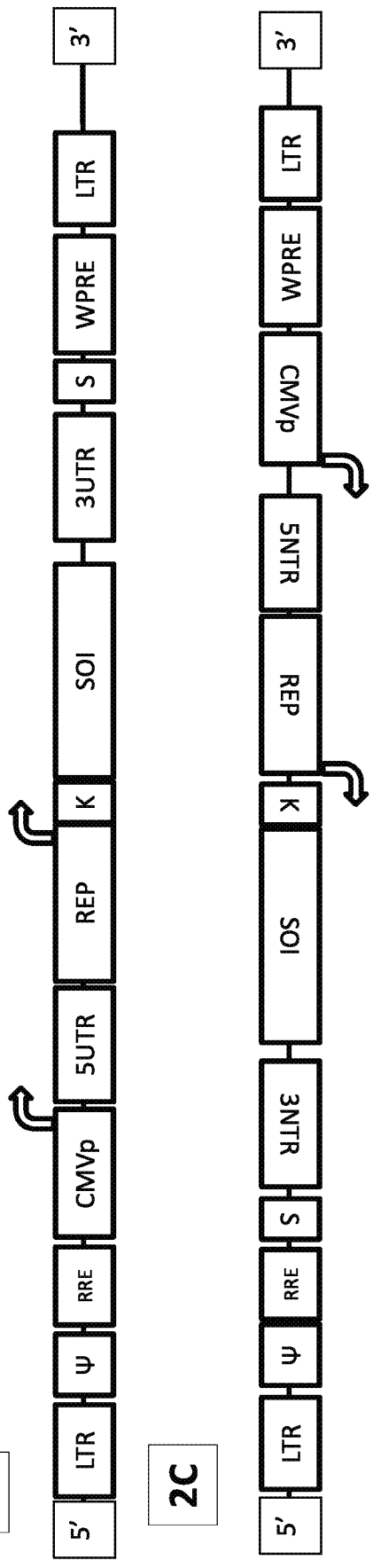

RETROVIRAL VECTOR FOR THE ADMINISTRATION AND EXPRESSION OF REPLICON RNA EXPRESSING HETEROLOGOUS NUCLEIC ACIDS

TECHNICAL FIELD

This patent application relates generally to gene delivery using a chimeric, retroviral-RNA replicon vector particle for increased expression of transgenes in a host cell. In particular, the chimeric vectors described herein can be used in any of a variety of settings including vaccine settings.

BACKGROUND

The Alphavirus genus includes a variety of viruses, all of which are members of the Togaviridae family. The alphaviruses include Eastern Equine Encephalitis Virus (EEE), Venezuelan Equine Encephalitis Virus (VEE), Everglades Virus, Mucambo Virus, Pixuna Virus, Western Equine Encephalitis Virus (WEE), Sindbis Virus, Semliki Forest Virus, Middleburg Virus, Chikungunya Virus, O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J virus, Fort Morgan Virus, Ndumu Virus, and Buggy Creek Virus and any other virus classified by the International Committee on Taxonomy of Viruses (ICTV) as an alphavirus, as well as subgroups thereof as are known in the art. The viral genome is a single-stranded, messenger-sense RNA, modified at the 5'-end with a methylated cap and at the 3'-end with a variable-length poly (A) tract. The 5' end of the genome encodes 4 nonstructural proteins. These proteins form the replicase complex for transcription and replication of the RNA genome. The replicase complex catalyzes cytoplasmic self amplification of the recombinant RNA and high-level production of any transgene correctly inserted into the replicon genome.

Lentiviral vectors (LVV) provide an excellent tool for targeted delivery of gene sequences of interest in vivo, in particular for inducing an immune response by transducing non-dividing cells such as dendritic cells. However, use of these vectors generally does not provide high expression levels of the proteins they encode, which may result in suboptimal function in a gene therapy setting. While LVV activate dendritic cells resulting in expression of costimulatory molecules required for effective T-cell activation, such as CD80 and CD86, this is typically done in a low-inflammatory fashion that leads to early memory formation but potentially suboptimal induction of effector T-cells.

It may therefore be desirable in certain circumstances of gene therapy or genetic immunization to use improved LVV that (i) express genes of interest to high levels and (ii) activate dendritic cells in a more inflammatory way to modulate the ensuing immune response. Furthermore, significant dose-sparing may be realized using such vectors.

These and other advantages are disclosed herein.

SUMMARY OF THE INVENTION

One aspect of the present disclosure provides a replication incompetent, chimeric retroviral-RNA replicon vector particle, comprising: a) an envelope glycoprotein; and b) a retroviral vector genome comprising: i. a 5'LTR; ii. a packaging sequence; iii. a promoter; iv. an alphaviral replicon sequence comprising: a) a 5' untranslated region (5'UTR); b) a sequence encoding an alphavirus replicase; c) a heterologous nucleic acid sequence of interest (SOI); and v. a 3'LTR wherein the 3'LTR is optionally a self inactivating 3'LTR.

Another aspect of the present disclosure provides a chimeric retroviral-RNA replicon vector particle, comprising: a) an envelope glycoprotein; b) retroviral gag polyprotein comprising matrix, capsid and nucleocapsid proteins; c) a retroviral protease; and d) an alphaviral replicon sequence comprising in a 5' to 3' direction: i) a polynucleotide sequence comprising an alphavirus replication signal comprising at least a 5'UTR and a first copy of a polynucleotide sequence comprising a portion of the nsP1 coding sequence which comprises at least a conserved sequence element (CSE); ii) a retroviral packaging sequence iii) an IRES; iv) a polynucleotide sequence encoding a full-length REP comprising a second copy of the nucleotide sequence comprising a portion of the nsP1 coding sequence comprising at least the CSE, wherein the second copy of the polynucleotide sequence is codon modified and in frame with the remainder of the sequence encoding the full-length REP; and v) a heterologous nucleic acid sequence of interest (SOI), wherein the SOI does not encode a), b), or c). In one embodiment of the chimeric retroviral-RNA replicon vector particles disclosed herein, the alphaviral replicon sequence of d) comprises the polynucleotide sequence set forth in SEQ ID NO:2.

Another aspect of the present disclosure provides a chimeric retroviral-RNA replicon vector particle, comprising: a) an envelope glycoprotein; b) a retroviral gag polyprotein comprising matrix, capsid and nucleocapsid proteins; c) a retroviral protease; and d) an alphaviral replicon sequence comprising in a 5' to 3' direction: i) a polynucleotide sequence comprising an alphavirus replication signal comprising at least a 5'UTR and a first copy of a polynucleotide sequence comprising a portion of the nsP1 coding sequence comprising at least a CSE; ii) a retroviral packaging sequence modified to contain no stop codons; iii) a polynucleotide sequence encoding a 2A endoprotease cleavage site; iv) a polynucleotide sequence encoding a full-length REP comprising a second copy of the nucleotide sequence comprising a portion of the nsP1 coding sequence comprising at least the CSE, wherein the second copy of the polynucleotide sequence is codon modified and in frame with the remainder of the sequence encoding the full-length REP; and v) a heterologous nucleic acid sequence of interest (SOI), wherein the SOI does not encode a), b), or c). In one embodiment of the chimeric retroviral-RNA replicon vector particle, the alphaviral replicon sequence of d) comprises the polynucleotide sequence set forth in SEQ ID NO:3.

A further aspect of the present disclosure provides a chimeric retroviral-RNA replicon vector particle, comprising: a) an envelope glycoprotein; b) a retroviral gag polyprotein comprising matrix, capsid and nucleocapsid proteins; c) a retroviral protease; and d) an alphaviral replicon sequence comprising in a 5' to 3' direction: i) a polynucleotide sequence comprising an alphavirus 5'UTR; ii) a polynucleotide sequence encoding a full-length REP wherein the polynucleotide sequence, following an opal stop codon in nsP3, which polynucleotide sequence encodes a proteolytic cleavage recognition site, is duplicated and wherein either a retroviral packaging signal and an RES or a retroviral packaging signal modified to contain no stop codons, is inserted between the duplicated sequence encoding the proteolytic cleavage recognition site; and iii) a heterologous nucleic acid sequence of interest (SOI), wherein the SOI does not encode a), b), or c). In certain embodiments of the chimeric retroviral-RNA replicon vector particles described herein the proteolytic cleavage recognition site comprises the amino acid sequence set forth in SEQ ID NO:4.

In another embodiment of the chimeric retroviral-RNA replicon vector particles described herein, the vector genome further comprises a hepatitis D ribozyme sequence. In other embodiments of the chimeric retroviral-RNA replicon vector particles disclosed herein, the retroviral packaging sequence is a lentiviral packaging sequence. In another embodiment of any of the chimeric retroviral-RNA replicon vector particles described herein, the retroviral packaging sequence is not a Rous sarcoma virus packaging sequence. In a further embodiment of any of the chimeric retroviral-RNA replicon vector particles described herein, the alphaviral replicon sequence is derived from an alphavirus selected from the group consisting of Venezuelan equine encephalitis virus, Eastern equine encephalitis virus, Middelburg virus, Ndumu virus, Semliki Forest virus, Bebaru virus, Chikungunya virus, Mayaro virus, Ross River virus, Getah virus, Aura virus, Babanki virus, Sindbis virus, Ockelbo virus, and Whataroa virus. In another embodiment of the chimeric retroviral-RNA replicon vector particles described herein the envelope glycoprotein comprises a VSVg, an alphavirus E2 glycoprotein, a retroviral envelope glycoprotein, or a targeting antibody. In certain embodiments of the chimeric retroviral-RNA replicon vector particles described herein the promoter is selected from the group consisting of a ubiquitin promoter, a CMV promoter, an EF 1 alpha promoter, an MHC class I promoter, and an MHC class II promoter. In another embodiment of the chimeric retroviral-RNA replicon vector particles described herein, the retroviral vector genome comprises a 3' PPT which has been deleted or otherwise mutated to be nonfunctional. In one embodiment of the chimeric retroviral-RNA replicon vector particles herein, the promoter and the alphaviral replicon sequence are in a reverse (3' to 5') orientation. See e.g., FIG. 2C.

In additional embodiments of the chimeric retroviral-RNA replicon vector particles described herein, the SOI encodes one or more antigens, or one or more cytokines, one or more immune checkpoint inhibitors, or a combination of the foregoing. In another embodiment, the SOI encodes a tumor associated antigen, a viral antigen, a bacterial antigen, or a fungal antigen. In yet a further embodiment, the SOI encodes a therapeutic protein.

In certain embodiments of the chimeric retroviral-RNA replicon vector particles described herein, the retroviral vector genome is a lentiviral vector genome.

Another aspect of the present disclosure provides pharmaceutical compositions comprising any of the chimeric retroviral RNA replicon vector particles disclosed herein.

Another aspect of the present disclosure provides a method of inducing an immune response in a subject, comprising administering to the subject a pharmaceutical composition comprising a chimeric retroviral RNA replicon vector particle described herein.

Another aspect of the present disclosure provides a method of expressing a therapeutic sequence of interest to a target cell in a subject comprising administering to the subject a pharmaceutical compositions comprising any of the chimeric retroviral RNA replicon vector particles disclosed herein.

Another aspect of the present disclosure provides a method of treating cancer in a subject, comprising administering to the subject a pharmaceutical compositions comprising any of the chimeric retroviral RNA replicon vector particles disclosed herein. In certain embodiments, the SOI of such chimeric retroviral RNA replicon vector particles encodes one or more tumor associated antigens and optionally one or more immune checkpoint inhibitors or one or more cytokines, or a combination thereof. In certain embodiments, the methods herein further comprise administering an additional therapeutic agent. In this regard, the additional therapeutic agent may be selected from the group consisting of a cytokine, an immune checkpoint inhibitor, a TLR agonist, a chemotherapeutic agent, and radiation.

Another aspect of the present invention provides a method of treating an infectious disease in a subject, comprising administering to the subject a pharmaceutical compositions comprising any of the chimeric retroviral RNA replicon vector particles disclosed herein wherein the SOI encodes an antigen associated with the infectious disease.

Another aspect of the present disclosure provides packaging systems for producing the chimeric retroviral-RNA replicon vector particles described herein. Such packaging systems comprise a packaging cell transfected or otherwise modified to contain: a) a first nucleic acid molecule encoding an envelope; b) a second nucleic acid molecule encoding gag and pol proteins; c) optionally, a third nucleic acid molecule encoding rev; and d) a fourth nucleic acid molecule comprising a retroviral vector genome as disclosed herein. In one embodiment, the retroviral vector genome comprises: i. a 5'LTR; ii. a packaging sequence; iii. a promoter; iv. an alphaviral replicon sequence comprising: a) a 5' untranslated region (5'UTR); b) a sequence encoding an alphavirus replicase; c) a heterologous nucleic acid sequence of interest (SOI); and v. a 3'LTR wherein the 3'LTR is optionally a self inactivating 3'LTR.

Another aspect of the present disclosure provides a packaging system for producing a chimeric retroviral-RNA replicon vector particle, wherein the particle is reverse transcriptase independent, comprising a packaging cell transfected or otherwise modified to contain: a) a first nucleic acid molecule encoding an envelope; b) a second nucleic acid molecule encoding gag and pol proteins, wherein the nucleic acid molecule optionally encodes a nonfunctional reverse transcriptase protein; c) a third nucleic acid molecule comprising an alphaviral replicon sequence comprising in a 5' to 3' direction: i) a polynucleotide sequence comprising an alphavirus replication signal comprising at least a 5'UTR and a first copy of a polynucleotide sequence comprising a portion of the nsP1 coding sequence which comprises at least a CSE; ii) a retroviral packaging sequence iii) an IRES; iv) a polynucleotide sequence encoding a full-length REP comprising a second copy of the nucleotide sequence comprising a portion of the nsP1 coding sequence comprising at least the CSE, wherein the second copy of the polynucleotide sequence is codon modified and in frame with the remainder of the sequence encoding the full-length REP; and v) a heterologous nucleic acid sequence of interest (SOI).

Another aspect of the present disclosure provides a packaging system for producing a chimeric retroviral-RNA replicon vector particle, wherein the particle is reverse transcriptase independent, comprising a packaging cell transfected or otherwise modified to contain: a) a first nucleic acid molecule encoding an envelope; b) a second nucleic acid molecule encoding gag and pol proteins, wherein the nucleic acid molecule optionally encodes a nonfunctional reverse transcriptase protein; c) a third nucleic acid molecule comprising an alphaviral replicon sequence comprising in a 5' to 3' direction: i) a polynucleotide sequence comprising an alphavirus replication signal comprising at least a 5'UTR and a first copy of a polynucleotide sequence comprising a portion of the nsP1 coding sequence comprising at least a CSE (CSE); ii) a retroviral packaging sequence modified to contain no stop codons; iii) a polynucleotide sequence encoding a 2A endoprotease cleavage site; iv) a polynucleotide sequence encoding a full-length REP comprising a second copy of the nucleotide sequence comprising a portion of the nsP1 coding sequence comprising at least the CSE, wherein the second copy of the polynucleotide sequence is codon modified and in frame with the remainder of the sequence encoding the full-length REP; and v) a heterologous nucleic acid sequence of interest (SOI).

Yet another aspect of the present disclosure provides a packaging system for producing a chimeric retroviral-RNA replicon vector particle, wherein the particle is reverse transcriptase independent, comprising a packaging cell transfected or otherwise modified to contain: a) a first nucleic acid molecule encoding an envelope; b) a second nucleic acid molecule encoding gag and pol proteins, wherein the nucleic acid molecule optionally encodes a nonfunctional reverse transcriptase protein; c) a third nucleic acid molecule comprising an alphaviral replicon sequence comprising in a 5' to 3' direction: i) a polynucleotide sequence comprising an alphavirus 5'UTR; ii) a polynucleotide sequence encoding a full-length REP wherein the polynucleotide sequence, following an opal stop codon in nsP3, which polynucleotide sequence encodes a proteolytic cleavage recognition site, is duplicated and wherein either a retroviral packaging signal and an RES or a retroviral packaging signal modified to contain no stop codons, is inserted between the duplicated sequence encoding the proteolytic cleavage recognition site; and iii) a heterologous nucleic acid sequence of interest (SOI). In certain embodiments, the proteolytic cleavage recognition site comprises the amino acid sequence set forth in SEQ ID NO:4.

In certain embodiments of the packaging systems described herein the envelope glycoprotein comprises a VSVg or an alphavirus E2 glycoprotein. In other embodiments of the packaging systems described herein, the retroviral vector genome comprises a 3' PPT which has been deleted or otherwise mutated to be nonfunctional. In a further embodiment of the packaging systems the pol protein comprises a nonfunctional integrase. In one particular embodiment of the packaging systems herein, the nonfunctional integrase has a D64V mutation.

Another aspect of the present disclosure provides methods of producing the chimeric retroviral-RNA replicon vector particles herein by culturing the packaging cells of any of the packaging systems described herein.

Another aspect of the present disclosure provides a chimeric retroviral-RNA replicon vector particle as described herein, or a pharmaceutical composition comprising any of the retroviral-RNA replicon vector particles as described herein for use in therapy. In certain embodiments, such chimeric retroviral-RNA replicon vector particles as described herein, or pharmaceutical compositions comprising any of the retroviral-RNA replicon vector particles as described herein are for use in a method of treatment of a human or animal subject.

Another aspect of the present disclosure provides a therapeutic or prophylactic vaccine comprising the chimeric retroviral-RNA replicon vector particles described herein or a pharmaceutical composition comprising any of the retroviral-RNA replicon vector particles as described herein and a pharmaceutically acceptable excipient.

One aspect of the present invention provides a replication incompetent, chimeric retroviral-RNA replicon vector particle, comprising:

a) an envelope glycoprotein; and b) a retroviral vector genome comprising: i. a 5'LTR; ii. a packaging sequence; iii. a promoter; iv. an alphaviral replicon sequence comprising: a. a 5' untranslated region (5'UTR); b. a sequence encoding an alphavirus RNA-dependent RNA polymerase (alphaviral nonstructural proteins 1-4); c. a heterologous nucleic acid sequence of interest (SOI); and v. a 3'LTR wherein the 3'LTR is optionally a self inactivating 3'LTR.

Another aspect of the present invention provides a chimeric retroviral-RNA replicon vector particle, comprising: a) an envelope glycoprotein; b) retroviral gag polyprotein comprising matrix, capsid and nucleocapsid proteins; c) a retroviral protease; and d) a vector genome comprising: i. a retroviral packaging sequence; ii. an alphaviral replicon sequence comprising: a. a 5' untranslated region (5'UTR); b. a sequence encoding an alphavirus RNA-dependent RNA polymerase (alphaviral nonstructural proteins 1-4); and c. a heterologous nucleic acid sequence of interest (SOI), wherein the SOI does not encode a), b), or c); wherein the particle is reverse transcriptase independent.

In certain embodiments of the replication incompetent, chimeric retroviral-RNA replicon vector particles described herein, the alphaviral replicon sequence is derived from an alphavirus selected from the group consisting of Venezuelan equine encephalitis virus, Eastern equine encephalitis virus, Middelburg virus, Ndumu virus, Semliki Forest virus, Bebaru virus, Chikungunya virus, Mayaro virus, Ross River virus, Getah virus, Aura virus, Babanki virus, Sindbis virus, Ockelbo virus, and Whataroa virus. In certain embodiments, of the chimeric retroviral-RNA replicon vector particles described herein, the envelope glycoprotein comprises a VSV-G, and alphavirus E2 glycoprotein, a retroviral envelope glycoprotein, or a targeting antibody. In another embodiment of the chimeric retroviral-RNA replicon vector particles described herein, the promoter is selected from the group consisting of a ubiquitin promoter, a CMV promoter, an EF 1 alpha promoter, an MHC class I promoter, and an MHC class II promoter. In one embodiment, the retroviral vector genome comprises a 3' PPT which has been deleted or otherwise mutated to be nonfunctional. In another embodiment of the chimeric retroviral-RNA replicon vector particles described herein, the SOI encodes one or more antigens, or one or more cytokines, one or more checkpoint inhibitors, or a combination of the foregoing. In this regard, the SOI may encode an antigen and the antigen may be a tumor associated antigen, a viral antigen, a bacterial antigen, or a fungal antigen.

In one embodiment, of the chimeric retroviral-RNA replicon vector particles herein, the retroviral vector genome is a lentiviral vector genome.

Another aspect of the present invention provides pharmaceutical compositions comprising any of the replication incompetent, chimeric retroviral RNA replicon vector particles described herein.

Another aspect of the present invention provides a method of inducing an immune response in a subject, comprising administering to the subject a pharmaceutical composition comprising any of the replication incompetent, chimeric retroviral RNA replicon vector particles described herein.

Another aspect of the present invention provides a method of treating cancer in a subject, comprising administering to the subject a pharmaceutical composition comprising a replication incompetent, chimeric retroviral RNA replicon vector particle described herein, wherein the SOI encodes one or more tumor specific or tumor associated antigens and optionally one or more immune checkpoint inhibitors, or one or more agonistic antibodies, or one or more cytokines or chemokines, or a combination thereof.

Another aspect of the present invention provides a method of treating cancer in a subject, comprising administering to the subject a pharmaceutical composition comprising a replication incompetent, chimeric retroviral RNA replicon vector particle described herein, wherein the SOI encodes one or more tumor associated antigens and optionally one or more checkpoint inhibitors or one or more cytokines, or a combination thereof. In certain embodiments, the method further comprises administering an additional therapeutic agent. Illustrative therapeutic agents for use herein include, but are not limited to, a cytokine, a checkpoint inhibitor, a TLR agonist, a chemotherapeutic agent, and radiation.

Another aspect of the present invention provides a method of treating an infectious disease in a subject, comprising administering to the subject a pharmaceutical composition comprising a replication incompetent, chimeric retroviral RNA replicon vector particle described herein wherein the SOI encodes an antigen associated with the infectious disease or an antibody directed against antigens associated with the infectious disease.

One aspect of the present invention provides a packaging system for producing a replication incompetent, chimeric retroviral-RNA replicon vector particle, comprising:
a) a first nucleic acid molecule encoding an envelope;
b) a second nucleic acid molecule encoding gag and pol proteins;
c) a third nucleic acid molecule encoding rev; and
d) a fourth nucleic acid molecule comprising a chimeric retroviral-RNA replicon vector genome comprising a sequence of interest.

Another aspect of the present invention provides a packaging system for producing a replication incompetent, chimeric retroviral-RNA replicon vector particle, wherein the particle is reverse transcriptase independent, comprising:
a) a first nucleic acid molecule encoding an envelope;
b) a second nucleic acid molecule encoding gag and pol proteins, wherein the nucleic acid molecule encodes a nonfunctional reverse transcriptase protein;
c) a third nucleic acid molecule comprising a chimeric retroviral-RNA replicon vector genome comprising a sequence of interest, a poly A signal, and a transcriptional stop. In one embodiment of the packaging systems described herein, the envelope glycoprotein comprises a VSVg or an alpha virus E2 glycoprotein. In another embodiment of the packaging systems described herein, the vector genome comprises a 3' PPT which has been deleted or otherwise mutated to be nonfunctional. In a further embodiment of the packaging systems described herein the pol protein comprises a nonfunctional integrase. In this regard, the nonfunctional integrase may have a D64V mutation.

Another aspect of the present invention provides a method of producing a replication incompetent, chimeric retroviral-RNA replicon vector particle comprising expressing in an isolated cell:
a) a first nucleic acid molecule encoding an envelope;
b) a second nucleic acid molecule encoding gag and pol proteins;
c) a third nucleic acid molecule encoding rev; and
d) a fourth nucleic acid molecule comprising a chimeric retroviral-RNA replicon vector genome comprising a sequence of interest.

An additional aspect of the present invention provides replication incompetent, chimeric retroviral-RNA replicon vector particles as described herein as well as pharmaceutical compositions comprising such particles for use in a method of treatment of a human or animal subject.

Another aspect of the present invention provides a therapeutic or prophylactic vaccine comprising the replication incompetent, chimeric retroviral-RNA replicon vector particles as described herein or a pharmaceutical composition comprising such particles and a pharmaceutically acceptable excipient.

Another aspect of the present invention provides a replication incompetent, chimeric retroviral-RNA replicon vector particle as described herein, or pharmaceutical compositions comprising such particles, for use in therapy or prophhylaxis

BRIEF DESCRIPTION OF THE DRAWINGS

FIG. 2A, FIG. 2B, and FIG. 2C is a diagram showing a typical lentiviral vector (FIG. 2A) and 2 different approaches for constructing a chimeric lentiviral—VEE RNA replicon vector (FIG. 2B and FIG. 2C). Abbreviations: LTR—long terminal repeat; UBP—ubiquitin promoter; RRE—rev responsive element; K—Kozak sequence; SOI—sequence of interest; WPRE—woodchuck hepatitis virus responsive element; S-transcription stop signal.

the construct shown in FIG. 2B where the SOI is GFP; 704-VEE-GFP-3'-5': the construct shown in FIG. 2C where the SOI is GFP).

Figure 8:
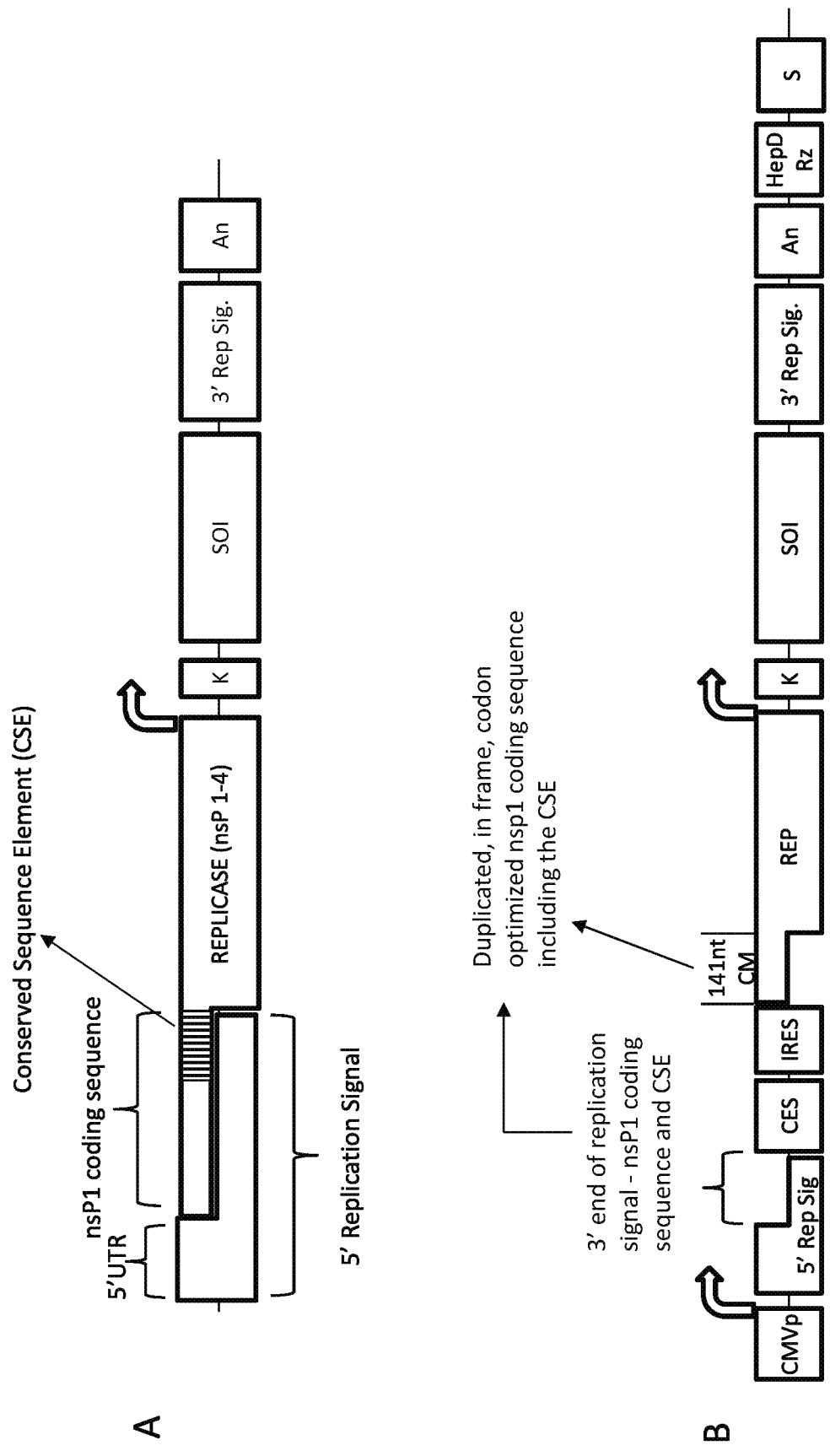
Figure 8:
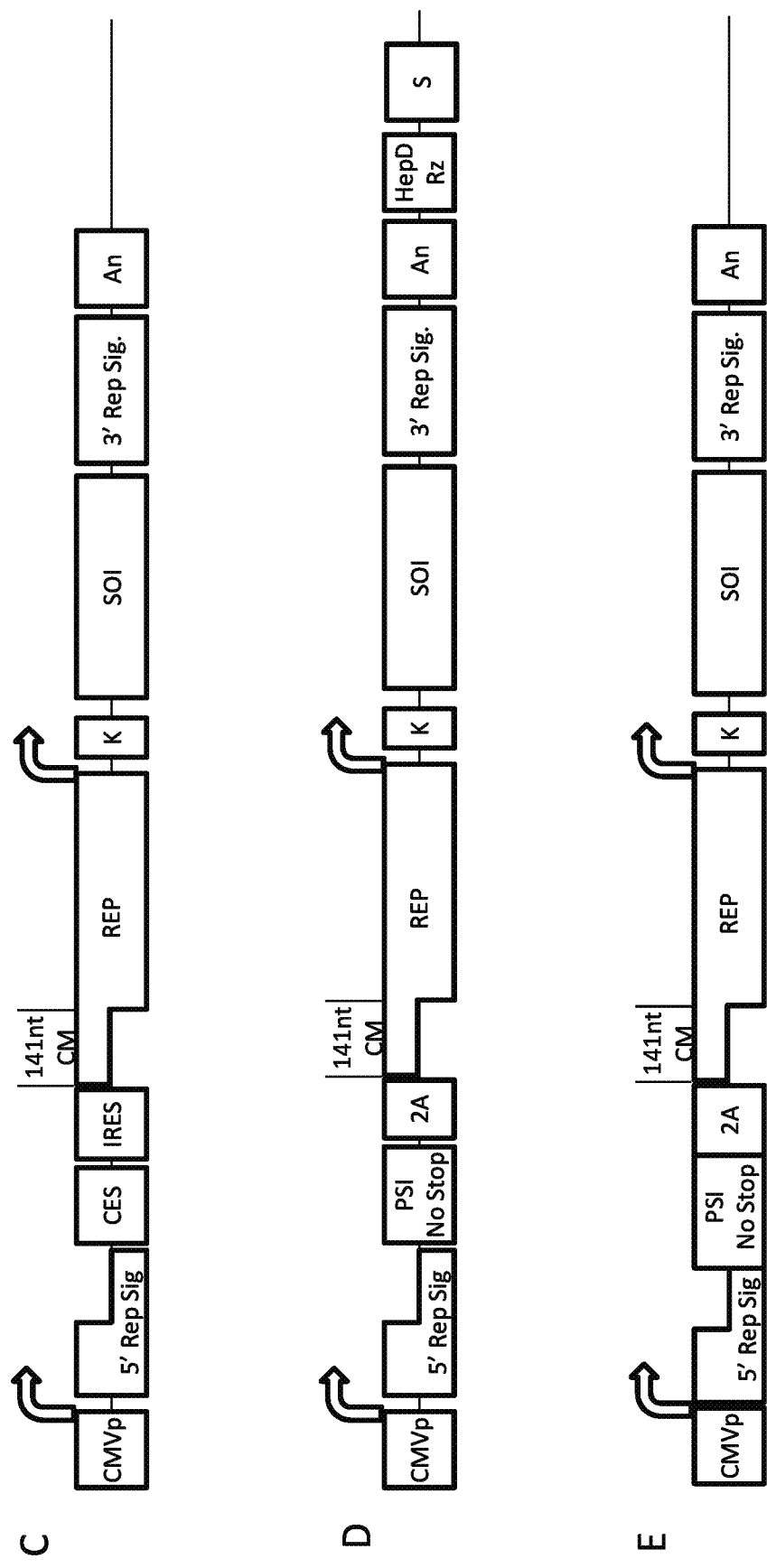
Figure 8:
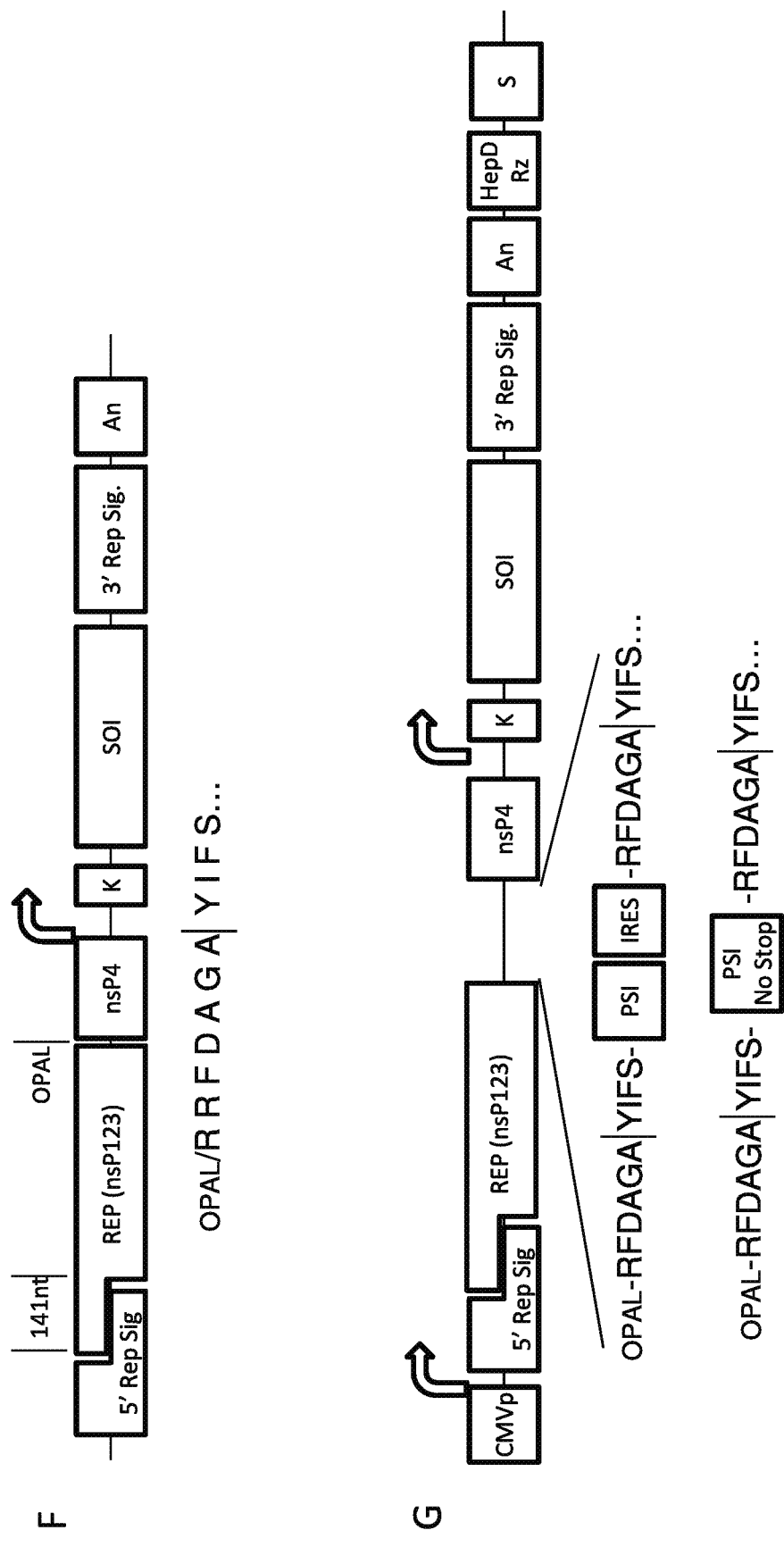

FIG. 8 is a schematic showing various retroviral packaging sequence placement strategies for effective retroviral packaging of alphavirus RNA replicon genomes in those embodiments of chimeric vectors having retroviral packaging signal but lacking other retroviral elements (e.g., LTR, RRE, etc). 8A: The basic structure of the RNA replicon expressing a sequence of interest (SOI) (not to scale). The 5' replication signal spans the 5'UTR and through a portion of the coding sequence for nsP1 including the Conserved Sequence Element (CSE). The entire length of the 5' replication signal and the exact placement and sequence of the CSE varies between alphaviruses. The CSE of the alphavirus used herein is approximately 51 nucleotides in length. In order to function efficiently, the regions of the 5' replication signal that encode the 5'UTR and the CSE should be continuous (uninterrupted) as mutations in this region have been shown to disrupt replication. In some embodiments, the vectors herein insert the RNA packaging signal after the full 5' replication signal. However, in order to encode a full-length Replicase poly-protein (REP; nsP1-4)), the sequence of the 5' replication signal that also codes for the nsP1 (including the CSE) is duplicated, codon modified (CM) and then re inserted in frame to encode the beginning of the nsP1 as shown in FIGS. 8; 8B and 8C: RNA packaging signal (core encapsidation signal, CES) is inserted downstream of the complete continuous 5' replication signal and followed by an IRES, all placed before a duplicated and codon modified version of the first 141 nucleotides encoding the first 47 amino acids of nsP1 in frame with the REP-coding sequence; 8B contains a hepatitis delta virus ribozyme following the poly-A stretch while the 8C construct does not; 8D and 8E: The RNA packaging signal is placed following the complete continuous 5' replication signal and is followed by a 2A cleavage signal which is in turn followed by a duplicated and codon modified version of the first 141 nucleotides encoding the first 47 amino acids of the nsP1 in frame with the REP coding sequence. This requires translational read-through from the 5' end of the transcript, which is achieved by site-directed mutations that remove stop codons in the sequence upstream of the REP gene. 8D contains a hepatitis delta virus ribozyme following the poly-A stretch while the 8E construct does not; 8F: shows the detail of the REP nsP123 and 4 junction of an RNA replicon indicating the opal stop codon and the following 11 amino acids that form a motif for proteolytic cleavage recognition. This sequence is set forth in SEQ ID NO:4. As shown in construct 8G, the RNA packaging signal can be inserted between nsP3 and nsP4 either followed by an IRES or with the removal of the stop codon as shown. YIFS is the beginning amino acid sequence of the nsP4 protein; horizontal line between RFDAGA and YIFS indicates proteolytic cleavage site to produce nsP4; Abbreviations: Rep Sig: Alphaviral 5' or 3' replication signal; PSI: Heterologous sequence containing RNA packaging signal; CES: Core Encapsidation Signal (include psi and dimer initiation signal); No Stop: Sequence altered to contain no stop codons; 2A: Short endoprotease such as FMDV 2A or T2A; 141nt CM: First 141 nucleotides encoding the first ~47 amino acids of the alphaviral replicase-codon modified to abrogate RNA secondary structure and to avoid recombination with the same duplicated region found at the end of the 5' replication signal; IRES: Internal ribosome entry site; REP: Alphaviral replicase, nsP1-4; K: Kozak box; SOI: Sequence of interest; An: poly-A stretch; HepD Rz: hepatitis delta virus ribozyme; SV40 pA: transcription termination and polyadenylation sequence.

Figure 9:
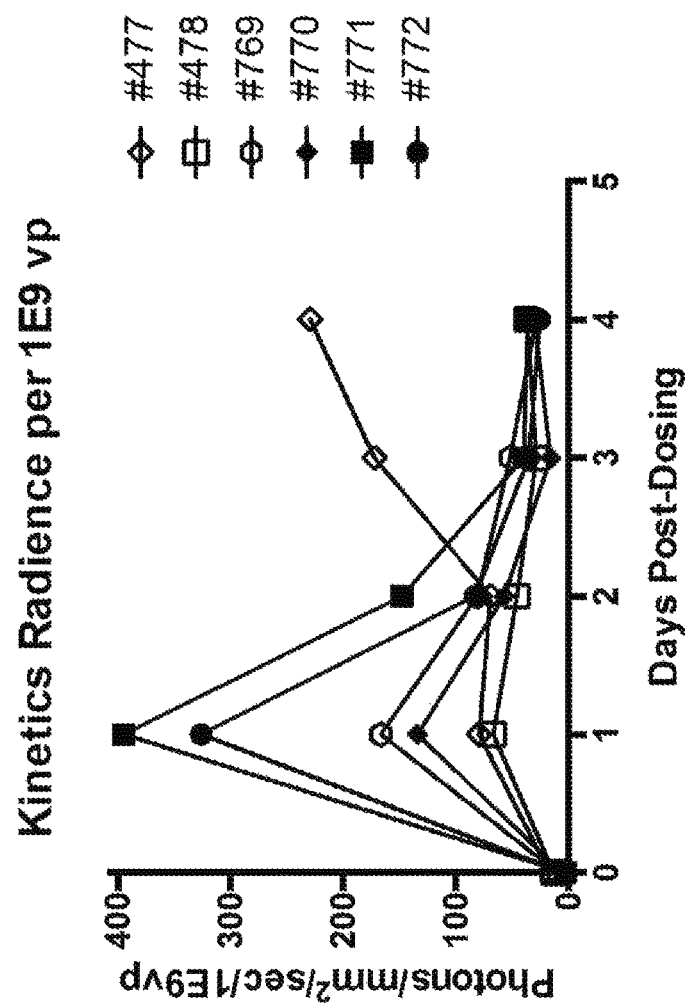

FIG. 9 is a graph of the kinetics of luciferase radiance detected following in vivo administration of chimeric vectors. See Table 1 for detail of vectors used.

BRIEF DESCRIPTION OF THE SEQUENCE IDENTIFIERS

SEQ ID NO:1 is the polynucleotide sequence of an exemplary alphavirus replicon as depicted in FIG. 8A. 5'UTR: 1-44; REP (nsP1-4): 45-7523; Sub-genomic Promoter: 7501-7545; SOI (i.e. GFP): 7574-8293; 3'UTR: 8325-8441.

SEQ ID NO:2 is the polynucleotide of the 5' end of the chimeric alphavirus replicon containing a retroviral packaging sequence as depicted in FIGS. 8B and 8C. 5'UTR: 1-44; Partial nsP1: 45-185 (51 nucleotide Conserved Sequence Element (CSE): 133-183); HIV Core Encapsidation Sequence (CES): 186-425; (HIV DIS: 338-343; HIV PSI: 393-406); RES of EMCV: 426-1013; nsP1 duplication (codon-modified): 1014-1154.

SEQ ID NO:3 is the polynucleotide of the 5' end of the chimeric alphavirus replicon containing a retroviral packaging sequence as depicted in FIGS. 8D and 8E. 5'UTR: 1-44; Partial nsP1: 45-185; (51 nucleotide CSE: 133-183); HIV Core Encapsidation Sequence: 186-425 (HIV DIS: 338-343; HIV PSI: 393-406); 2A: 426-479; nsP1 duplication (codon-modified): 480-621.

SEQ ID NO:4 is the RRFDAGAYIFS amino acid sequence of the cleavage site located at the junction of nsP3 and nsP4 in alphaviruses (between the opal stop codon and the beginning of the snP4 protein) as shown in FIG. 8F. —OPAL stop-RRFDAGA_YIFS_—rest of nsP4. YIFS is the beginning of the nsp4 protein. Cleavage occurs between the A and Y residues as depicted by the "I" in FIGS. 8F and 8G.

DETAILED DESCRIPTION

The present disclosure provides chimeric retroviral-RNA replicon vector particles and methods of using same for expressing proteins of interest in vivo. In particular, the chimeric viral vectors described herein can be used for gene therapy, inducing an immune response against particular antigens, and/or expressing immunomodulatory molecules in vivo for improving immune responses.

In general, the chimeric lentiviral-RNA replicon vector particles are produced by a cell line that contains one or more plasmid vectors and/or integrated elements that together encode the components necessary to generate functional vector particles. These chimeric lentiviral-RNA replicon vector particles are typically not replication-competent, i.e., they are only capable of a single round of infection. Most often, multiple plasmid vectors or individual expression cassettes integrated stably into the producer cell chromosome are utilized to separate the various genetic components that generate the chimeric lentiviral-RNA replicon vector particles, however, a single plasmid vector having all of the lentiviral components can be used. In one exemplification, the packaging cell line is transfected with one or more plasmids containing the chimeric lentiviral-RNA replicon vector genome, including LTRs, a cis-acting packaging sequence, and the RNA replicon comprising sequence(s) of interest, at least one plasmid encoding the virus enzymatic and structural components (e.g., gag and pol), and at least one plasmid encoding an envelope glycoprotein. Viral particles bud through the cell membrane and comprise a core that includes typically two RNA genomes containing the RNA replicon comprising the sequence of interest and an envelope glycoprotein that targets cells of interest. When the envelope glycoprotein comprises a Sindbis virus E2 glycoprotein, the glycoprotein may be engineered to have reduced binding to heparan sulfate compared to the reference strain HR. This usually involves at least one amino acid change compared to the HR E2 glycoprotein sequence.

Without wishing to be bound by theory, it is believed that the binding of the viral particle to a cell surface induces endocytosis, bringing the virus into an endosome, triggering membrane fusion, and allowing the virus core to enter the cytosol. For certain embodiments, which utilize integrating lentiviral vector particles, following reverse transcription and migration of the product to the nucleus, the genome of the virus integrates into the target cell genome, incorporating the sequence(s) of interest into the genome of the target cell. To reduce the chance of insertional mutagenesis and to promote transient expression of a designate antigen(s), however, other embodiments utilize non-integrating lentiviral vector particles, which do not integrate into the target cell genome, but instead express the sequence(s) of interest from an episome. Either way, the infected target cell then expresses the sequence(s) of interest, e.g., an antigen, a stimulatory molecule, or other sequence of interest. In certain embodiments, the target cell of interest is a dendritic cell and an antigen can then be processed by dendritic cells and presented to T and B cells, generating an antigen-specific immune response. The specific pathway described above is not required so long as the dendritic cell is able to stimulate an antigen-specific immune response.

The viral particles can be administered to a subject in order to provide a prophylactic or therapeutic effect. The product of the sequence of interest is typically an antigen of a disease-causing agent or a diseased cell (e.g., tumor cell) but may be any immunostimulatory molecule. Following infection of dendritic cells or other target cell of interest and expression of the product, an immune response is generated to the product. The immune response may be humoral or cellular or both.

A. Chimeric Retroviral-RNA Replicon Vector Genome

The chimeric viral vector particle comprises a genome, which comprises the sequence(s) of interest. Other sequences may be included, such as sequences that allow the genome to be packaged into the virus particle and sequences that promote expression of the RNA replicon comprising the sequence(s) of interest following transduction of the target cell. In certain embodiments, the genome can be derived from any of a large number of suitable, available retroviral, e.g., lentiviral, genome based vectors, including those identified for human gene therapy applications, such as those described by Pfeifer and Verma (Annu. Rev. Genomics Hum. Genet. 2:177-211, 2001). For the sake of simplicity, the chimeric retroviral-RNA replicon vector genome is also referred to as "viral vector genome" or "vector genome" or "chimeric vector genome".

1. Backbone

In those embodiments comprising a retroviral backbone, such as those embodiments comprising retroviral LTRs, packaging signal, cPPT, RRE and the like, suitable retroviral vector genomes can be derived from any retrovirus, including alpharetroviruses (Rous sarcoma virus), Betaretroviruses (mouse mammary tumor virus), Gammaretroviruses (Murine leukemia virus; feline leukemia virus), Deltaretroviruses (Bovine leukemia virus; Human T lymphotropic virus (HTLV)), Epsilonretroviruses, Spumaviruses (Simian foamy virus) and lentiviruses. Particularly illustrative retroviral vector genomes include lentiviral vector genomes. Lentiviral vector genomes include those based on Human Immunodeficiency Virus (HIV-1), HIV-2, feline immunodeficiency virus (FIV), equine infectious anemia virus, Simian Immunodeficiency Virus (SIV) and maedi/visna virus. A desirable characteristic of lentiviruses is that they are able to infect both dividing and non-dividing cells, it is not necessary for target cells to be dividing (or to stimulate the target cells to divide). Generally, the genome and envelope glycoproteins will be based on different viruses, such that the resulting viral vector particle is pseudotyped. Safety features of the vector genome are desirably incorporated. Safety features include self-inactivating LTR and a non-integrating genome. Exemplary vectors are discussed further in Examples 1 and 2 and are shown in FIGS. 1-3 and such vectors may be used in embodiments of the invention for expression of proteins of interest. Proteins of interest include any protein of interest to be expressed in vivo. In certain embodiments, such proteins include, but are not limited to, antigens, immunomodulatory proteins, such as cytokines, chemokines, maturation factors and the like.

In some exemplary embodiments, the viral vector genome comprises sequences from a lentivirus genome, such as the HIV-1 genome or the SIV genome. The viral genome construct may comprise sequences from the 5' and 3' LTRs of a lentivirus, and in particular may comprise the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Typically, the LTR sequences are HIV LTR sequences.

The vector genome may comprise an inactivated or self-inactivating 3' LTR (Zufferey et al. J Virol 72: 9873, 1998; Miyoshi et al., J Virol 72:8150, 1998). A self-inactivating vector generally has a deletion of the enhancer and promoter sequences from the 3' long terminal repeat (LTR), which is copied over into the 5' LTR during vector integration. In one instance, the U3 element of the 3' LTR contains a deletion of its enhancer sequence, the TATA box, Sp1 and NF-kappa B sites. As a result of the self-inactivating 3' LTR, the provirus that is generated following entry and reverse transcription will comprise an inactivated 5' LTR. The rationale is to improve safety by reducing the risk of mobilization of the vector genome and the influence of the LTR on nearby cellular promoters. The self-inactivating 3' LTR may be constructed by any method known in the art.

Optionally, the U3 sequence from the lentiviral 5' LTR may be replaced with a promoter sequence in the viral construct, such as a heterologous promoter sequence. This can increase the titer of virus recovered from the packaging cell line. An enhancer sequence may also be included. Any enhancer/promoter combination that increases expression of the viral RNA genome in the packaging cell line may be used. In one example, the CMV enhancer/promoter sequence is used (U.S. Pat. Nos. 5,385,839 and 5,168,062).

In certain embodiments, the vector genome backbone comprises a retroviral packaging signal (psi or core encapsidation signal) and a rev responsive element (RRE) (see e.g., FIG. 2B, FIG. 2C, FIG. 3A) placed outside of the replicon sequences. In other embodiments described elsewhere, the placement of the RNA packaging signal is in the replicon sequence as shown in any of the embodiments outlined in FIG. 8.

In certain embodiments, the risk of insertional mutagenesis is minimized by constructing the lentiviral vector genome to be integration defective. A variety of approaches can be pursued to produce a non-integrating vector genome. These approaches entail engineering a mutation(s) into the integrase enzyme component of the pol gene, such that it encodes a protein with an inactive integrase. The vector genome itself can be modified to prevent integration by, for example, mutating or deleting one or both attachment sites, or making the 3' LTR-proximal polypurine tract (PPT) non-functional through deletion or modification. In addition, non-genetic approaches are available; these include pharmacological agents that inhibit one or more functions of integrase. The approaches are not mutually exclusive, that is, more than one of them can be used at a time. For example, both the integrase and attachment sites can be non-functional, or the integrase and PPT site can be non-functional, or the attachment sites and PPT site can be non-functional, or all of them can be non-functional.

As stated above, one approach is to make and use a non-functional integrase. Integrase is involved in cleavage of viral double-stranded blunt-ended DNA and joining the ends to 5'-phosphates in the two strands of a chromosomal target site. Integrase has three functional domains: N-terminal domain, which contains a zinc-binding motif (HHCC), the central domain core, which contains the catalytic core and a conserved DD35E motif (D64, D116, E152 in HIV-1), and a C-terminal domain, which has DNA binding properties. Point mutations introduced into integrase are sufficient to disrupt normal function. Many integrase mutations have been constructed and characterized (see, Philpott and Thrasher, Human Gene Therapy 18:483, 2007; Apolonia, Thesis submitted to University College London, April 2009, pp, 82-97; Engelman et al. J Virol 69: 2729, 1995; Nightingale et al. Mol Therapy, 13: 1121, 2006). The sequence encoding the integrase protein can be deleted or mutated to render the protein inactive, preferably without significantly impairing reverse transcriptase activity or nuclear targeting, thereby only preventing integration of the provirus into the target cell genome. Acceptable mutations can reduce integrase catalysis, strand transfer, binding to att sites, binding to host chromosomal DNA, and other functions. For example, a single aspartic acid to asparagine substitution at residue 35 of HIV or SIV integrase completely abolishes viral DNA integration. Deletions of integrase will generally be confined to the C-terminal domain. Deletion of coding sequence for residues 235-288 result in a useful non-functional integrase (Engelman et al. J Virol 69:2729, 1995). As further examples, mutations can be generated, for example, Asp64 (residue numbers are given for HIV-1, corresponding residue numbers for integrase from other lentiviruses or retroviruses can be readily determined by one of ordinary skill) (e.g., D64E, D64V), Asp116 (e.g., D116N), Asn120 (e.g., N120K), Glu152, Gln148 (e.g., Q148A), Lys156, Lys159, Trp235 (e.g. W235E), Lys264 (e.g., K264R), Lys266 (e.g., K266R), Lys273 (e.g., K273R). Other mutations can be constructed and tested for integration, transgene expression, and any other desirable parameter. Assays for these functions are well known. Mutations can be generated by any of a variety of techniques, including site-directed mutagenesis and chemical synthesis of nucleic acid sequence. One mutation may be made or more than one of these mutations can be present in integrase. For example, an integrase may have mutations at two amino acids, three amino acids, four amino acids, and so on.

Alternatively or in combination with the use of integrase mutant(s), the attachment sites (att) in U3 and U5 can also be mutated. Integrase binds to these sites and the 3'-terminal dinucleotide is cleaved at both ends of the vector genome. A CA dinucleotide is located at the recessed 3' end; the CA is required for processing, mutation of the nucleotides blocks integration into the host chromosome. The A of the CA dinucleotide is the most critical nucleotide for integration, and mutations at both ends of the genome will give the best results (Brown et al J Virol 73:9011 (1999). In one exemplification, the CA at each end is changed to TG. In other exemplifications, the CA at each end is changed to TG at one end and GT at the other end. In other exemplifications, the CA at each end is deleted; in other exemplifications, the A of the CA is deleted at each end.

Integration can also be inhibited by mutation or deletion of the 3' polypurine tract (PPT) (WO 2009/076524), located proximally to the 3' LTR. The PPT is a polypurine sequence of about 15 nucelotides that can serve as a primer binding site for plus-strand DNA synthesis. In this case, mutations or deletions of PPT targets the reverse transcription process. Without wishing to be held to a mechanism, by mutating or deleting PPT, production of linear DNA is radically reduced and essentially only 1-LTR DNA circles are produced. Integration requires a linear double-stranded DNA vector genome, and integration is essentially eliminated without it. As stated above, a PPT can be made non-functional by mutation or by deletion. Typically, the entire about 15 nt PPT is deleted, although in some embodiments, shorter deletions of 14 nt, 13, nt, 12 nt, 11 nt, 10 nt, 9 nt, 8 nt, 7 nt, 6 nt, 5 nt, 4 nt, 3 nt and 2 nt may be made. When mutations are made, typically multiple mutations are made, especially in the 5' half of the PPT (McWilliams et al., J Virol 77:11150, 2003), although single and double mutations in the first four bases still reduce transcription. Mutations made at the 3' end of PPT generally have a more dramatic effect (Powell and Levin J Virol 70:5288, 1996).

These different approaches to make a vector genome non-integrating can be used individually or in combination. Using more than one approach may be used to build a fail-safe vector through redundant mechanisms. Thus, PPT mutations or deletions can be combined with att site mutations or deletions or with Integrase mutations or PPT mutations or deletions can be combined with both att site mutations or deletions and Integrase mutations. Similarly, att site mutations or deletions and Integrase mutations may be combined with each other or with PPT mutations or deletions.

2. Regulatory Elements

As discussed herein, the viral vector genome comprises a sequence of interest that is desirable to express in target cells. Typically, the sequence of interest is located within the RNA replicon in place of the structural protein genes located just downstream from the nonstructural protein genes of the RNA replicon. The RNA replicon comprising the SOI is typically located between the 5' LTR and 3' LTR sequences. Further, the replicon sequence including the sequence of interest, is preferably in a functional relationship with other genetic elements, for example transcription regulatory sequences including promoters or enhancers, to regulate expression of the replicon sequence comprising the sequence of interest in a particular manner. In certain instances, the useful transcriptional regulatory sequences are those that are highly regulated with respect to activity, both temporally and spatially. Expression control elements that may be used for regulating the expression of the components are known in the art and include, but are not limited to, inducible promoters, constitutive promoters, secretion signals, enhancers and other regulatory elements.

The sequence of interest is expressed from the RNA replicon at high levels, from the RNA-dependent RNA polymerase (replicase; RdRp; nsP1-4) promoter located just upstream of the sequence of interest. Illustrative RdRp promoters include 26S promoters derived from Alphaviruses. However, any RdRp promoter that functions to produce the 3' sub-genomic RNA species from the RNA replicons described herein is contemplated for use in the chimeric vectors, such as RdRp promoters derived from norovirus, polio virus, flaviviruses, etc. recognized by the replicase used in the replicon.

In lieu of an RdRp promoter, in certain embodiments, an internal ribosome entry site (IRES) element may be included to allow for translation of the sequence of interest directly from the full length RNA produced from the replicon. In other embodiments, a viral 2A element can be included to allow for separate expression of various proteins from the same promoter. IRES elements and 2A elements are known in the art (U.S. Pat. No. 4,937,190; de Felipe et al. 2004. Traffic 5: 616-626).

The RNA replicon sequence, for those embodiments requiring reverse transcription, once reverse transcribed, does require a promoter. This promoter is typically located between the 5'LTR and the 3' LTR sequences, and further upstream of the RNA replicon 5'UTR (see e.g., FIG. 2B). An "internal" promoter/enhancer is one that is located between the 5' LTR and the 3' LTR sequences in the viral vector construct and is operably linked to the RNA replicon sequence. The internal promoter/enhancer may be any promoter, enhancer or promoter/enhancer combination known to increase expression of a gene (e.g. the RNA replicon sequence) with which it is in a functional relationship. A "functional relationship" and "operably linked" mean, without limitation, that the sequence is in the correct location and orientation with respect to the promoter and/or enhancer that the replicon sequence including the sequence of interest will be expressed when the promoter and/or enhancer is contacted with the appropriate molecules. Additionally, promoters are used in the DNA plasmids used for production of viral particles in the packaging systems. Promoters for use in the packaging plasmids and the internal promoter/enhancers for use in the chimeric lentiviral-RNA replicon vector genome are known in the art and can be selected according to a variety of criteria known to the person of skill in the art.

The choice of an internal promoter/enhancer is based on the desired expression pattern of the RNA replicon comprising the sequence of interest and the specific properties of known promoters/enhancers. Thus, the internal promoter may be constitutively active. Non-limiting examples of constitutive promoters that may be used include the promoter for ubiquitin (U.S. Pat. No. 5,510,474; WO 98/32869), CMV (Thomsen et al., PNAS 81:659, 1984; U.S. Pat. No. 5,168,062), beta-actin (Gunning et al. 1989 Proc. Natl. Acad. Sci. USA 84:4831-4835) and pgk (see, for example, Adra et al. 1987 Gene 60:65-74; Singer-Sam et al. 1984 Gene 32:409-417; and Dobson et al. 1982 Nucleic Acids Res. 10:2635-2637).

Alternatively, the promoter may be a tissue specific promoter. In some preferred embodiments, the promoter is a target cell-specific promoter. For example, the promoter can be from any product expressed by dendritic cells, including CD11c, CD103, TLRs, DC-SIGN, BDCA-3, DEC-205, DCIR2, mannose receptor, Dectin-1, Clec9A, MHC Class II. In addition, promoters may be selected to allow for inducible expression of the RNA replicon comprising the sequence of interest. A number of systems for inducible expression are known in the art, including the tetracycline responsive system, the lac operator-repressor system, as well as promoters responsive to a variety of environmental or physiological changes, including heat shock, metal ions, such as metallothionein promoter, interferons, hypoxia, steroids, such as progesterone or glucocorticoid receptor promoter, radiation, such as VEGF promoter. A combination of promoters may also be used to obtain the desired expression of the RNA replicon. The artisan of ordinary skill will be able to select a promoter based on the desired expression pattern of the gene in the organism or the target cell of interest.

The viral genome may comprise at least one RNA Polymerase II or III responsive promoter. This promoter can be operably linked to the RNA replicon comprising the sequence of interest and can also be linked to a termination sequence. In addition, more than one RNA Polymerase II or III promoters may be incorporated. RNA polymerase II and III promoters are well known to one of skill in the art. A suitable range of RNA polymerase III promoters can be found, for example, in Paule and White, Nucleic Acids Research, Vol. 28, pp 1283-1298 (2000). RNA polymerase II or III promoters also include any synthetic or engineered DNA fragment that can direct RNA polymerase II or III to transcribe downstream RNA coding sequences. Further, the RNA polymerase II or III (Pol II or III) promoter or promoters used as part of the viral vector genome can be inducible. Any suitable inducible Pol II or III promoter can be used with the methods of the invention. Particularly suited Pol II or III promoters include the tetracycline responsive promoters provided in Ohkawa and Taira, Human Gene Therapy, Vol. 11, pp 577-585 (2000) and in Meissner et al. Nucleic Acids Research, Vol. 29, pp 1672-1682 (2001).

An internal enhancer may also be present in the viral construct to increase expression of the RNA replicon comprising a sequence of interest. For example, the CMV enhancer (Boshart et al. Cell, 41:521, 1985) may be used. Many enhancers in viral genomes, such as HIV, CMV, and in mammalian genomes have been identified and characterized (see GenBank). An enhancer can be used in combination with a heterologous promoter. One of ordinary skill in the art will be able to select the appropriate enhancer based on the desired expression pattern.

A viral vector genome will usually contain a promoter that is recognized by the target cell and that is operably linked to the RNA replicon comprising the sequence of interest, viral components, and other sequences discussed herein. A promoter is an expression control element formed by a nucleic acid sequence that permits binding of RNA polymerase and transcription to occur. Promoters may be inducible, constitutive, temporally active or tissue specific. The activity of inducible promoters is induced by the presence or absence of biotic or abiotic factors. Inducible promoters can be a useful tool in genetic engineering because the expression of genes to which they are operably linked can be turned on or off at certain stages of development of an organism, its manufacture, or in a particular tissue. Inducible promoters can be grouped as chemically-regulated promoters, and physically-regulated promoters. Typical chemically-regulated promoters include, not are not limited to, alcohol-regulated promoters (e.g., alcohol dehydrogenase I (alcA) gene promoter), tetracycline-regulated promoters (e.g., tetracycline-responsive promoter), steroid-regulated promoter (e.g., rat glucocorticoid receptor (G R)-based promoter, human estrogen receptor (ER)-based promoter, moth ecdysone receptor-based promoter, and the promoters based on the steroid/retinoid/thyroid receptor superfamily), metal-regulated promoters (e.g., metallothionein gene-based promoters), and pathogenesis-related promoters (e.g., *Arabidopsis* and maize pathogen-related (PR) protein-based promoters). Typical physically-regulated promoters include, but are not limited to, temperature-regulated promoters (e.g., heat shock promoters), and light-regulated promoters (e.g., soybean SSU promoter). Other exemplary promoters are described elsewhere, for example, in "Promoters used to regulate gene expression" on Patent Lens web site, accessed 18 May 2009.

One of skill in the art will be able to select an appropriate promoter based on the specific circumstances. Many different promoters are well known in the art, as are methods for operably linking the promoter to the gene to be expressed. Both native promoter sequences and many heterologous promoters may be used to direct expression in the packaging cell and target cell. Heterologous promoters are preferred, however, as they generally permit greater transcription and higher yields of the desired protein as compared to the native promoter. In certain embodiments, synthetic promoters may also be used.

The promoter may be obtained, for example, from the genomes of viruses such as polyoma virus, fowlpox virus, adenovirus, bovine papilloma virus, avian sarcoma virus, cytomegalovirus, a retrovirus, hepatitis-B virus and Simian Virus 40 (SV40). The promoter may also be, for example, a heterologous mammalian promoter, e.g., the actin promoter or an immunoglobulin promoter, a heat-shock promoter, or the promoter normally associated with the native sequence, provided such promoters are compatible with the target cell. In one embodiment, the promoter is the naturally occurring viral promoter in a viral expression system. In some embodiments, the promoter is a dendritic cell-specific promoter. The dendritic cell-specific promoter can be, for example, CD11c promoter.

Transcription may be increased by inserting an enhancer sequence into the vector(s). Enhancers are typically cis-acting elements of DNA, usually about 10 to 300 bp in length, that act on a promoter to increase its transcription. Many enhancer sequences are now known from mammalian genes (globin, elastase, albumin, alpha-fetoprotein, and insulin) and from eukaryotic cell viruses. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the antigen-specific polynucleotide sequence, but is preferably located at a site 5' from the promoter.

Expression vectors may also contain sequences necessary for the termination of transcription and for stabilizing the mRNA. These sequences are often found in the 5' and, occasionally 3', untranslated regions of eukaryotic or viral DNAs or cDNAs and are well known in the art.

The viral vector genome may also contain additional genetic elements. The types of elements that may be included in the construct are not limited in any way and may be chosen to achieve a particular result. For example, a signal that facilitates nuclear entry of the viral genome in the target cell may be included. An example of such a signal is the HIV-1 cPPT/CTS (DNA flap) signal. In additional embodiments, the viral vector genome may comprise a rev responsive element (RRE). Further, elements may be included that facilitate the characterization of the provirus integration site in the target cell. For example, a tRNA amber suppressor sequence may be included in the construct. An insulator sequence from e.g., chicken β-globin may also be included in the viral genome construct. This element reduces the chance of silencing an integrated provirus in the target cell due to methylation and heterochromatinization effects. In addition, the insulator may shield the internal enhancer, promoter and exogenous gene from positive or negative positional effects from surrounding DNA at the integration site on the chromosome. In addition, the vector genome may contain one or more genetic elements designed to enhance expression of the RNA replicon comprising the gene of interest. For example, a woodchuck hepatitis virus responsive element (WRE) may be placed into the construct (Zufferey et al. 1999. J. Virol. 74:3668-3681; Deglon et al. 2000. Hum. Gene Ther. 11:179-190).

The viral vector genome is typically constructed in a plasmid form that may be transfected into a packaging or producer cell line. The plasmid generally comprises sequences useful for replication of the plasmid in bacteria. Such plasmids are well known in the art. In addition, vectors that include a prokaryotic origin of replication may also include a gene whose expression confers a detectable or selectable marker such as a drug resistance. Typical bacterial drug resistance products are those that confer resistance to ampicillin or tetracycline.

Plasmids containing one or more of the components described herein are readily constructed using standard techniques well known in the art. For analysis to confirm correct sequences in plasmids constructed, the plasmid may be replicated in *E. coli*, purified, and analyzed by restriction endonuclease digestion or its DNA sequence determined by conventional methods.

Vectors constructed for transient expression in mammalian cells may also be used. Transient expression involves the use of an expression vector that is able to replicate efficiently in a host cell, such that the host cell accumulates many copies of the expression vector and, in turn, synthesizes high levels of a the polypeptide encoded by the antigen-specific polynucleotide in the expression vector. See Sambrook et al., supra, pp. 16.17-16.22. Other vectors and methods suitable for adaptation to the expression of polypeptides are well known in the art and are readily adapted to the specific circumstances.

Using the teachings provided herein, one of skill in the art will recognize that the efficacy of a particular expression system can be tested by transfecting packaging cells with a vector comprising a gene encoding a reporter protein and measuring the expression using a suitable technique, for example, measuring fluorescence from a green fluorescent protein conjugate. Suitable reporter genes are well known in the art.

3. Viral Replicon Sequences

Figure 1A:
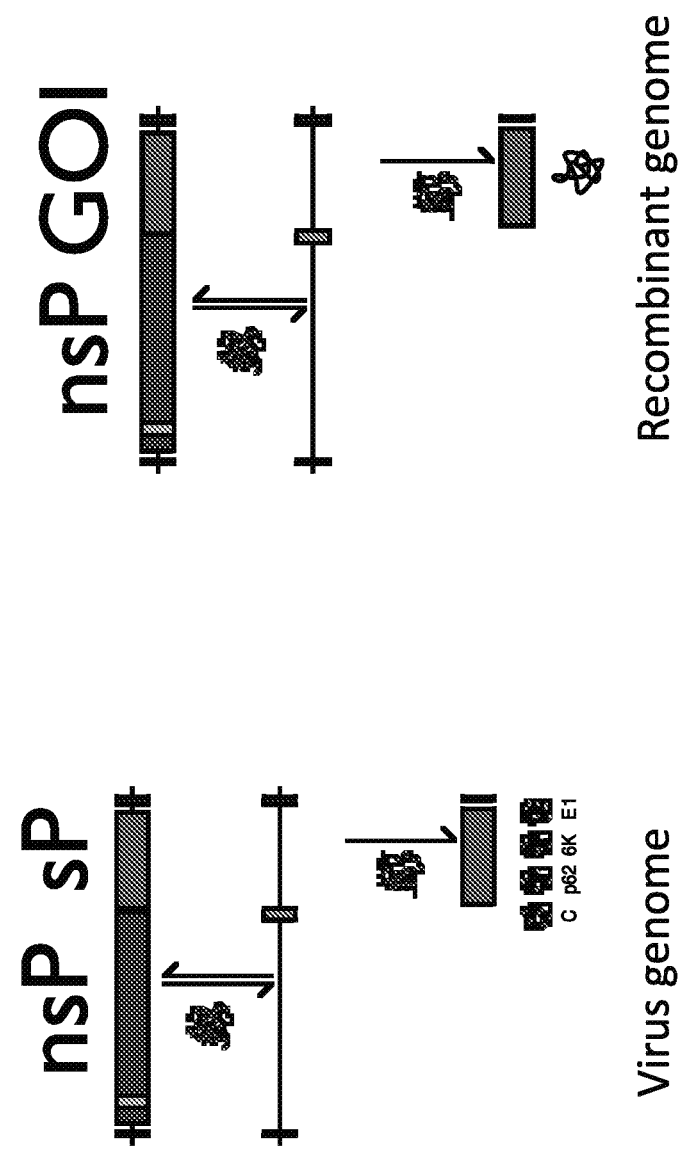
FIG. 1A is a diagram depicting alphavirus RNA replication cycle. The alphaviral genome functions directly as an mRNA, is 5'-capped and 3' polyadenylated. Replication of the alphavirus self replicating RNA yields high levels of a shorter, sub-genomic RNA species derived from the 3' end of the RNA and driven from the 26S RNA dependent RNA polymerase promoter.
Figure 1B:
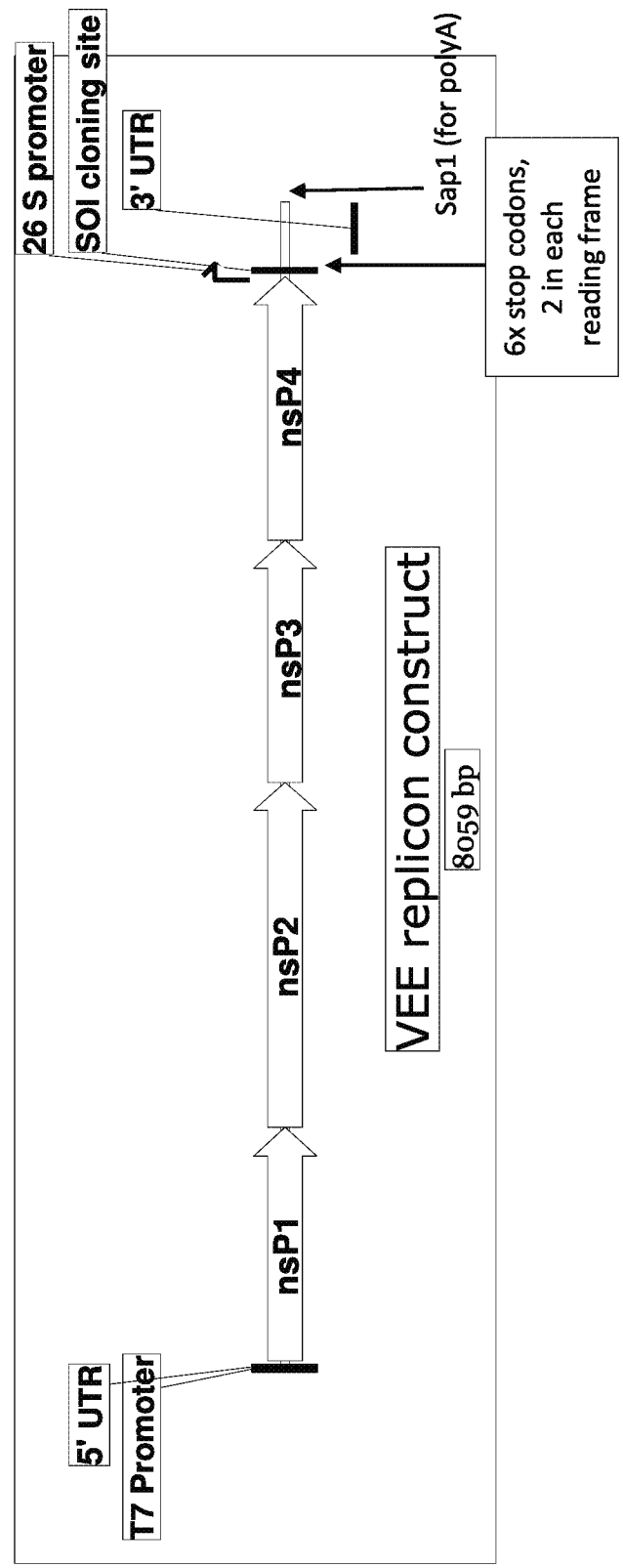
FIG. 1B is a diagram depicting an illustrative RNA replicon derived from VEE. 5' UTR, nsPs, 26S promoter, and 3' UTR sequences taken from GenBank: L01443.1, Venezuelan equine encephalitis virus strain TC-83 (attenuated). The construct was ordered from Genscript in a pUC57-Amp backbone. nsP—non-structural protein; sP—structural protein; GOI—gene of interest.

RNA replicons for use in the chimeric lentiviral vectors described herein can be derived from either positive- or negative-strand RNA viruses. RNA replicons are self replicating RNAs that are able to drive high level, cytosolic expression of recombinant sequences of interest. In certain embodiments, the viral replicon sequence is derived from an alphavirus. (See e.g., McCullough at al., Molecular Therapy—Nucleic Acids 2014 volume 3 page e173). An illustrative RNA replicon derived from Venezuelan equine encephalitis virus (VEE) is shown in FIG. 1. Other Alphavirus replicons are also contemplated herein, including, but not limited to, RNA replicons from Eastern Equine Encephalitis Virus (EEE), Venezuelan Equine Encephalitis Virus (VEE), Everglades Virus, Mucambo Virus, Ockelbo virus, Pixuna Virus, Western Equine Encephalitis Virus (WEE), Sindbis Virus, Semliki Forest Virus, Middleburg Virus, Chikungunya Virus, O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Aura virus, Babanki Virus, Kyzylagach Virus, Highlands J virus, Fort Morgan Virus, Ndumu Virus, Buggy Creek Virus and any other virus classified by the International Committee on Taxonomy of Viruses (ICTV) as an alphavirus, as well as subgroups thereof as are known in the art. Additional Alphavirus species from which RNA replicons can be used include Salmon pancreatic disease virus, Sleeping Disease virus, Southern elephant seal virus, Tonate virus. In certain embodiments, RNA replicons from an alphavirus species with attractive properties (e.g. SPDV which is adapted to very low temperatures, or others alphavirus species with high activity in insect cells and thus adapted to modest temperatures) are selected for use herein. Other RNA virus replicons are also contemplated for use herein.

An alphaviral RNA replicon generally comprises the 4 genes encoding a full-length replicase polyprotein (REP) (which is comprised of nsP1, nsP2, nsP3 and nsP4) and optionally, the alphavirus 5' and or 3' non-coding sequences (5'UTR, 3'UTR) which contain cis-acting elements including Conserved Sequence Elements (see for example, Journal of Virology, 1990, p. 1639-1647). The genes encoding the nonstructural proteins comprise sequences necessary for replication and the replicase (Rep) gene.

In certain embodiments, an alphavirus packaging signal can be included. In other embodiments, a retroviral, and in certain embodiments, a lentiviral, RNA packaging signal may be inserted into the RNA replicon such that the RNA is packaged into the retroviral/lentiviral particle in a specific manner rather than a nonspecific manner. In this regard, placement of the packaging signal is important. As has been shown previously a semliki forest virus (US20080118956) or a sindbis virus replicon (US2015050243) can be passively encapsidated into a virus particle having a retroviral envelope even when the RNA sequence does not contain a specific packaging signal. It is generally understood that the inclusion of a packaging signal results in selective encapsidation of an RNA transcript and, thus, a larger number of produced virus particles containing the RNA of interest.

It is not obvious how an alphavirus replicon genome can be engineered to successfully contain a retro or lentiviral packaging signal. While sequences can readily be inserted downstream of the sequence of interest (SOI) but upstream of the 3' replication signal (see FIG. 8A), this results in an overwhelming encapsidation of the subgenomic RNA species, which is transcribed from the 26S promoter (indicated by the curved arrow in FIG. 8). The subgenomic RNA alone is not a functional replicon since it lacks the genes for the alphavirus structural replicase proteins (REP in FIG. 8). Published US patent application US2008011895 describes a replicon with a genetically inactivated 26S promoter, which can be encapsidated into a retroviral particle without concomitant encapsidation of subgenomic RNA. However, this replicon would not be able to produce subgenomic transcripts in vector-transduced cells and, thus, would not mediate the same high SOI expression levels as a functional replicon that contains the 26S promoter. Moreover, this publication does not propose a solution for where a packaging signal can be inserted. Published US patent application US2015050243 mentions a plasmid that is engineered to have a packaging signal from Rous Sarcoma virus downstream of the eukaryotic CMV promoter but upstream of the replicon REP sequence. Note that since an intact 5' replication signal is required for alphavirus replicon replication, this construct would not result in a functional replicon. Indeed, the sequence included in the US2015050243 publication does not contain a packaging signal (even though the text refers to it as such).

Thus, in certain embodiments, the RNA packaging signal can be inserted between the 5' replication signal and the full nsP1 coding region. In certain embodiments, the RNA packaging signal is a retroviral (e.g., lentiviral) RNA packaging signal. In additional embodiments, other cis-acting sequences can be included to improve packaging of the RNA replicon genome. In certain embodiments, the packaging signal includes the entire core encapsidation signal which includes the psi and DIS sequences (see Moore, & Hu 2009 AIDS Rev 11:91-102). In certain embodiments, also included in the RNA replicon portion of the chimeric lentiviral-RNA replicon vector genomes is a polyadenylation signal. In certain embodiments, in particular in embodiments where the chimeric lentiviral-RNA replicon vector particle is reverse transcriptase independent, the RNA replicon includes a hardcoded polyA tail.

In certain embodiments, an alphavirus replicon-encoding sequence disclosed herein comprises a retroviral, such as a lentiviral (e.g., HIV), packaging signal inserted downstream of the 5' replication signal. In this regard, the replication signal spans across an untranslated region (5'UTR) and into the translated region of the nsP1 gene of the replicase polyprotein up to and including the conserved sequence element (CSE). Alphavirus conserved sequence elements are known in the art and readily identified by the person of skill art (see e.g., Niesters and Strauss 1990 J Virol 64:1639). Exemplary CSE are disclosed herein for example at positions 133-183 of SEQ ID NO: 2 and 3. The complete replication signal length varies across the alphavirus genus. However, it is well accepted that the key elements are the 5'UTR and the CSE that forms an RNA stem loop structure and is important for alphavirus replication (see e.g., Niesters and Strauss 1990 J Virol 64:1639). From the beginning of nsP1 to the end of the CSE is approximately 141 nucleotides, encoding about 47 amino acids of the nsP1 protein. The 5'UTR and the CSE are sensitive to mutations. In the chimeric vectors described herein, the part of the replication signal sequence encoding the beginning of the replicase protein is duplicated so as to serve as part of the intact replication signal as well as the in frame coding for the 5' end of nsP1, while having the RNA packaging signal inserted between: Therefore, the first approximately ~141 nucleotide region serves as the necessary end of the replication signal on the 5' side of the RNA packaging signal, and the second ~141 nucleotides follows an IRES or 2A cleavage site and serves as the in frame nsP1 coding sequence (see FIGS. 8 B-E). In other words, in order to allow for a continuous 5' replication signal and also translation of a full length, functional replicase (including full-length nsP1), the polynucleotide sequence encoding the first amino acids of the nsP1 up through the CSE is included in frame with the rest of the replicase-encoding gene, downstream of the inserted packaging signal, and preceded by an internal ribosome entry site (IRES) or 2A cleavage site. This sequence may be codon modified to abrogate formation of the CSE RNA secondary structure and/or to minimize recombination with the duplicate sequence that serves as the end of the replication signal. Such modifications are known in the art. Exemplary codon modifications are shown in SEQ ID Nos: 2 and 3 herein but other similar such modifications could be made by the person of skill in the art. The section of the coding region of the replicase that occurs upstream of the RNA packaging signal and IRES (and which contains the 3'end of the replication signal) can be as long as desired so long as the complete functional replication signal is included. In other words, the RNA packaging signal can be positioned anywhere in between the end of the 5' replication signal and the beginning of the 26S promoter, as long as it is followed by a full-length replicase-encoding gene.

In certain embodiments, a hepatitis delta virus ribozyme is included at the 3' end following the poly-A stretch. This acts to process the RNA transcripts to unit lengths in a self-cleavage reaction, the end result being an RNA with a clean poly-A stretch end.

In another embodiment, translation of the replicase in achieved through a 2A endoprotease cleavage immediately at the beginning of the replicase (see e.g., FIG. 8D). This requires translational read-through from the 5' end of the transcript, which is achieved by site-directed mutations that remove (mutate) stop codons in the sequence upstream of the replicase gene. As would be understood by the skilled person, the codons are not generally "removed" but are mutated to code for something other than a stop codon.

In another embodiment the packaging signal is inserted in between the nsP3 and nsP4 genes. The alphavirus replicase is translated as an nsP1-3 polyprotein called P123. During normal translation, an arginine residue is incorporated at low frequency at the site of an opal stop codon, which thus results in translational read-through. This leads to a P1234 polyprotein, which subsequently is proteolytically cleaved at a site six amino acids downstream of the opal/arginine to produce mature nsP4 protein (see FIG. 8F). In the construct shown in FIG. 8G, a lentiviral packaging signal and an IRES sequence are inserted in between the nsP3 and nsP4 genes, flanked on both ends by a motif for proteolytic cleavage recognition. An exemplary cleavage recognition motif is set forth in SEQ ID NO:4. Variants thereof may be present across the alphavirus genus. However, such motifs and variants thereof would be readily recognized by the person of ordinary skill in the art. A similar approach has been described by Tamberg et al (J. Gen. Virol. 2007, doi: 10.1099/vir.0.82436-0) for inserting a GFP gene in between nsP3 and nsP4 of Semliki Forest virus, albeit without the IRES. In a similar example shown in FIG. 8G, a short PSI mutated not to encode a stop codon is used by itself without an IRES but flanked on both ends by the proteolytic cleavage recognition motif.

The present chimeric lentiviral-RNA replicon vector particles comprise a sequence of interest (SOI). The sequence of interest (SOI) is typically inserted in place of Alphavirus structural protein genes (see e.g., FIG. 1 and FIG. 2 indicating SOI/GOI downstream of either NSP4 or REP).

4. Sequences of Interest (SOI)

The sequence of interest is not limited in any way and includes any nucleic acid that one of ordinary skill desires to have transcribed, and expressed in the target cell. The product can be a protein or a nucleic acid. The sequence of interest can encode a protein or a nucleic acid molecule, including siRNA, microRNA, a self-complementary double stranded RNA in which the complementary region is greater than about 20 ribonucleotides in length, or an RNA that is complementary to a message RNA, where binding of said complementary (anti-sense) RNA to the message RNA blocks its ability to be translated into protein.

In some instances, the sequence of interest can encode an antigen against which an immune response is desired. In particular, tumor antigens and infectious disease antigens from agents such as HIV, RSV, HBV, HSV, HCV, HPV, pertussis, *Staphylococcus aureus*, malaria, or tuberculosis are desirable. Antigens associated with many diseases and disorders are well known in the art. An antigen may be previously known to be associated with the disease or disorder, or may be identified by any method known in the art. For example, an antigen to a type of cancer from which a patient is suffering may be known, such as a tumor-associated antigen or may be identified from the tumor itself by any of a variety of methods known in the art.

Tumor-associated antigens are known for a variety of cancers including, for example, sarcomas, renal cell carcinoma, prostate cancer, melanoma, and breast cancer. In some breast cancers, for example, the Her-2 receptor is overexpressed on the surface of cancerous cells. Exemplary tumor antigens include, but are not limited to, MAGE, BAGE, RAGE, and NY-ESO-1, which are unmutated antigens expressed in the immune-privileged areas of the testes and in a variety of tumor cells; lineage-specific tumor antigens such as the melanocyte-melanoma lineage antigens MART-1/Melan-A, gp100, gp75, mda-7, tyrosinase and tyrosinase-related protein, renal cell carcinoma—5T4, SM22-alpha, carbonic anhydrases I and IX (also known as G250), hypoxia-inducible factors (e.g., HIF-1alpha and HIF-2alpha), VEGF or prostate specific membrane antigen (PSMA), prostate-specific antigen (PSA), prostatic acid phosphates, and six-transmembrane epoithelial antigen of the prostate (STEAP), NKX3.1, which are antigens expressed in normal and neoplastic cells derived from the same tissue; epitope proteins/peptides derived from genes mutated in tumor cells or genes transcribed at different levels in tumor compared to normal cells, such as telomerase enzyme, survivin, mesothelin, SSX2 (HOM-MEL-40 tumor antigen), mutated ras, bcr/abl rearrangement, Her2/neu, EGF receptor (including EGFRviii mutation), mutated or wild-type p53, cytochrome P450 1B1, and abnormally expressed intron sequences such as N-acetylglucosaminyl-transferase-V; clonal rearrangements of immunoglobulin genes generating unique idiotypes in myeloma and B-cell lymphomas; epitope proteins/peptides derived from onco-viral processes, such as human papilloma virus proteins E6 and E7; nonmutated oncofetal proteins with a tumor-selective expression, such as carcinoembryonic antigen and alpha-fetoprotein. Also contemplated as a tumor associated antigen is the embryonic transcription factor Brachyury (see e.g., Roselli et al., Clin Cancer Res. 2012 Jul. 15; 18(14): 3868-79; Hamilton et al., Semin Oncol. 2012 June; 39(3): 358-66; Palena et al., J Natl Cancer Inst. 2014 May 9; 106(5)). A number of tumor associated antigens have been reviewed (see, for example, "Tumor-Antigens Recognized By T-Lymphocytes," Boon T, Cerottini J C, Vandeneynde B, Vanderbruggen P, Vanpel A, Annual Review Of Immunology 12: 337-365, 1994; "A listing of human tumor antigens recognized by T cells," Renkvist N, Castelli C, Robbins P F, Parmiani G. Cancer Immunology Immunotherapy 50: (1) 3-15 Mar. 2001).

The antigen can also be an antigen associated with an infectious disease, such as, for example, HIV/AIDS. The antigen can be, for example, gp120 (Klimstra, W. B., et al. 2003. J Virol 77:12022-12032; Bernard, K. A., et al. 2000. Virology 276:93-103; Byrnes, A. P., et al. 1998. J Virol 72: 7349-7356). Other exemplary antigens include, but are not limited to: gag, pol, env, tat, nef and rev (Lieberman, J. et al. 1997. AIDS Res Hum Retroviruses 13(5): 383-392; Menendez-Arias, L. et al. 1998. Viral Immunol 11(4): 167-181).

Examples of viral antigens include, but are not limited to, adenovirus polypeptides, alphavirus polypeptides, calicivirus polypeptides, e.g., a calicivirus capsid antigen, coronavirus polypeptides, distemper virus polypeptides, Ebola virus polypeptides, enterovirus polypeptides, flavivirus polypeptides, hepatitis virus (AE) polypeptides, e.g., a hepatitis B core or surface antigen, or a hepatitis C virus E1 or E2 glycoproteins, core, or non-structural proteins, herpes-virus polypeptides, e.g., a herpes simplex virus or varicella zoster virus glycoprotein, immunodeficiency virus polypeptides, e.g., the human immunodeficiency virus envelope or protease, infectious peritonitis virus polypeptides, influenza virus polypeptides, e.g., an influenza A hemagglutinin, neuraminidase, or nucleoprotein, leukemia virus polypeptides, Marburg virus polypeptides, orthomyxovirus polypeptides, papilloma virus polypeptides, parainfluenza virus polypeptides, e.g., the hemagglutinin/neuraminidase, paramyxovirus polypeptides, parvovirus polypeptides, pestivirus polypeptides, picoma virus polypeptides, e.g., a poliovirus capsid polypeptide, pox virus polypeptides, e.g., a vaccinia virus polypeptide, rabies virus polypeptides, e.g., a rabies virus glycoprotein G, reovirus polypeptides, retrovirus polypeptides, and rotavirus polypeptides.

Examples of bacterial antigens include, but are not limited to, *Actinomyces* polypeptides, *Bacillus* polypeptides, *Bacteroides* polypeptides, *Bordetella* polypeptides, *Bartonella* polypeptides, *Borrelia* polypeptides, e.g., *B. burgdorferi* OspA, *Brucella* polypeptides, *Campylobacter* polypeptides, Capnocytophaga polypeptides, *Chlamydia* polypeptides, *Clostridium* polypeptides, *Corynebacterium* polypeptides, *Coxiella* polypeptides, Dermatophilus polypeptides, *Enterococcus* polypeptides, *Ehrlichia* polypeptides, *Escherichia* polypeptides, *Francisella* polypeptides, *Fusobacterium* polypeptides, Haemobartonella polypeptides, *Haemophilus* polypeptides, e.g., *H. influenzae* type b outer membrane protein, *Helicobacter* polypeptides, *Klebsiella* polypeptides, L-form bacteria polypeptides, Leptospira polypeptides, *Listeria* polypeptides, Mycobacteria polypeptides, *Mycoplasma* polypeptides, *Neisseria* polypeptides, *Neorickettsia* polypeptides, *Nocardia* polypeptides, *Pasteurella* polypeptides, Peptococcus polypeptides, *Peptostreptococcus* polypeptides, Pneumococcus polypeptides, *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, *Streptococcus* polypeptides, e.g., *S. pyogenes* M proteins, *Treponema* polypeptides, and *Yersinia* polypeptides, e.g., *Y. pestis* F1 and V antigens.

Examples of fungal antigens include, but are not limited to, *Absidia* polypeptides, *Acremonium* polypeptides, *Alternaria* polypeptides, *Aspergillus* polypeptides, Basidiobolus polypeptides, *Bipolaris* polypeptides, *Blastomyces* polypeptides, *Candida* polypeptides, *Coccidioides* polypeptides, Conidiobolus polypeptides, *Cryptococcus* polypeptides, Curvalaria polypeptides, *Epidermophyton* polypeptides, *Exophiala* polypeptides, *Geotrichum* polypeptides, *Histoplasma* polypeptides, Madurella polypeptides, *Malassezia* polypeptides, *Microsporum* polypeptides, Moniliella polypeptides, *Mortierella* polypeptides, *Mucor* polypeptides, *Paecilomyces* polypeptides, *Penicillium* polypeptides, Phialemonium polypeptides, *Phialophora* polypeptides, Prototheca polypeptides, Pseudallescheria polypeptides, Pseudomicrodochium polypeptides, *Pythium* polypeptides, *Rhinosporidium* polypeptides, *Rhizopus* polypeptides, Scolecobasidium polypeptides, *Sporothrix* polypeptides, *Stemphylium* polypeptides, *Trichophyton* polypeptides, *Trichosporon* polypeptides, and Xylohypha polypeptides.

Examples of protozoan parasite antigens include, but are not limited to, *Babesia* polypeptides, *Balantidium* polypeptides, *Besnoitia* polypeptides, *Cryptosporidium* polypeptides, *Eimeria* polypeptides, Encephalitozoon polypeptides, *Entamoeba* polypeptides, Giardia polypeptides, Hammondia polypeptides, *Hepatozoon* polypeptides, *Isospora* polypeptides, *Leishmania* polypeptides, Microsporidia polypeptides, *Neospora* polypeptides, *Nosema* polypeptides, Pentatrichomonas polypeptides, *Plasmodium* polypeptides, e.g., *P. falciparum* circumsporozoite (PfCSP), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of helminth parasite antigens include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides.

Examples of ectoparasite antigens include, but are not limited to, polypeptides (including protective antigens as well as allergens) from fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs.

Once an antigen has been identified and selected, a sequence that encodes the desired antigen is identified. In certain embodiments, the sequence comprises a cDNA.

In certain cases, the sequence of interest can be a gene encoding a small inhibiting RNA (siRNA) or a microRNA (miRNA) of interest that down-regulates expression of a molecule. For example, the gene encoding an siRNA or a microRNA can be used to down-regulate expression of negative regulators in a cell, including those that inhibit activation or maturation of dendritic cells. siRNAs and microRNAs are well known in the art (Fire et al., Nature 391:806, 1998; see also "The RNA Interference Resource" of Applied Biosystems, Trang et al., Oncogene Suppl 2:S52, 2008; Taganov, K., et al. 2007. Immunity 26:133-137; Dahlberg, J. E. and E. Lund. 2007. Sci. STKE 387:pe25; Tiemann and Rossi, EMBO Mol Med 1: 142, 2009). Alternatively, the sequence of interest can encode a self-complementary double stranded RNA in which the complementary region is greater than about 20 ribonucleotides in length, or an anti-sense RNA that is greater than about 20 ribonucleotides in length. Those of ordinary skill in the art will appreciate that siRNA, miRNA, dsRNA and anti-sense RNA molecules can be expressed from an RNA polymerase III promoter, or, alternatively, can be a component of a non-coding RNA that is transcribed from an RNA polymerase II promoter.

In addition, the sequence of interest may encode more than one product. In some configurations, the sequence to be delivered can comprise multiple genes encoding at least one protein, at least one siRNA, at least one microRNA, at least one dsRNA or at least one anti-sense RNA molecule or any combinations thereof. For example, the sequence to be delivered can include one or more nucleic acids that encode one or more antigens against which an immune response is desired. The one or more antigens can be associated with a single disease or disorder, or they can be associated with multiple diseases and/or disorders. In certain embodiments, the SOI comprises a sequence encoding an immunomodulatory protein. In some instances, a sequence encoding an immunomodulatory protein can be included along with a sequence encoding an antigen against which an immune response is desired, and the combination can elicit and regulate the immune response to the desired direction and magnitude. In other instances, a sequence encoding an siRNA, microRNA, dsRNA or anti-sense RNA molecule can be constructed with a gene encoding an antigen against which an immune response is desired, and the combination can regulate the scope of the immune response. The products may be produced as an initial fusion product in which the encoding sequence is in functional relationship with one promoter. Alternatively, the products may be separately encoded and each encoding sequence in functional relationship with a promoter. The promoters may be the same or different.

In certain configurations, vectors contain polynucleotide sequences that encode immunomodulatory molecules. Exemplary immunomodulatory molecules include any of a variety of cytokines. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1 through IL-36, including, IL-1, IL-1alpha, IL-2, IL-3, IL-4, IL-5, IL-6, IL-7, IL-8, IL-9, IL-10, IL-11, IL-12; IL-15, IL-18, IL-21, IL-23, IL-27, TNF; and other polypeptide factors including LIF and kit ligand (KL). Other immunomodulatory molecules contemplated for use herein include IRF3, B7.1, B7.2, 4-1BB, CD40 ligand (CD40L), drug-inducible CD40 (iCD40), and the like. In certain embodiments, these polynucleotides are typically under the control of one or more regulatory elements that direct the expression of the coding sequences in dendritic cells.

In certain embodiments, the immunomodulatory molecule encoded by the chimeric vectors described herein is a checkpoint inhibitor molecule. Immune checkpoints refer to a variety of inhibitory pathways of the immune system that are crucial for maintaining self-tolerance and for modulating the duration and amplitude of an immune responses. Tumors use certain immune-checkpoint pathways as a major mechanism of immune resistance, particularly against T cells that are specific for tumor antigens. (see, e.g., Pardoll, 2012 Nature 12:252; Chen and Mellman 2013 Immunity 39:1). The present disclosure provides vectors encoding immune checkpoint inhibitors. Immune checkpoint inhibitors include any agent that blocks or inhibits in a statistically significant manner, the inhibitory pathways of the immune system. Such inhibitors may include antibodies, or antigen binding fragments thereof, that bind to and block or inhibit immune checkpoint receptors or antibodies that bind to and block or inhibit immune checkpoint receptor ligands. Illustrative immune checkpoint molecules that may be targeted for blocking or inhibition include, but are not limited to, CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, γδ, and memory CD8$^+$ (αβ) T cells), CD160 (also referred to as BY55) and CGEN-15049. Immune checkpoint inhibitors include antibodies, or antigen binding fragments thereof, or other binding proteins, that bind to and block or inhibit the activity of one or more of CTLA-4, PDL1, PDL2, PD1, B7-H3, B7-H4, BTLA, HVEM, TIM3, GAL9, LAG3, TIM3, B7H3, B7H4, VISTA, KIR, 2B4, CD160 and CGEN-15049. Illustrative immune checkpoint inhibitors include Tremelimumab (CTLA-4 blocking antibody), anti-OX40, PD-L1 monoclonal Antibody (Anti-67-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor).

A sequence encoding a detectable product, usually a protein, can be included to allow for identification of cells that are expressing the desired product. For example, a fluorescent marker protein, such as green fluorescent protein (GFP), is incorporated into the construct along with a sequence of interest (e.g., encoding an antigen). In other cases, the protein may be detectable by an antibody or the protein may be an enzyme that acts on a substrate to yield a detectable product, or a product that allows selection of a transfected or transduced target cell, for example confers drug resistance, such as hygromycin resistance. Typical selection genes encode proteins that confer resistance to antibiotics or other toxins suitable for use in eukaryotic cells, e.g., neomycin, methotrexate, blasticidine, among others known in the art, or complement auxotrophic deficiencies, or supply critical nutrients withheld from the media. The selectable marker can optionally be present on a separate plasmid and introduced by co-transfection.

One or more multicistronic expression units may be utilized that include two or more of the elements (e.g., sequence(s) of interest, the envelope) necessary for production of the desired virus in packaging cells. In certain embodiments, a multicistronic expression unit may be included in the viral vector genome. The use of multicistronic vectors reduces the total number of nucleic acid molecules required and thus avoids the possible difficulties associated with coordinating expression from multiple vector genomes. In a multicistronic vector the various elements to be expressed are operably linked to one or more promoters (and other expression control elements as necessary). In some configurations, a multicistronic vector comprises a sequence of interest, a sequence encoding a reporter product, and viral elements. The sequence of interest typically encodes an antigen, an immunomodulatory molecule, or a combination of one or more antigens and one or more immunomodulatory molecules. At times, the multicistronic vector comprises a gene encoding an antigen, a gene encoding an immunomodulatory molecule.

Each component to be expressed in a multicistronic expression vector may be separated, for example, by an internal ribosome entry site (IRES) element or a viral 2A element, to allow for separate expression of the various proteins from the same promoter. IRES elements and 2A elements are known in the art (U.S. Pat. No. 4,937,190; de Felipe et al. 2004. Traffic 5: 616-626). In one embodiment, oligonucleotides encoding furin cleavage site sequences (RAKR) (Fang et al. 2005. Nat. Biotech 23: 584-590) linked with 2A-like sequences from foot-and-mouth diseases virus (FMDV), equine rhinitis A virus (ERAV), and thosea asigna virus (TaV) (Szymczak et al. 2004. Nat. Biotechnol. 22: 589-594) are used to separate genetic elements in a multicistronic vector. The efficacy of a particular multicistronic vector can readily be tested by detecting expression of each of the genes using standard protocols.

In a specific exemplification, the viral vector genome comprises: a cytomegalovirus (CMV) enhancer/promoter sequence; the R and U5 sequences from the HIV 5' LTR; a packaging sequence 4); an RRE, the HIV-1 cPPT/CTS (DNA flap) signal; an internal enhancer; an internal promoter; a gene of interest expressed from the RNA replicon; the woodchuck hepatitis virus responsive element; a tRNA amber suppressor sequence; a U3 element with a deletion of its enhancer sequence; the chicken β-globin insulator; and the R and U5 sequences of the 3' HIV LTR. In some exemplifications, the vector genome comprises an intact lentiviral 5' LTR and a self-inactivating 3' LTR. (Iwakuma et al. Virology 15:120, 1999).

Construction of the vector genome can be accomplished using any suitable genetic engineering techniques known in the art, including, without limitation, the standard techniques of restriction endonuclease digestion, ligation, transformation, plasmid purification, and DNA sequencing, for example as described in Sambrook et al. (1989. Molecular Cloning: A Laboratory Manual. Cold Spring Harbor Laboratory Press, N.Y.), Coffin et al. (Retroviruses. Cold Spring Harbor Laboratory Press, N.Y. (1997)) and "RNA Viruses: A Practical Approach" (Alan J. Cann, Ed., Oxford University Press, (2000).

B. Viral Vector Envelope

The chimeric lentiviral-RNA replicon vectors described herein are generally pseudotyped with an envelope protein from a heterologous virus. A "pseudotyped" lentivirus is a lentiviral particle having one or more envelope glycoproteins that are encoded by a virus that is distinct from the lentiviral genome. The envelope glycoprotein may be modified, mutated or engineered as described herein. In certain embodiments, the viral vectors described herein are pseudotyped with VSVg envelope glycoprotein. In other embodiments, the viral vectors may be pseudotyped with an envelope glycoprotein derived from a heterologous HIV (e.g., HIV-2) or other heterologous retrovirus such as feline immunodeficiency virus (FIV), equine infectious anemia virus, Simian Immunodeficiency Virus (SIV) or maedi/visna virus. In another embodiment, the viral vectors described herein are pseudotyped with HTLV envelope or measles envelope glycoproteins.

In certain embodiments, the chimeric vectors described herein may be pseudotyped with a targeting antibody. See for example, U.S. Pat. Nos. 9,163,248 and 8,821,856.

Illustrative examples of retroviral-derived env genes which can be employed in the invention include, but are not limited to: MLV envelopes, 10A1 envelope, BAEV, FeLV-B, RD114, SSAV, Ebola, Sendai, FPV (Fowl plague virus), and influenza virus envelopes. Similarly, genes encoding envelopes from RNA viruses (e.g., RNA virus families of Picornaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Birnaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include, FeLV, VEE, HFVW, WDSV, SFV, Rabies, ALV, BIV, BLV, EBV, CAEV, SNV, ChTLV, STLV, MPMV, SMRV, RAV, FuSV, MH2, AEV, AMV, CT10, and EIAV.

In other aspects, envelope proteins for pseudotyping the chimeric viral vectors disclosed herein include, but are not limited to any of the following virus: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 and 2 and Australian bat virus, Ephemerovirus, Vesiculovirus, Vesicular Stomatitis Virus (VSV), Herpesviruses such as Herpes simplex virus types 1 and 2, varicella zoster, cytomegalovirus, Epstein-Bar virus (EBV), human herpesviruses (HHV), human herpesvirus type 6 and 8, Human immunodeficiency virus (HIV), papilloma virus, murine gammaherpesvirus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (fflovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-CoV), West Nile virus, any encephaliltis causing virus.

In particular embodiments, the chimeric viral vectors described herein are pseudotyped with an envelope glycoprotein derived from an Arbovirus. Arthropod-borne viruses (Arboviruses) are viruses that are transmitted to a host, such as humans, horses, or birds by an infected arthropod vector such as a mosquito. Arboviruses are further divided into sub-families of viruses including alphaviruses and flaviviruses, which have a single-stranded RNA genome of positive polarity and a glycoprotein-containing envelope. For example, dengue fever virus, yellow fever virus and West Nile virus belong to the flavivirus family, and Sindbis virus, Semliki Forest virus and Venezuelan Equine Encephalitis virus, are members of the alphavirus family (Wang et al. J. Virol. 66, 4992 (1992)). The envelope of Sindbis virus includes two transmembrane glycoproteins (Mukhopadhyay et al. Nature Rev. Microbio. 3, 13 (2005)): E1, believed to be responsible for fusion, and E2, believed to be responsible for cell binding. Sindbis virus envelope glycoproteins are known to pseudotype other retroviruses, including oncoretroviruses and lentiviruses.

As discussed above, an arbovirus envelope glycoprotein can be used to pseudotype a lentiviral-based chimeric vector genome.

The envelope of Sindbis virus and other alphaviruses incorporates into the lipid bilayer of the viral particle membrane, and typically includes multiple copies of two glycoproteins, E1 and E2. Each glycoprotein has membrane-spanning regions; E2 has an about 33 residue cytoplasmic domain whereas the cytoplasmic tail of E1 is very short (about 2 residues). Both E1 and E2 have palmitic acids attached in or near the membrane-spanning regions. E2 is initially synthesized as a precursor protein that is cleaved by furin or other Ca2+-dependent serine proteinase into E2 and a small glycoprotein called E3. Located between sequences encoding E2 and E1 is a sequence encoding a protein called 6K. E3 and 6K are signal sequences which serve to translocate the E2 and E1 glycoproteins, respectively, into the membrane. In the Sindbis virus genome, the coding region for Sindbis envelope proteins includes sequence encoding E3, E2, 6K, and E1. As used herein, "envelope" of an arbovirus virus includes at least E2, and may also include E1, 6K and E3. An exemplary sequence of envelope glycoproteins of Sindbis virus, strain HR, is presented as SEQ ID No. 17 in U.S. Pat. No. 8,187,872. Sequences of envelope glycoproteins for other arboviruses can be found in e.g., GenBank. For example, sequence encoding Dengue virus glycoproteins can be found in Accession GQ252677 (among others in GenBank) and in the virus variation database at NCBI (GenBank accessions and virus variation database are incorporated by reference for envelope glycoprotein sequences) and sequence encoding Venezuelan equine encephalitis virus envelope glycoproteins in Accession NP 040824 (incorporated by reference for sequences of envelope glycoproteins).

Although the cellular receptor(s) on dendritic cells for alphaviruses, and Sindbis virus in particular, have not been definitively identified to date, one receptor appears to be DC-SIGN (Klimstra et al., J Virol 77: 12022, 2003). The use of the terms "attachment", "binding", "targeting" and the like are used interchangeably and are not meant to indicate a mechanism of the interaction between Sindbis virus envelope glycoprotein and a cellular component. DC-SIGN (Dendritic Cell Specific ICAM-3 (Intracellular Adhesion Molecules 3)-Grabbing Nonintegrin; also known as CD209) is a C-type lectin-like receptor capable of rapid binding and endocytosis of materials (Geijtenbeek, T. B., et al. Annu. Rev. Immunol. 22: 33-54, 2004). E2 appears to target virus to dendritic cells through DC-SIGN. As shown herein, cells expressing DC-SIGN are transduced by viral vector particles pseudotyped with Sindbis virus E2 better (at least 2-fold, at least 3-fold, at least 4-fold, at least 5-fold, at least 6-fold, at least 7-fold, at least 8-fold, at least 9-fold, or at least 10-fold better) than isogenic cells that don't express DC-SIGN. The mechanism of how E2 glycoprotein facilitates viral infection appears to involve DC-SIGN, possibly through direct binding to DC-SIGN or causing a change in conformation or some other mechanism. Regardless of the actual mechanism, the targeting by E2 is preferential for cells expressing DC-SIGN, namely dendritic cells.

Sindbis virus also appears to bind to cells via heparan sulfate (Klimstra et al., J Virol 72: 7357, 1998; Burmes and Griffin, J Virol 72: 7349, 1998). Because heparan sulfate and other cell surface glycosaminoglycans are found on the surface of most cell types, it is desirable to reduce interaction between heparan sulfate and Sindbis envelope glycoproteins. This can be accomplished by diminishing the binding of Sindbis virus envelope to heparan sulfate or increasing the binding, e.g., increasing avidity, of Sindbis virus envelope to dendritic cells or both. As a result, non-specific binding to other molecules, which may be expressed by other cell types and which may occur even if the envelope is specific for DC-SIGN, is reduced, and the improved specificity may serve to avoid undesired side effects, such as side effects that may reduce the desired immune response, or side effects associated with off-target transduction of other cell types. Alternatively or in addition to the advantages of relatively specific transduction of cells expressing DC-SIGN, viral particles pseudo-typed with Sindbis virus envelope E2 glycoprotein may offer other advantages over viral particles pseudo-typed with glycoproteins such as VSVG. Examples of such advantages include reduced complement-mediated lysis and/or reduced neuronal cell targeting, both of which are believed to associate with administration of VSV-G pseudo-typed viral particles.

In various exemplifications, the lentiviral vector particles specifically bind to cells expressing DC-SIGN and have reduced or abrogated binding to heparan sulfate. That is, a Sindbis virus envelope E2 glycoprotein may be modified to preferentially direct the virus to dendritic cells that express DC-SIGN relative to other cell types. Based on information obtained from structural studies and molecular modeling among other studies, variant sequences of envelope proteins, especially E2 and E1 glycoproteins, are designed and generated such that the glycoproteins maintain their functions as envelope proteins, but have the desired binding specificity, avidity, or level of binding. Candidate variant sequences may be created for each glycoprotein and assayed using the methods described below, or other methods known in the art, to identify envelope glycoproteins with the most desirable characteristics. Illustrative variant Sindbis E2 glycoproteins are described in U.S. Pat. No. 8,187,872 and are contemplated for use with the chimeric vectors herein.

Certain variant sequences of Sindbis E2 have at least one amino acid alteration at residue 160 as described in U.S. Pat. No. 8,187,872. In certain embodiments, residue 160 is deleted or changed to an amino acid other than glutamic acid. An alteration is most commonly a substitution of at least one amino acid, but alternatively can be an addition or deletion of one or more amino acids. Preferably, any additional amino acids are few in number and do not comprise an antigenic epitope (e.g., hemagglutinin tag sequence), which may compromise safety. When there are two or more alterations, they can both be of the same type (e.g., substitution) or differing types (e.g., a substitution and a deletion). Multiple alterations can be scattered or located contiguously in the protein sequence.

In the first instance, variant sequences comprise at least one amino acid alteration in the region of about residue 50 to about residue 180. Within this region are amino acids that are involved with binding to heparan sulfate. By reducing the net positive charge of E2, electrostatic interaction with heparan sulfate can be reduced, resulting in decreased binding to heparan sulfate. Candidate positively charged amino acids in this region include lysines at residues 63, 70, 76, 84, 97, 104, 129, 131, 133, 139, 148, 149, 159 and arginine at residues 65, 92, 128, 137, 157, 170, 172 (Bear et al., Virology 347: 183-190, 2006). At least several of these amino acids are directly implicated in E2 binding to heparan sulfate. Net positive charge can be reduced by deletion of lysine or arginine or substitution of lysine or arginine with a neutral or negatively charged amino acid. For example, one or more of these lysines and arginines may be replaced with glutamic or aspartic acid. Certain embodiments have at least one substitution of lysine 70, 76 or 159. In cases where E2 is expressed as a polyprotein with E3, the lysine located adjacent to the natural E3/E2 cleavage site is maintained— that is, the recognition sequence and cleavage site is unaltered. Alternatively, the native endopeptidase cleavage site sequence is replaced with a recognition sequence for a different endopeptidase.

Certain variants of E2 are also modified in a way that positively impacts binding to dendritic cells. Alteration of the glutamic acid found at residue 160 in the reference HR sequence can improve binding to dendritic cells (see Gardner et al., J Virol 74, 11849, 2000). Alterations, such as a deletion of residue 160 or substitution of residue 160 are found in certain variants. In particular variants, a non-charged amino acid is substituted for Glu, in other variants, a non-acidic amino acid is substituted for Glu. Typically, Glu160 is replaced with one of the small or aliphatic amino acids, including glycine, alanine, valine, leucine or isoleucine.

Other variants comprise two or more amino acid alterations. Typically in these variants one of the alterations is Glu160 and the remaining alteration(s) are changes of one or more of the lysines and arginines in the region spanning residue about 50 to about 180. Certain of the variants comprise an alteration of Glu160 to a non-acidic residue or deletion and one or more alterations of lysine 70, lysine 76, or lysine 159 with a non-basic amino acid. Some specific variants comprise a Glu160 to Gly, Lys 70 to Glu, and Lys 159 to Glu; a Glu 160 to Gly, Lys 70, 76 and 159 to Glu; a deletion of Glu 160 and Lys 70 and 159 to Glu; and a deletion of Glu 160 and Lys 70, 76, and 159 to Glu.

In certain cases, E2 protein is first expressed as a polyprotein in fusion with at least E3 or in fusion with a leader sequence. Regardless of whether the leader sequence is E3 or another sequence, E2 in the viral envelope should be free of the E3 or other leader sequence. In other words, E2 is preferably not an E3/E2 fusion protein (e.g., the E3/E2 fusion protein called SVGmu). In certain embodiments, E2 is expressed as part of E3-E2-6K-E1 polyprotein. Sindbis virus naturally expresses E2 as part of a polyprotein and the junction regions for E3/E2, E2/6K, and 6K/E1 have sequences recognized and cleaved by endopeptidases. Normally, the E3/E2 junction is cleaved by furin or a furin-like serine endopeptidase between residues 65 and 66. Furin has specificity for paired arginine residues that are separated by two amino acids. To maintain E3/E2 cleavage by furin, the furin cleavage site (RSKRS) should maintain the two arginine residues with two amino acid separation and the serine residue. Alternatively, a different cleavage sequence can be used in place of the E3/E2 furin cleavage sequence or any of the other cleavage sequences. Recognition and cleavage sites can be incorporated for endopeptidases, including, without limitation, aspartic endopeptidases (e.g., cathepsin D, chymosin, HIV protease), cysteine endopeptidases (bromelains, papain, calpain), metalloendopeptidases, (e.g., collagenase, thermolysin), serine endopeptidases (e.g., chymotrypsin, factor IXa, factor X, thrombin, trypsin), streptokinases. The recognition and cleavage site sequences for these enzymes are well known.

Amino acids in E2, other than those already mentioned, may also be altered. Generally, a variant E2 sequence will have at least 80% sequence amino acid identity to the reference E2 sequence, or it may have at least 82%, at least 85%, at least 87%, at least 90%, at least 92%, at least 95%, or at least 98% sequence identity. The variant glycoprotein should exhibit biological function, such as the ability to facilitate infection of dendritic cells by a viral particle having an envelope comprising E2. Experiments have identified regions of envelope glycoproteins that appear to have an important role in various aspects of viral assembly, attachment to cell surface, and infection. When making variants, the following information can be used as guidelines. The cytoplasmic tail of E2—approximately residues 408 to 415—is important for virus assembly (West et al. J Virol 80: 4458-4468, 2006). Other regions are involved in forming secondary structure (approximately residues 33-53); and involved in transport and protein stability (approximately residues 86-119) (Navaratmarajah et al., J Virol 363: 124-147, 2007). The variant may retain hydrophobic character of a region that spans the membrane, approximately residues 370-380. The variant may retain one or both N-linked glycosylation sites residues NIT (residues 196-198) and NFT (residues 318-320) and may retain one or more of the sites that are palmitoylated (C-396, C416 and C417) (Strauss and Strauss Microbiol Rev 58, 491-562, 1994; pp. 499-509 incorporated). On the other hand, many regions of E2 may be altered without deleterious event. For example, insertions of transposons at many different locations in E2 still resulted in viable virus (Navaratmarajah, ibid).

In certain embodiments, a tag peptide may be incorporated into E3, 6K, or E1 proteins. For some purposes, a tag may be incorporated into E2, but a tag is not desirable for use in a product for administration to human patients. A tag peptide, which is a short sequence (e.g., 5-30 amino acids), can be used to facilitate detection of envelope expression and its presence in viral particles. For detection purposes, a tag sequence will typically be detectable by antibodies or chemicals. Another use for a tag is to facilitate purification of viral particles. A substrate containing a binding partner for the tag can be used to absorb virus. Elution of the virus can be accomplished by treatment with a moiety that displaces the tag from the binding partner or when the tag sequence is in linkage with a cleavable sequence, treatment with the appropriate endopeptidase will conveniently allow release of virus. (See, for example, Qiagen catalog, Factor Xa Protease System). Removal of the tag peptide is generally desirable for safety purposes of the virus particles use in animal subjects. If the tag is not removed, an immune response to the tag may occur.

Suitable tags include, without limitation, FLAG (DYKDDDDK) (U.S. Pat. No. 4,703,004), for which antibodies are commercially available, chitin binding protein, maltose binding protein, glutathione-S-transferase, poly (His) (U.S. Pat. No. 4,569,794), thioredoxin, HA (hemagglutinin)-tag, among others. Poly(His) can be adsorbed onto affinity media containing bound metal ions, e.g., nickel or cobalt, and eluted with a low pH medium.

The viral particles may be evaluated to determine the specificity of the envelope glycoprotein incorporated into the virus that targets dendritic cells. For example, a mixed population of bone marrow cells can be obtained from a subject and cultured in vitro. Alternatively, isogenic cells lines that express or don't express DC-SIGN can be obtained and used. The recombinant virus can be administered to the mixed population of bone marrow cells or isogenic cell lines, and expression of a reporter gene incorporated into the virus can be assayed in the cultured cells. Certain embodiments may employ a limiting dilution analysis, in which the mixed population of cells is split into separate parts, which are then separately incubated with decreasing amounts of virus (e.g., 2-fold, 5-fold, 10-fold less virus in each part). In some embodiments, at least about 50%, more preferably at least about 60%, 70%, 80% or 90%, still more preferably at least about 95% of infected cells in the mixed cell population are dendritic cells that express DC-SIGN. In certain embodiments, the ratio of infected dendritic cells to infected non-dendritic cells (or non DC-SIGN expressing cells) is at least about 2:1, at least about 3:1, at least about 4:1, at least about 5:1, at least about 6:1, at least about 7:1, at least about 8:1, at least about 9:1, at least about 10:1, at least about 20:1, at least about 30:1, at least about 40:1, at least about 50:1, at least about 100:1, at least about 200:1, at least about 500:1, at least about 1000:1, at least about 5000:1, at least about 10,000:1, or more. For limiting dilution, greater selectivity is typically seen at higher dilutions (i.e., lower amounts) of input virus.

Activity of pseudotyped viral particles can be determined by any of a variety of techniques. For example, a preferred method to measure infectivity efficiency (IU, infectious units) is by administering viral particles to cells and measuring expression of a product encoded in the vector genome. Any product that can be assayed may be used. One convenient type of product is a fluorescent protein, such as green fluorescent protein (GFP). GFP and assay is exemplified in the Examples, such as Example 3. Other products that can be used include proteins expressed on a cell surface (e.g., detection by antibody binding), enzymes, and the like. If the product is an antigen and cells are dendritic cells, infectivity/activity can be assessed by determining an immune response. Furthermore, it is possible to ascertain side effects in a mammal. The ability to specifically target dendritic cells can also be tested directly, for example, in cell culture as described below.

Viral particles can also be prepared and tested for their selectivity and/or their ability to facilitate penetration of the target cell membrane. Viral particles that have an envelope with unmodified glycoproteins can be used as controls for comparison. Briefly, cells expressing a receptor for an envelope glycoprotein are infected by the virus using a standard infection assay. After a specified time, for example 48 hours post-infection, cells can be collected and the percentage of cells infected by the virus can be determined by flow cytometry, for example. Selectivity can be scored by calculating the percentage of cells infected by virus. Similarly, the effect of a variant envelope glycoprotein on viral titer can be quantified by dividing the percentage of cells infected by virus comprising a variant envelope by the percentage of cells infected by virus comprising the corresponding wild type (unmodified) envelope glycoprotein. A particularly suitable variant will have the best combination of selectivity and infectious titer. Once a variant is selected, viral concentration assays may be performed to confirm that these viruses can be concentrated without compromising activity. Viral supernatants are collected and concentrated by ultracentrifugation. The titers of viruses can be determined by limited dilution of viral stock solution and infection of cells expressing the receptor for the envelope glycoprotein, measuring the expression of a product expressed by the viruses as described above.

The entry of a chimeric lentiviral vector particle into a target cell is another type of evaluation of activity. BlaM-Vpr (beta-lactamase Vpr) fusion protein has been utilized to evaluate HIV-1 viral penetration; a fusion of BlaM and a Sindbis virus envelope glycoprotein, such as E1 or an E2/E1 fusion protein can be used to assess the efficacy of an envelope protein in facilitating fusion and penetration into a target cell. Viral particles may be prepared, for example, by transient transfection of or other stable genetic modification of packaging cells with one or more vectors comprising the viral elements, BlaM-Vpr, and the variant envelope of interest (and an affinity molecule if appropriate). The resulting viruses can be used to infect cells expressing a molecule the targeting molecule (or affinity molecule) specifically binds in the absence or presence of the free inhibitor of binding (such as an antibody). Cells can then be washed with $CO_2$-independent medium and loaded with CCF2 dye (Aurora Bioscience). After incubation at room temperature to allow completion of the cleavage reaction, the cells can be fixed by paraformaldehyde and analyzed by flow cytometry and microscopy. The presence of blue cells indicates the penetration of viruses into the cytoplasm; fewer blue cells would be expected when blocking antibody is added (Cavrois et al. Nat Biotechnol 20: 1151-1154, 2002).

To investigate whether penetration is dependent upon a low pH, and to identify envelope glycoproteins with the desired pH dependence, $NH_4Cl$ or other compound that alters pH can be added at the infection step ($NH_4Cl$ will neutralize the acidic compartments of endosomes). In the case of $NH_4Cl$, the disappearance of blue cells will indicate that penetration of viruses is low pH-dependent. In addition, to confirm that the activity is pH-dependent, lysosomotropic agents, such as ammonium chloride, chloroquine, concanamycin, bafilomycin Al, monensin, nigericin, etc., may be added into the incubation buffer. These agents elevate the pH within the endosomal compartments (e.g., Drose and Altendorf, J. Exp. Biol. 200, 1-8, 1997). The inhibitory effect of these agents will reveal the role of pH for viral fusion and entry. The different entry kinetics between viruses displaying different fusogenic molecules may be compared and the most suitable selected for a particular application.

PCR-based entry assays can be utilized to monitor reverse transcription and measure kinetics of viral DNA synthesis as an indication of the kinetics of viral entry. For example, viral particles comprising a particular envelope protein molecule are incubated with target cells, such as 293T cells, DCs, or any other cells that have been engineered to express, or which naturally express, the appropriate binding partner (receptor) for the envelope protein molecule. Either immediately, or after a time increment (to allow infection to occur), unbound viruses are removed and aliquots of the cells are analyzed for viral nucleic acids. DNA is extracted from these aliquots and subjected to amplification analysis, generally in a semi-quantitative assay, primed with LTR-specific primers. The appearance of LTR-specific DNA products indicates the success of viral entry.

C. Production of Viral Particles

Any of a variety of methods already known in the art may be used to produce infectious chimeric lentiviral-RNA replicon vector particles whose genome comprises an RNA copy of the chimeric viral vector genome. For the sake of simplicity, a chimeric lentiviral-RNA replicon vector particle can be referred to herein as a “viral particle”, “chimeric viral particle” or “chimeric lentiviral particle” or “chimeric particle”. In one method, the viral vector genome is introduced into a packaging cell line that contains all the components necessary to package viral genomic RNA, transcribed from the viral vector genome, into viral particles. Alternatively, the viral vector genome may comprise one or more genes encoding viral components in addition to the one or more sequences of interest. In order to prevent replication of the chimeric virus in the target cell, however, endogenous viral genes required for replication will usually be removed and provided separately only in the packaging cell line. In this regard, the viral vectors are replication incompetent. Thus, as would be understood by the skilled person, replication incompetent chimeric viral vectors are vectors in which the coding regions for the genes necessary for additional rounds of vector replication and packaging are replaced with other genes, or are deleted. Such genes necessary for producing the particles are provided in trans in the packaging system. These vectors therefore are capable of infecting their target cells and delivering and expressing their viral payload (e.g., a self-replicating RNA replicon that expresses a sequence of interest at high levels), but then are unable to replicate in such a way as to package a further round of infectious viral particles. For the sake of clarity, the self-replicating RNA replicon (the "transgene" in the chimeric viral vectors described herein) functions (i.e., replicates) once delivered to a target cell by the chimeric viral vector, but the chimeric viral particle itself cannot support a further round of replication (there is no gag or envelope or other structural proteins available to support the replication). In this manner, the chimeric vector particles are replication incompetent.

Figure 4:
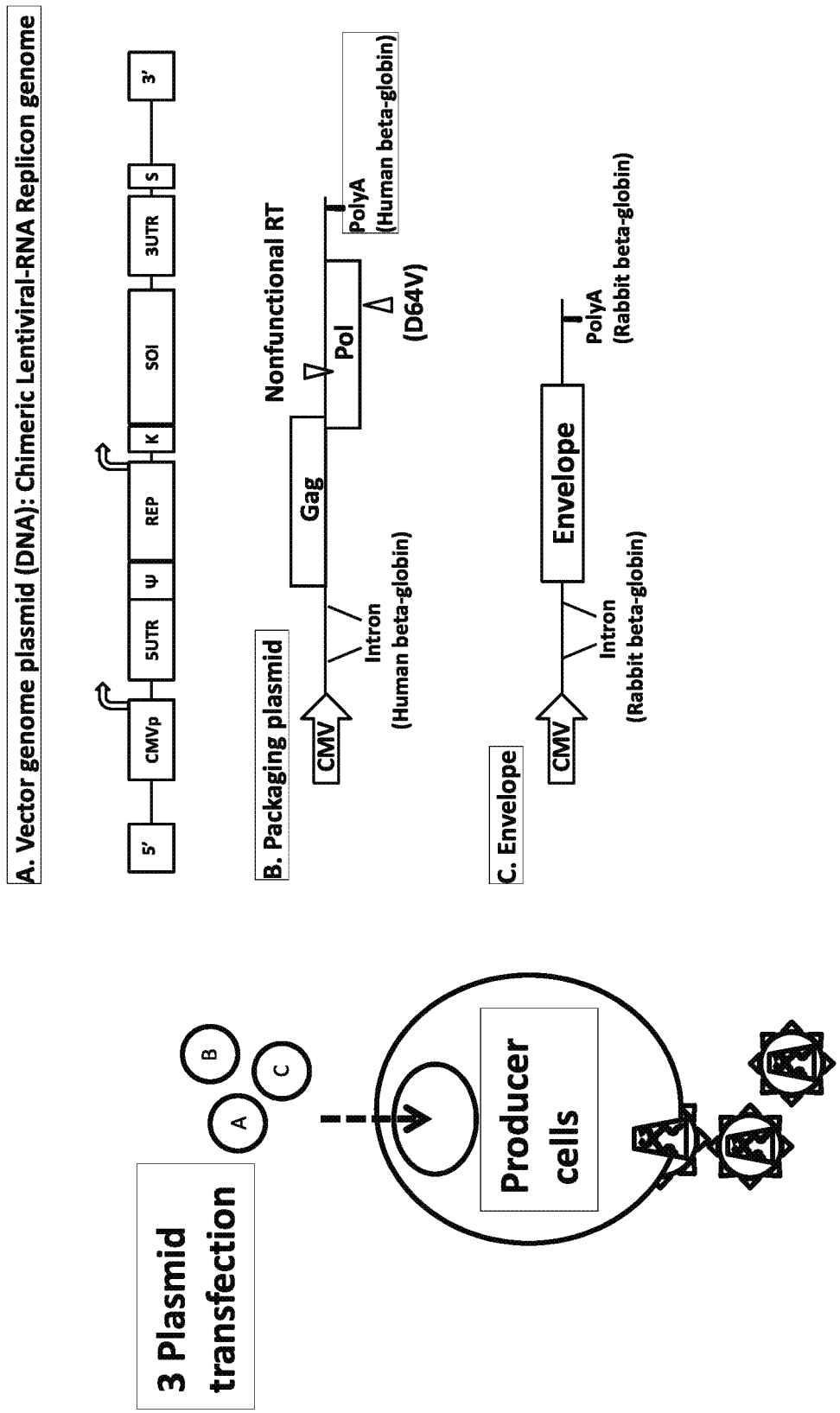
FIG. 4 is a schematic of a first example of a packaging system for producing reverse transcriptase independent chimeric lentiviral-RNA replicon vector particles. This packaging system provides the vector genome from a DNA plasmid vectors as in a typical packaging system.
Figure 5:
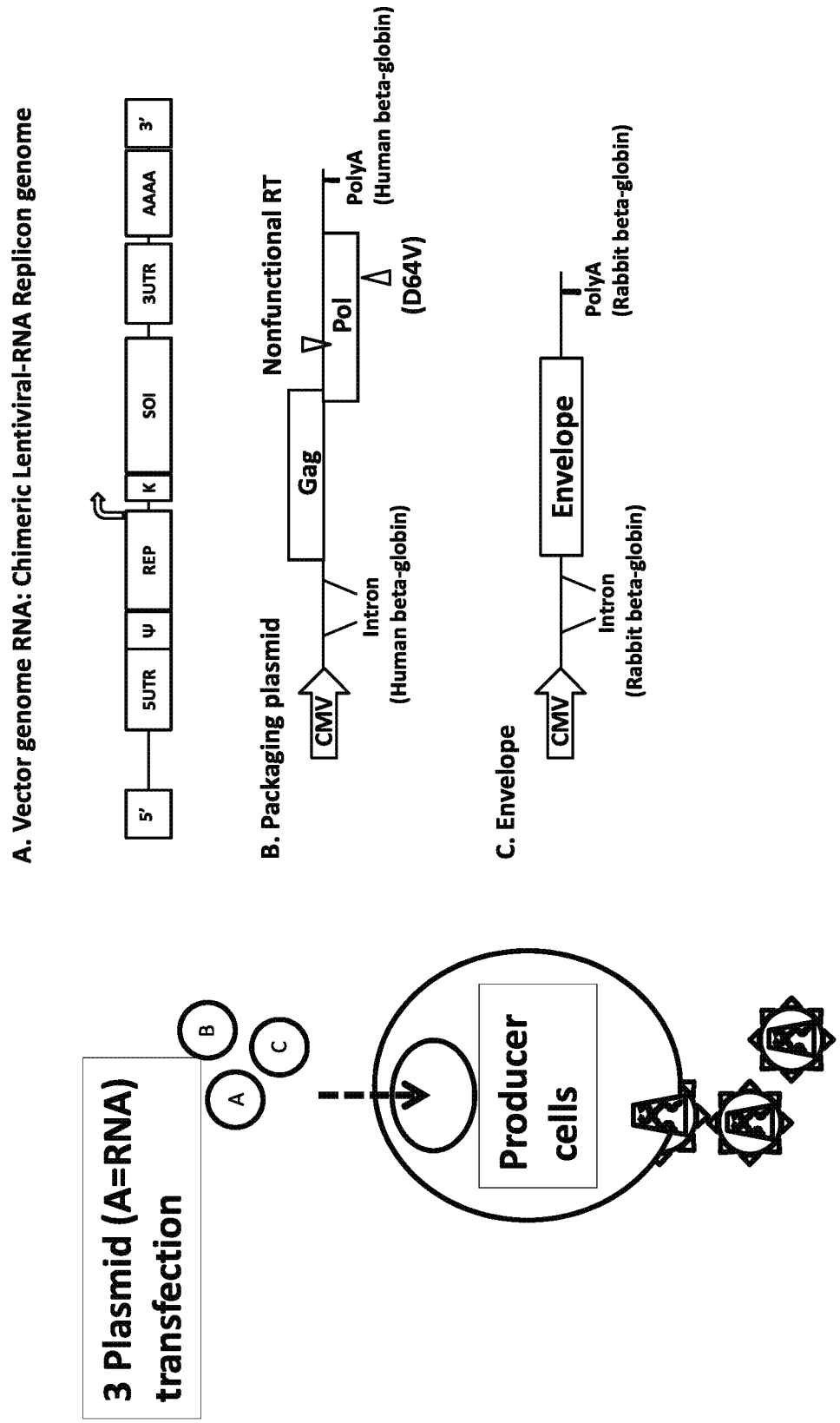
FIG. 5 is a schematic of a second example of a packaging system for producing reverse transcriptase independent chimeric lentiviral-RNA replicon vector particles. This packaging system provides the vector genome in the form of an RNA replicon. In this system, the replicase from the RNA replicon produces the genome to be packaged. The vector genome RNA includes the lentiviral packaging signal to allow efficient packaging into the viral particle.
Figure 6:
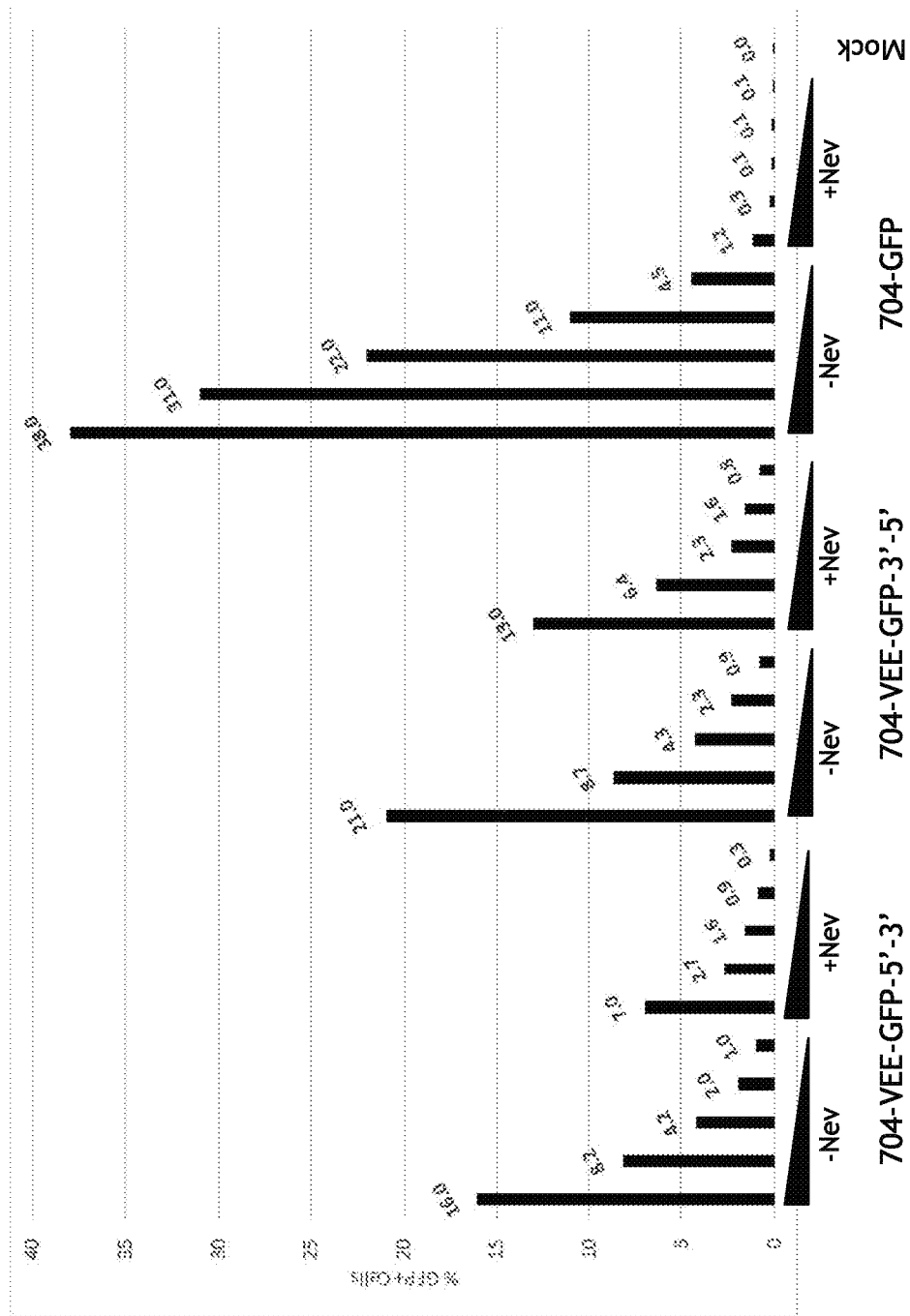
FIG. 6 is a graph showing that chimeric lentiviral-RNA replicon vector particles encoding the GFP reporter protein were produced in 293T producer cells expressing DC-SIGN. Nevirapine (Nev) only partially reduced LV-replicon transductions indicating that some GFP production does not require reverse transcription.
Figure 7:
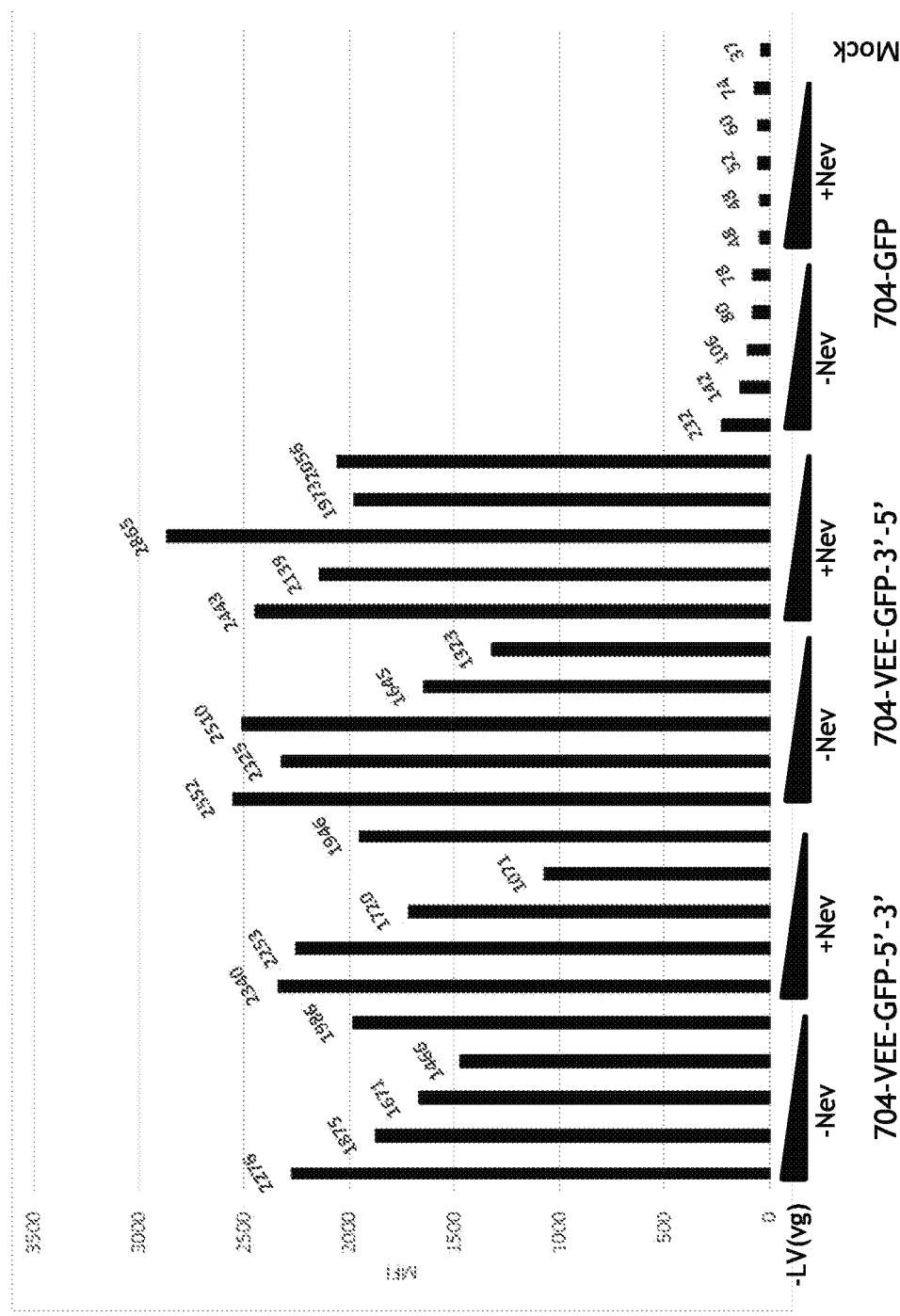
FIG. 7 is a graph showing that the GFP expression level (mean fluorescence intensity) in LV-replicon infected 293T-DC-SIGN cells is about 10 to 50 fold higher than the mean fluorescence intensity of the parent lentiviral vector, 704-GFP. (Parent LV-704-GFP: see e.g., FIG. 2A; also as described in U.S. Pat. No. 8,187,872); 704-VEE-GFP-5'-3'.

In general, the chimeric vector particles are produced by a cell line that is transfected with one or more plasmid vectors containing the components necessary to generate the particles. In certain embodiments, the packaging cell line can be genetically modified (such as through transduction) to stably express one or more of the components necessary to generate the particles. Such packaging cells and systems are well known in the art and would be readily known to the skilled person. These chimeric retroviral (e.g., lentiviral) vector particles are typically not replication-competent, i.e., they are only capable of a single round of infection. Most often, multiple plasmid vectors are utilized to separate the various genetic components that generate the chimeric lentiviral vector particles, mainly to reduce the chance of recombination events that might otherwise generate replication competent viruses. A single plasmid vector having all of the chimeric lentiviral components can be used if desired, however. As one example of a system that employs multiple plasmid vectors, a cell line is transfected with at least one plasmid containing the viral vector genome (i.e., the vector genome plasmid), including the LTRs, the cis-acting packaging sequence, and the RNA replicon comprising the sequence(s) of interest, which are often operably linked to a heterologous promoter, at least one plasmid encoding the virus enzymatic and structural components (i.e., the packaging plasmid that encodes components such as, Gag and Pol polyproteins—as would be readily recognized by the person of skill in the art, Gag comprises matrix, capsid and nucleocapsid proteins; Pol includes protease, reverse transcriptase, p15 and integrase), and at least one envelope plasmid encoding an envelope glycoprotein. Additional plasmids can be used to enhance retrovirus particle production, e.g., Rev-expression plasmids, as described herein and known in the art. Viral particles bud through the cell membrane and comprise a core that includes a genome containing the RNA replicon comprising the sequence of interest and an envelope glycoprotein. In certain embodiments, the envelope glycoprotein is an arbovirus glycoprotein that targets dendritic cells. When the Arbovirus glycoprotein is Sindbis virus E2 glycoprotein, the glycoprotein is engineered to have reduced binding to heparan sulfate compared to the reference strain HR.

Transfection of packaging cells with plasmid vectors of the present invention can be accomplished by well-known methods, and the method to be used is not limited in any way. A number of non-viral delivery systems are known in the art, including for example, electroporation, lipid-based delivery systems including liposomes, delivery of "naked" DNA, and delivery using polycyclodextrin compounds, such as those described in Schatzlein AG. (2001. Non-Viral Vectors in Cancer Gene Therapy: Principles and Progresses. Anticancer Drugs). Cationic lipid or salt treatment methods are typically employed, see, for example, Graham et al. (1973. Virol. 52:456; Wigler et al. (1979. Proc. Natl. Acad. Sci. USA 76:1373-76). The calcium phosphate precipitation method is most often used. However, other methods for introducing the vector into cells may also be used, including nuclear microinjection and bacterial protoplast fusion.

The packaging cell line provides the components, including viral regulatory and structural proteins, that are required in trans for the packaging of the viral genomic RNA into pseudotyped chimeric retroviral vector particles. The packaging cell line may be any cell line that is capable of expressing retroviral (e.g. lentiviral) proteins and producing functional retroviral vector particles. Some suitable packaging cell lines include 293 (ATCC CCL X), 293T, HeLa (ATCC CCL 2), D17 (ATCC CCL 183), MDCK (ATCC CCL 34), BHK (ATCC CCL-10) and Cf2Th (ATCC CRL 1430) cells. The packaging cell line may stably express the necessary viral proteins. Such a packaging cell line is described, for example, in U.S. Pat. Nos. 6,218,181; 8,187,872. Alternatively a packaging cell line may be transiently transfected with nucleic acid molecules encoding one or more necessary viral proteins along with the viral vector genome. The resulting viral particles are collected and used to infect a target cell. The gene(s) encoding envelope glycoprotein(s) is usually cloned into an expression vector, such as pcDNA3 (Invitrogen, CA USA). Eukaryotic cell expression vectors are well known in the art and are available from a number of commercial sources. Packaging cells, such as 293T cells are then co-transfected with the viral vector genome encoding a sequence of interest (typically encoding an antigen), at least one plasmid encoding virus packing components, and a vector for expression of the targeting molecule. The envelope is expressed on the membrane of the packaging cell and incorporated into the viral vector.

In one scenario, one or more vectors are used to introduce polynucleotide sequences into a packaging cell line for the preparation of a lentiviral vector particle pseudotyped with a Sindbis virus envelope glycoprotein such as E2, as described herein. The vectors can contain polynucleotide sequences encoding the various components of the virus including the Sindbis virus envelope, a sequence(s) of interest (typically encoding an antigen), and any components necessary for the production of the virus that are not provided by the packaging cell.

In yet other scenarios, packaging cells are co-transfected with a viral vector genome encoding an antigen and one or more additional vectors. For example, in addition to the viral vector encoding an antigen, a second vector preferably carries the genes encoding a modified (also called a variant) Sindbis virus envelope. In some situations, the viral vector genome encoding an antigen also includes a polynucleotide sequence encoding a selected immune modulating factor, including non-limiting examples of a chemokine, a cytokine, a DC maturation factor, or a factor that regulates immune checkpoint mechanisms. In other situations, the polynucleotide sequence encoding a selected immune modulating factor is contained in a third vector that is co-transfected with the viral vector encoding an antigen and the one or more additional vectors into the packaging cells.

FIG. 3 is a schematic of an exemplary vector packaging system including illustrative vectors used in packaging chimeric lentiviral-RNA replicon vector particles.

FIG. 4 is a schematic of a first example of a packaging system for producing reverse transcriptase independent chimeric lentiviral-RNA replicon vector particles. This packaging system provides the vector genome from a DNA plasmid vectors as in a typical packaging system. FIG. 5 is a schematic of a second example of a packaging system for producing reverse transcriptase independent chimeric lentiviral-RNA replicon vector particles. This packaging system provides the vector genome in the form of a self replicating RNA replicon. In this system, the replicase from the RNA replicon produces the genome to be packaged. The vector genome RNA includes a retroviral packaging signal to allow efficient packaging into the viral particle. While denoted psi (ψ), the retroviral packaging signal may comprise the core encapsidation signal which includes but is not limited to the psi and DIS sequences (see Moore, & Hu 2009 AIDS Rev 11:91-102).

In certain embodiments, the production of the viral particles may be carried out in a packaging system wherein the gag-pol (whether encoding function RT and/or integrase or non functional versions of these proteins), vpx (when included), and the envelope proteins are encoded from self replicating RNA replicons. In other embodiments, these proteins are encoded from DNA plasmids as in more common packaging systems.

In some or any embodiments, the lentiviral vector particles described herein comprise a SAMHD1 inhibitor. In certain embodiments, the SAMHD1 inhibitor is a Vpx protein or a Vpr protein. In certain embodiments, the lentiviral vector particles described herein comprise a Vpx protein or a variant thereof (see e.g., WO2013/149167). In some or any embodiments, the variant retains the ability to inhibit SAMHD1.

In certain embodiments, the viral particles are produced in mammalian cells in the presence of the mannosidase I inhibitor, such as kifunensine (see e.g., WO2013/149167). Thus, in some or any embodiments, a virus packaging cell is cultured in the presence of a mannosidase I inhibitor. In some or any embodiments, the mannosidase I inhibitor is kifunensine. In some embodiments, kifunensine is present in the media at a concentration of about 0.01 µg/ml to about 1 mg/ml, about 0.1 µg/ml to about 10 µg/ml, about 0.1 µg/ml to about 9 µg/ml, about 0.1 µg/ml to about 8 µg/ml, about 0.1 µg/ml to about 7 µg/ml, about 0.1 µg/ml to about 6 µg/ml, about 0.1 µg/ml to about 5 µg/ml, about 0.1 µg/ml to about 4 µg/ml, about 0.1 µg/ml to about 3 µg/ml, about 0.1 µg/ml to about 2 µg/ml, about 0.1 µg/ml to about 1 µg/ml, about 0.25 µg/ml to about 10 µg/ml, about 0.25 µg/ml to about 9 µg/ml, about 0.25 µg/ml to about 8 µg/ml, about 0.25 µg/ml to about 7 µg/ml, about 0.25 µg/ml to about 6 µg/ml, about 0.25 µg/ml to about 5 µg/ml, about 0.25 µg/ml to about 4 µg/ml, about 0.25 µg/ml to about 3 µg/ml, about 0.25 µg/ml to about 2 µg/ml, or about 0.25 µg/ml to about 1 µg/ml.

In some or any embodiments wherein a pseudotyped chimeric lentiviral-RNA replicon vector particle comprises a Sindbis virus E2 glycoprotein and a Vpx protein, the lentiviral particles are produced in the presence of a mannosidase I inhibitor. In some embodiments, the mannosidase inhibitor is deoxymannojirimycin (DMNJ). In preferred embodiments, the mannosidase inhibitor is kifunensine. In some embodiments, DMNJ is present in the media at a concentration of about 1.0 µg/ml to about 1.0 mg/ml, about 1.0 µg/ml to about 900 µg/ml, about 1.0 µg/ml to about 800 µg/ml, about 1.0 µg/ml to about 700 µg/ml, about 1.0 µg/ml to about 600 µg/ml, about 1.0 µg/ml to about 500 µg/ml, about 1.0 µg/ml to about 400 µg/ml, about 1.0 µg/ml to about 300 µg/ml, about 1.0 µg/ml to about 200 µg/ml, about 1.0 µg/ml to about 100 µg/ml, about 50 µg/ml to about 500 µg/ml, about 50 µg/ml to about 400 µg/ml, about 50 µg/ml to about 300 µg/ml, about 50 µg/ml to about 200 µg/ml, about 50 µg/ml to about 100 µg/ml, about 100 µg/ml to about 500 µg/ml, about 100 µg/ml to about 400 µg/ml, about 100 µg/ml to about 300 µg/ml, about 100 µg/ml to about 200 µg/ml, about 200 µg/ml to about 500 µg/ml, or about 200 µg/ml to about 400 µg/ml.

In some or any embodiments, a pseudotyped lentiviral vector particle produced in the presence of a mannosidase I inhibitor (e.g., kifunensine) comprises an envelope glycoprotein (e.g., Sindbis virus E2), wherein at least 60% of N-linked glycans comprise a Mannose$_5$ (Man$_5$), Man$_6$, Man$_7$, Man$_8$, and/or Man$_9$ structure. In some embodiments, at least 65%, at least 70%, at least 75%, at least 80%, at least 85%, at least 90%, at least 95%, at least 96%, at least 97%, at least 98%, at least 99%, or 100% of N-linked glycans comprise a Man$_5$, Man$_6$, Man$_7$, Man$_8$, and/or Man$_{9+}$ structure.

In one scenario, one or more vectors are used to introduce polynucleotide sequences into a packaging cell line for the preparation of a chimeric lentiviral-RNA replicon vector particle pseudotyped with a Sindbis virus envelope glycoprotein such as E2, as described herein. In some embodiments, the chimeric lentiviral vector particle is highly mannosylated. In some embodiments, the chimeric lentiviral vector particle also comprises a Vpx protein or variant thereof. In yet other embodiments, the chimeric lentiviral vector particle is highly mannosylated and comprises a Vpx protein or variant thereof. The vectors can contain polynucleotide sequences encoding the various components of the virus including the Sindbis virus envelope, a sequence(s) of interest (typically encoding an antigen), and any components necessary for the production of the virus that are not provided by the packaging cell.

The glycosylation profile of a viral envelope protein can be determined by any method known in the art. For example, gel shift assays on viral glycoproteins treated with glycosidases (e.g., EndoH or PNGaseF) or left untreated may be compared. Other methods include cleaving glycans from the viral glycoproteins and separating and identifying the components via HPLC and mass spectrometry methods Production of virus is measured as described herein and expressed as IU per volume. IU is infectious unit, or alternatively transduction units (TU); IU and TU can be used interchangeably as a quantitative measure of the titer of a viral vector particle preparation. As described herein, virus is produced in which the genome can express a product that is readily measurable. A fluorescent protein, green fluorescent protein, is preferred. The lentiviral vector is typically non-integrating. The virus is then administered to target cells and the number of target cells that express GFP is determined, such as by flow cytometry (see Example 3). The titer is then calculated. The titer is preferably as high as possible, but at least $1 \times 10^5$ IU/mL, at least $3 \times 10^5$ IU/mL, at least $1 \times 10^6$ IU/mL, at least $3 \times 10^6$ IU/mL, or at least $1 \times 10^7$ IU/mL of cell supernatant (before any concentration). Alternatively, the titer is at least 80%, at least 90%, at least 95%, at least 100% of the titer of the same lentiviral vector pseudotyped in the same cells with VSV-G envelope.

D. Delivery of the Virus

The chimeric virus may be delivered to a target cell in any way that allows the virus to contact the target cells (e.g., DCs, tumor cells, other immune cells) in which delivery of a polynucleotide of interest is desired. At times, a suitable amount of virus will be introduced into a human or other animal directly (in vivo), e.g., though injection into the body.

Suitable animals include, without limitation, horses, dogs, cats, cattle, pigs, sheep, rabbits, chickens or other birds. Suitable animals include any mammal. Viral particles may be injected by a number of routes, such as intravenous, intra-dermal, subcutaneous, intranodal, intratumoral, intraperitoneal cavity, or mucosal. The virus may be delivered using a subdermal injection device such the devices disclosed in U.S. Pat. Nos. 7,241,275, 7,115,108, 7,108,679, 7,083,599, 7,083,592, 7,047,070, 6,971,999, 6,808,506, 6,780,171, 6,776,776, 6,689,118, 6,670,349, 6,569,143, 6,494,865, 5,997,501, 5,848,991, 5,328,483, 5,279,552, 4,886,499. Other injection locations also are suitable, such as directly into organs comprising target cells. For example intra-lymph node injection, intra-spleen injection, or intra-bone marrow injection may be used to deliver virus to the lymph node, the spleen and the bone marrow, respectively. Depending on the particular circumstances and nature of the target cells, introduction can be carried out through other means including for example, inhalation, or direct contact with epithelial tissues, for example those in the eye, mouth or skin.

Alternatively, target cells are provided and contacted with the virus in vitro, such as in culture plates. In certain embodiments, the target cells are populations of cells comprising dendritic cells obtained from a healthy subject or a subject in need of treatment or in whom it is desired to stimulate an immune response to an antigen. Methods to obtain cells from a subject are well known in the art and includes phlebotomy, surgical excision, and biopsy. Human DCs may also be generated by obtaining CD34α+ human hematopoietic progenitors and using an in vitro culture method as described elsewhere (e.g., Banchereau et al. Cell 106, 271-274 (2001)).

The virus may be suspended in media and added to the wells of a culture plate, tube or other container. Media containing the virus may be added prior to the plating of the cells or after the cells have been plated. Cells are typically incubated in an appropriate amount of media to provide viability and to allow for suitable concentrations of virus in the media such that transduction of the host cell occurs. The cells are preferably incubated with the virus for a sufficient amount of time to allow the virus to infect the cells. Preferably the cells are incubated with virus for at least 1 hour, at least 5 hours or at least 10 hours.

In both in vivo and in vitro delivery, an aliquot of viral particles containing sufficient number to infect the desired target cells may be used. When the target cell is to be cultured, the concentration of the viral particles is generally at least 1 IU/µL, at least 10 IU/µl, at least 300 IU/µL, at least $1 \times 10^4$ IU/µL, at least $1 \times 10^5$ IU/µL, at least $1 \times 10^6$ IU/µL, or at least $1 \times 10^7$ IU/µL.

Following infection with the virus in vitro, target cells can be introduced (or re-introduced) into a human or other animal. The cells can be introduced into the dermis, under the dermis, or into the peripheral blood stream. The cells introduced into an animal are preferably cells derived from that animal, to avoid an adverse immune response. Cells derived from a donor having a similar immune background may also be used. Other cells that also can be used include those designed to avoid an adverse immunologic response.

Target cells may be analyzed for integration, transcription and/or expression of the sequence or gene(s) of interest, the number of copies of the gene integrated, and the location of the integration, for examples. Such analysis may be carried out at any time and may be carried out by any method known in the art.

Subjects in which a virus or virus-infected dendritic cells are administered can be analyzed for location of infected cells, expression of the virus-delivered polynucleotide or gene of interest, stimulation of an immune response, and monitored for symptoms associated with a disease or disorder by any methods known in the art.

The methods of infecting cells disclosed above do not depend upon individual-specific characteristics of the cells. As a result, they are readily extended to a variety of animal species. In some instances, viral particles are delivered to a human or to human dendritic cells, and in other instances they are delivered to an animal such as a mouse, horse, dog, cat, or mouse or to birds. As discussed herein, the viral vector genome is pseudotyped to confer upon it a broad host range as well as target cell specificity. One of skill in the art would also be aware of appropriate internal promoters and other elements to achieve the desired expression of a sequence of interest in a particular animal species. Thus, one of skill in the art will be able to modify the method of infecting dendritic cells from any species.

E. Therapeutic and Prophylactic Administration

Target cells may be infected with a chimeric vector particle as described herein for the prevention of or treatment of a disease or disorder in a subject in need thereof. In certain embodiments, the chimeric vector particles and compositions comprising such particles as described herein can be used for the treatment of diseases or disorders including but not limited to diseases for which activation of an immune response in a patient would be beneficial. Many such diseases are well known. For example, diseases or disorders that are amenable to treatment or prevention by the methods of the present invention include, without limitation, cancers, autoimmune diseases, and infections, including viral, bacterial, fungal and parasitic infections. In one method, a disease is treated by chimeric viral particles described herein in order to deliver a sequence of interest to dendritic cells, wherein expression of the sequence of interest produces a disease-specific antigen and leads to stimulation of antigen-specific cellular immune responses and humoral immune responses. In certain embodiments, the sequence of interest encodes an antigen against which an immune response is desired, but is not normally expressed in a dendritic cell. The antigen is expressed and presented by the dendritic cell. In other embodiments, the viral vector genome may encode an immunomodulatory molecule as described herein. In additional embodiments, the viral vector genome may encode an antigen and an immunomodulatory molecule.

In one embodiment, the chimeric viral particles are used in a method for expressing a protein of interest in a target cell of interest, for example for gene therapy. In this regard, gene therapy refers to the introduction or expression of a gene into a cell. In various aspects, a chimeric viral vector as described herein comprises an expression control sequence that expresses a therapeutic transgene encoding a polypeptide that provides curative, preventative, or ameliorative benefits to a subject diagnosed with or that is suspected of having monogenic disease, disorder, or condition or a disease, disorder, or condition that is amenable to such therapy by expression of the therapeutic transgene.

In a typical usage, chimeric viral particles deliver to dendritic cells sequences encoding an antigen against which an immune response is desired and/or sequences encoding immunomodulatory molecules. The delivery can be achieved by contacting dendritic cells with the virus in vitro, whereupon the infected dendritic cells are provided to a patient. Other times, delivery can be achieved by delivering the virus to a subject for infecting dendritic cells in vivo. The dendritic cells then stimulate antigen-specific T cells or B cells in a patient to induce cellular and humoral immune responses to the expressed antigen. Thus, the present disclosure provides methods methods of inducing an immune response in a subject, comprising administering to the subject a pharmaceutical composition comprising the chimeric retroviral vector particles described herein. In further embodiments, the present disclosure provides things of treating cancer in a subject, comprising administering to the subject a pharmaceutical composition comprising the chimeric viral vectors described herein, wherein the SOI encodes one or more tumor associated antigens and optionally one or more checkpoint inhibitors or one or more cytokines, or a combination thereof. In another embodiment, the present disclosure provides a method of treating an infectious disease in a subject, comprising administering to the subject a pharmaceutical composition a chimeric retroviral vector particle as described herein wherein the SOI encodes an antigen associated with the infectious disease.

In other embodiments, target cells are infected either in vivo or in vitro with the virus is described herein expressing an immunomodulatory molecule. Infected cells then express immunomodulatory molecule in a patient to modulate the immune response. In such ways, a patient that is suffering from a disease or disorder is treated by generating immune cells with a desired specificity or modulated immune response with an immunomodulatory molecule.

Any antigen that is associated with a disease or disorder can be delivered to dendritic cells using the chimeric viral particles as described herein. An antigen that is associated with the disease or disorder is identified for preparation of a viral particle that targets dendritic cells.

If contacted ex vivo, the target dendritic cells are then transferred back to the patient, for example by injection, where they interact with immune cells that are capable of generating an immune response against the desired antigen. In preferred embodiments, the recombinant virus is injected into the patient where it transduces the targeted dendritic cells in situ. The dendritic cells then express the particular antigen associated with a disease or disorder to be treated, and the patient is able to mount an effective immune response against the disease or disorder.

The viral vector genome may contain a polynucleotide sequence encoding more than one antigen, and upon transduction of a target dendritic cell, generates immune responses to the multitude of antigens delivered to the cell. In some embodiments, the antigens are related to a single disease or disorder. In other embodiments, the antigens are related to multiple diseases or disorders.

In some of the chimeric viruses described herein immunomodulatory molecules that activate and/or stimulate an immune response, and in certain embodiments activate and/or stimulate maturation of the DCs are delivered in conjunction with the sequence of interest. In alternatives, the DCs are activated by delivery of DC maturation factors prior to, simultaneously with, or after delivery of the virus. DC maturation factors may be provided separately from administration of the virus.

As described herein, one or more immunomodulatory factors can be encoded by one or more sequences that are contained in the viral genome and expressed after the virus infects a dendritic cell. The sequences encoding immune modulation factors can also be provided in a separate vector that is co-transfected with the viral vector encoding one or more antigens in a packaging cell line.

The methods described herein can be used for adoptive immunotherapy in a patient. As described above, an antigen against which an immune response is desired is identified. A polynucleotide encoding the desired antigen is obtained and packaged into a chimeric recombinant virus described herein. Target dendritic cells are obtained from the patient and transduced with a recombinant virus containing a polynucleotide that encodes the desired antigen. The dendritic cells are then transferred back into the patient.

The viral particles may be injected in vivo, where they infect target cells, such as DCs, and deliver a sequence of interest, typically encoding an antigen and/or immunomodulatory molecule. The amount of viral particles is at least $3 \times 10^6$ IU, and can be at least $1 \times 10^7$ IU, at least $3 \times 10^7$ IU, at least $1 \times 10^8$ IU, at least $3 \times 10^8$ IU, at least $1 \times 10^9$ IU, or at least $3 \times 10^9$ IU. At selected intervals, DCs from the recipient's lymphoid organs may be used to measure expression, for example, by observing marker expression, such as GFP or luciferase. Nucleic acid monitoring techniques and measurements of reverse transcriptase (RT) activity can also be used to analyze the biodistribution of viral particles. T cells from peripheral blood mononuclear cells, lymph nodes, spleens, or malignant or target pathogen-infected tissue of lentiviral vector particle-treated recipients may be measured from the magnitude and durability of response to antigen stimulation. Tissue cells other than DCs, such as epithelial cells and lymphoid cells, may be analyzed for the specificity of in vivo gene delivery.

It is widely agreed that the most effective potential method to end the AIDS epidemic (and other viral diseases) is an effective preventative vaccine. To date, no vaccination method against HIV has successfully passed a phase III trial. Thus, there is an urgent need for new, effective vaccination strategies. One strategy is vaccination of DCs. In this implementation, a sequence encoding a viral protein, such as those described above, is cloned into a viral vector. Patients are infected with viruses constructed as described herein. In an animal model, molecularly cloned HIV reporter viruses (NFNSZ-r-HSAS, NL-r-HSAS) and clinical isolates may be used to challenge the animals by tail vein injection. Evidence of infection may be monitored over time in splenocytes, lymph nodes, and peripheral blood. PCR amplification for HIV-gag protein and flow cytometry for HAS in the reporter viruses may be used to test for viral integration and replication. Productive in situ DC vaccination may increase resistance to a HIV challenge.

Vaccines often include an adjuvant. The chimeric retroviral vector particles described herein may also be administered along with an adjuvant. The adjuvant may be administered with the recombinant virus particles, before the recombinant virus particles, or after the recombinant virus particles. If administered with the virus particles, desirable adjuvants do not significantly disrupt the integrity of the virus particle, such as disrupting the viral membrane containing the envelope glycoproteins.

A variety of adjuvants can be used in combination with the virus to elicit an immune response to the antigen encoded in the viral vector genome. Preferred adjuvants augment the intrinsic response to an antigen without causing conformational changes in the antigen that affect the qualitative form of the response. Preferred adjuvants include alum, 3 De-O-acylated monophosphoryl lipid A (MPL) (see GB 2220211).

QS21 is a triterpene glycoside or saponin isolated from the bark of the *Quillaja Saponaria* Molina tree found in South America (see Kensil et al., in Vaccine Design: The Subunit and Adjuvant Approach (eds. Powell and Newman, Plenum Press, NY, 1995); U.S. Pat. No. 5,057,540). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Alternatively, Aβ can be coupled to an adjuvant. For example, a lipopeptide version of Aβ can be prepared by coupling palmitic acid or other lipids directly to the N-terminus of Aβ as described for hepatitis B antigen vaccination (Livingston, J. Immunol. 159, 1383-1392 (1997)). However, such coupling should not substantially change the conformation of Aβ so as to affect the nature of the immune response thereto. Adjuvants can be administered as a component of a therapeutic composition with an active agent or can be administered separately, before, concurrently with, or after administration of the therapeutic agent.

One class of adjuvants is aluminum salts (alum), such as aluminum hydroxide, aluminum phosphate, aluminum sulfate. Such adjuvants can be used with or without other specific immunostimulating agents such as MPL or 3-DMP, QS21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalane, 0.4% Tween 80, 5% pluronic-blocked polymer L121, and thr-MDP, either microfluidized into a submicron emulsion or vortexed to generate a larger particle size emulsion, and (c) Ribi adjuvant system (RAS), (Ribi Immunochem, Hamilton, Mont.) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™). Another class of preferred adjuvants is saponin adjuvants, such as Stimulon™ (QS21, Aquila, Worcester, Mass.) or particles generated there from such as ISCOMs (immunostimulating complexes) and ISCOMATRIX. Other adjuvants include Complete Freund's Adjuvant (CFA) and Incomplete Freund's Adjuvant (IFA). Other adjuvants include cytokines, such as interleukins (IL-1, IL-2, and IL-12), macrophage colony stimulating factor (M-CSF), tumor necrosis factor (TNF).

Another adjuvant that can be used with the compositions herein is identified by chemical formula (I):

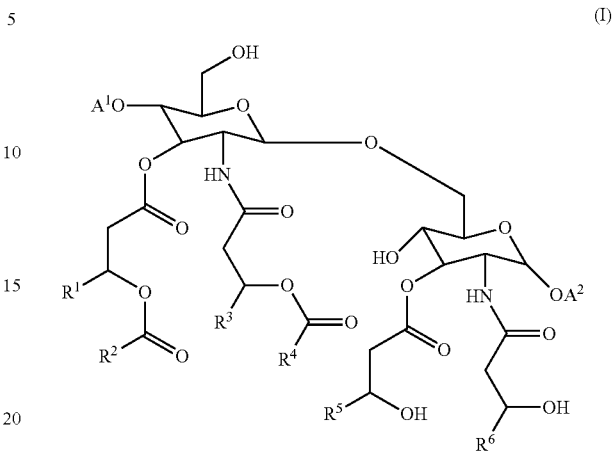

(I)

wherein the moieties A1 and A2 are independently selected from the group of hydrogen, phosphate, and phosphate salts. Sodium and potassium are exemplary counterions for the phosphate salts. The moieties $R^1$, $R^2$, $R^3$, $R^4$, $R^5$, and $R^6$ are independently selected from the group of hydrocarbyl having 3 to 23 carbons, represented by $C_3$-$C_{23}$. For added clarity it will be explained that when a moiety is "independently selected from" a specified group having multiple members, it should be understood that the member chosen for the first moiety does not in any way impact or limit the choice of the member selected for the second moiety. The carbon atoms to which $R^1$, $R^3$, $R^5$ and $R^6$ are joined are asymmetric, and thus may exist in either the R or S stereochemistry. In one embodiment all of those carbon atoms are in the R stereochemistry, while in another embodiment all of those carbon atoms are in the S stereochemistry.

"Hydrocarbyl" refers to a chemical moiety formed entirely from hydrogen and carbon, where the arrangement of the carbon atoms may be straight chain or branched, noncyclic or cyclic, and the bonding between adjacent carbon atoms may be entirely single bonds, i.e., to provide a saturated hydrocarbyl, or there may be double or triple bonds present between any two adjacent carbon atoms, i.e., to provide an unsaturated hydrocarbyl, and the number of carbon atoms in the hydrocarbyl group is between 3 and 24 carbon atoms. The hydrocarbyl may be an alkyl, where representative straight chain alkyls include methyl, ethyl, n-propyl, n-butyl, n-pentyl, n-hexyl, and the like, including undecyl, dodecyl, tridecyl, tetradecyl, pentadecyl, hexadecyl, heptadecyl, octadecyl, etc.; while branched alkyls include isopropyl, sec-butyl, isobutyl, tert-butyl, isopentyl, and the like. Representative saturated cyclic hydrocarbyls include cyclopropyl, cyclobutyl, cyclopentyl, cyclohexyl, and the like; while unsaturated cyclic hydrocarbyls include cyclopentenyl and cyclohexenyl, and the like. Unsaturated hydrocarbyls contain at least one double or triple bond between adjacent carbon atoms (referred to as an "alkenyl" or "alkynyl", respectively, if the hydrocarbyl is non-cyclic, and cycloalkeny and cycloalkynyl, respectively, if the hydrocarbyl is at least partially cyclic). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

The adjuvant of formula (I) may be obtained by synthetic methods known in the art, for example, the synthetic methodology disclosed in PCT International Publication No. WO 2009/035528, which is incorporated herein by reference, as well as the publications identified in WO 2009/035528, where each of those publications is also incorporated herein by reference. Certain of the adjuvants may also be obtained commercially. A preferred adjuvant is Product No. 699800 as identified in the catalog of Avanti Polar Lipids, Alabaster Ala., see E1 in combination with E10, below.

In various embodiments of the invention, the adjuvant has the chemical structure of formula (I) but the moieties A1, A2, R1, R2, R3, R4, R5, and R6 are selected from subsets of the options previously provided for these moieties, where these subsets are identified below by E1, E2, etc.

E1: $A_1$ is phosphate or phosphate salt and $A_2$ is hydrogen.
E2: $R^1$, $R^3$, $R^5$ and $R^6$ are $C_3$-$C_{21}$ alkyl; and $R^2$ and $R^4$ are $C_5$-$C_{23}$ hydrocarbyl.
E3: $R^1$, $R^3$, $R^5$ and $R^6$ are $C_5$-$C_{17}$ alkyl; and $R^2$ and $R^4$ are $C_7$-$C_{19}$ hydrocarbyl.
E4: $R^1$, $R^3$, $R^5$ and $R^6$ are $C_7$-$C_{15}$ alkyl; and $R^2$ and $R^4$ are $C_9$-$C_{17}$ hydrocarbyl.
E5: $R^1$, $R^3$, $R^5$ and $R^6$ are $C_9$-$C_{13}$ alkyl; and $R^2$ and $R^4$ are $C_{11}$-$C_{15}$ hydrocarbyl.
E6: $R^1$, $R^3$, $R^5$ and $R^6$ are $C_9$-$C_{15}$ alkyl; and $R^2$ and $R^4$ are $C_{11}$-$C_{17}$ hydrocarbyl.
E7: $R^1$, $R^3$, $R^5$ and $R^6$ are $C_7$-$C_{13}$ alkyl; and $R^2$ and $R^4$ are $C_9$-$C_{15}$ hydrocarbyl.
E8: $R^1$, $R^3$, $R^5$ and $R^6$ are $C_{11}$-$C_{20}$ alkyl; and $R^2$ and $R^4$ are $C_{12}$-$C_{20}$ hydrocarbyl.
E9: $R^1$, $R^3$, $R^5$ and $R^6$ are $C_{11}$ alkyl; and $R^2$ and $R^4$ are $C_{13}$ hydrocarbyl.
E10: $R^1$, $R^3$, $R^5$ and $R^6$ are undecyl and $R^2$ and $R^4$ are tridecyl.

In certain options, each of E2 through E10 is combined with embodiment E1, and/or the hydrocarbyl groups of E2 through E9 are alkyl groups, preferably straight chain alkyl groups.

The adjuvant of formula (I) may be formulated into a pharmaceutical composition, optionally with a co-adjuvant, each as discussed below. In this regard reference is made to US Patent Publication No. 2008/0131466 which provides formulations, e.g., aqueous formulation (AF) and stable emulsion formulations (SE) for GLA adjuvant, where these formulations may be utilized for any of the adjuvants of formula (I).

An adjuvant can be administered with the virus of the invention as a single composition, or can be administered before, concurrent with or after administration of the recombinant virus of the invention. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the vaccine containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS21 are preferred. Optionally, two or more different adjuvants can be used simultaneously, such as alum with MPL, alum with QS21, MPL with QS21, and alum, QS21 and MPL together. Also, Incomplete Freund's adjuvant can be used (Chang et al., Advanced Drug Delivery Reviews 32, 173-186 (1998)), optionally in combination with any of alum, QS21, and MPL and all combinations thereof.

The compositions comprising a chimeric viral vector as described herein may also be administered simultaneously with, prior to, or after administration of one or more other therapeutic agents.

Such combination therapy may include administration of a single pharmaceutical dosage formulation which contains a chimeric viral vector and one or more additional active agents, as well as administration of compositions comprising a chimeric viral vector of the invention and each active agent in its own separate pharmaceutical dosage formulation. For example, a composition comprising a chimeric viral vector and the other active agent can be administered to the patient together in a single enteral (e.g., oral) dosage composition such as a tablet or capsule, or each agent administered in separate enteral (e.g., oral) dosage formulations. Similarly, compositions comprising a chimeric viral vector and the other active agent can be administered to the patient together in a single parenteral (e.g., any of the parenteral routes known and described herein, such as, subcutaneous, intradermal, intranodal, intratumoral or intramuscular) dosage composition such as in a saline solution or other physiologically acceptable solution, or each agent administered in separate parenteral dosage formulations. The combination therapies as described herein can be administered by the same route or may be administered using different routes. Where separate dosage formulations are used, the compositions comprising chimeric viral vector and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of compositions comprising a chimeric viral vector of this disclosure in combination with one or more other therapeutic agents (e.g. other anti-cancer agents, or other palliative or adjunctive therapy). In certain embodiments, such therapeutic agents may be accepted in the art as a standard treatment for a particular cancer as described herein. Exemplary therapeutic agents contemplated include cytokines, growth factors, steroids, NSAIDs, DMARDs, anti-inflammatories, immune checkpoint inhibitors, chemotherapeutics, radiotherapeutics, or other active and ancillary agents.

In one embodiment, compositions comprising a chimeric viral vector are administered in combination with one or more cancer therapeutic agents, including one or more chemotherapeutic agents. Examples of cancer therapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; trastuzumab, docetaxel, platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such asTargretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Further cancer therapeutic agents include sorafenib and other protein kinase inhibitors such as afatinib, axitinib, bevacizumab, cetuximab, crizotinib, dasatinib, erlotinib, fostamatinib, gefitinib, imatinib, lapatinib, lenvatinib, mubritinib, nilotinib, panitumumab, pazopanib, pegaptanib, ranibizumab, ruxolitinib, trastuzumab, vandetanib, vemurafenib, and sunitinib; sirolimus (rapamycin), everolimus and other mTOR inhibitors.

In another embodiment, the chimeric viral vector compositions herein are administered in combination with another immunostimulatory agent. Such immunostimulatory agents include, but are not limited to, N-acetylmuramyl-L-alanine-D-isoglutamine (MDP), glucan, IL-12, GM-CSF, interferon-γ and anti-CD40 antibodies or other antibodies that bind to and activate co-stimulatory pathways (e.g., CD28, ICOS, OX40, CD27 and the like).

In one embodiment, the chimeric viral vector compositions herein are administered in combination with one or more immune checkpoint inhibitors. Immune checkpoints refer to a variety of inhibitory pathways of the immune system that are crucial for maintaining self-tolerance and for modulating the duration and amplitude of an immune responses. Tumors use certain immune-checkpoint pathways as a major mechanism of immune resistance, particularly against T cells that are specific for tumor antigens. (see, e.g., Pardoll, 2012 Nature 12:252; Chen and Mellman 2013 Immunity 39:1). The present disclosure provides immune checkpoint inhibitors that can be administered in combination with the GLA compositions without antigen. Such combination therapies work in concert to enhance an anti-cancer immune response. Certain viruses have also developed mechanisms to co-opt immune checkpoint pathways. Therefore, in certain embodiments, such combination therapy may be used to enhance an anti-viral immune response.

Immune checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative immune checkpoint molecules that may be targeted for blocking or inhibition include, but are not limited to, CTLA-4, 4-166 (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, γδ, and memory $CD8^+$ (αβ) T cells), CD160 (also referred to as BY55) and CGEN-15049. Immune checkpoint inhibitors include antibodies, or antigen binding fragments thereof, or other binding proteins, that bind to and block or inhibit the activity of one or more of CTLA-4, PDL1, PDL2, PD1, B7-H3, B7-H4, BTLA, HVEM, TIM3, GAL9, LAG3, TIM3, B7H3, B7H4, VISTA, KIR, 2B4, CD160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor).

In a further embodiment, the chimeric viral vector compositions herein are administered in combination with other TLR4 agonists, or a TLR8 agonist, or a TLR9 agonist. Such an agonist may be selected from peptidoglycan, polyI:C, CpG, 3M003, flagellin, and Leishmania homolog of eukaryotic ribosomal elongation and initiation factor 4a (LeIF).

In an additional embodiment, the chimeric viral vector compositions herein are administered in combination with a cytokine. By "cytokine" is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1 through IL-36, including, but not limited to, IL-1, IL-1alpha, IL-2, IL-3, IL-4, IL-5, IL-6, IL-7, IL-8, IL-9, IL-10, IL-11, IL-12; IL-15, IL-18, IL-21, IL-23, IL-27, TNF; and other polypeptide factors including LIF and kit ligand (KL). As used herein, the term cytokine includes proteins from natural sources or from recombinant cell culture, and biologically active equivalents of the native sequence cytokines.

In certain embodiments, the compositions comprising chimeric viral vectors as described herein may be administered in combination with chloroquine, a lysosomotropic agent that prevents endosomal acidification and which inhibits autophagy induced by tumor cells to survive accelerated cell growth and nutrient deprivation. More generally, the compositions comprising chimeric viral vectors as described herein may be administered in combination with therapeutic agents that act as autophagy inhibitors, radiosensitizers or chemosensitizers, such as chloroquine, misonidazole, metronidazole, and hypoxic cytotoxins, such as tirapazamine. In this regard, such combinations of a chimeric viral vector with chloroquine or other radio or chemo sensitizer, or autophagy inhibitor, can be used in further combination with other cancer therapeutic agents or with radiation therapy.

In another embodiment, the compositions comprising chimeric viral vectors as described herein may be administered in combination with small molecule drugs which are known to result in killing of tumor cells with concomitant activation of immune responses, termed "immunogenic cell death", such as cyclophosphamide, doxorubicin, oxaliplatin and mitoxantrone. Furthermore, combinations with drugs known to enhance the immunogenicity of tumor cells such as patupilone (epothilone B), epidermal-growth factor receptor (EGFR)-targeting monoclonal antibody 7A7.27, histone deacetylase inhibitors (e.g., vorinostat, romidepsin, panobinostat, belinostat, and entinostat), the n3-polyunsaturated fatty acid docosahexaenoic acid, furthermore proteasome inhibitors (e.g. bortezomib), shikonin (the major constituent of the root of Lithospermum erythrorhizon) and oncolytic viruses, such as TVec (talimogene laherparepvec). In other embodiments, the compositions comprising chimeric viral vectors as described herein may be administered in combination with epigenetic therapies, such as DNA methyltransferase inhbitors (e.g. Decitabine, 5-aza-2'-deoxycytidine) which may be administered locally or systemically.

In another embodiment, the compositions comprising a chimeric viral vector as described herein may be administered in combination with one or more antibodies that increase ADCC uptake of tumor by DCs. Thus, the present invention contemplates combining compositions comprising a chimeric viral vector with any molecule that induces or enhances the ingestion of a tumor cell or its fragments by an antigen presenting cell and subsequent presentation of tumor antigens to the immune system. These molecules include agents that induce receptor binding (such as Fc or mannose receptors) and transport into the antigen presenting cell such as antibodies, antibody-like molecules, multi-specific multivalent molecules and polymers. Such molecules may either be administered intratumorally with the composition comprising chimeric viral vector, or administered by a different route. For example, a composition comprising chimeric viral vector as described herein may be administered intratumorally in conjunction with intratumoral injection of rituximab, cetuximab, trastuzumab, Campath, panitumumab, ofatumumab, brentuximab, pertuzumab, Ado-trastuzumab emtansine, Obinutuzumab, anti-HER1, -HER2, or -HER3 antibodies (e.g., MEHD7945A; MM-111; MM-151; MM-121; AMG888), anti-EGFR antibodies (e.g. Nimotuzumab, ABT-806), or other like antibodies. Any multivalent scaffold that is capable of engaging Fc receptors and other receptors that can induce internalization may be used in the combination therapies described herein—e.g. peptides and/or proteins capable of binding targets that are linked to Fc fragments or polymers capable of engaging receptors.

In certain embodiments, the combination of chimeric viral vector with such antibodies may be further combined with an antibody that promotes a co-stimulatory signal (e.g., by blocking inhibitory pathways), such as anti-CTLA-4, or that activates co-stimulatory pathways such as an anti-CD40, anti-CD28, anti-ICOS, anti-OX40, anti-CD27 antibodies and the like.

The compositions comprising chimeric viral vector may be administered alone or in combination with other known cancer treatments, such as radiation therapy, immune checkpoint inhibitors, chemotherapy or other cancer therapeutic agents, transplantation, immunotherapy, hormone therapy, photodynamic therapy, etc. The compositions may also be administered in combination with antibiotics.

The present disclosure provides for methods of treating a variety of diseases by administering a therapeutically effect amount of the chimeric viral vectors dislosed herein, optionally in combination with other therapeutic agents. Diseases contemplated herein for treatment using the chimeric retroviral-replicon vectors described herein include any of a variety of cancers, autoimmune diseases, infectious diseases, and genetic disorders.

Examples of specific cancers include, but are not limited to, lung cancer, colon cancer, breast cancer, testicular cancer, stomach cancer, pancreatic cancer, ovarian cancer, liver cancer, bladder cancer, colorectal cancer, and prostate cancer. Additional cancers are well known to those of skill in the art and include, but are not limited to: leukemia, lymphoma, cervical cancer, glioma tumors, adenocarcinomas, sarcomas, soft tissue sarcomas and skin cancer. Other exemplary cancers include, but are not limited to, a bladder tumor, breast tumor, prostate tumor, basal cell carcinoma, biliary tract cancer, bladder cancer, bone cancer, brain and CNS cancer (e.g., glioma tumor), cervical cancer, choriocarcinoma, colon and rectum cancer, connective tissue cancer, cancer of the digestive system; endometrial cancer, esophageal cancer; eye cancer; cancer of the head and neck; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma; neuroblastoma, oral cavity cancer (e.g., lip, tongue, mouth, and pharynx); ovarian cancer; pancreatic cancer, retinoblastoma; rhabdomyosarcoma; rectal cancer, renal cancer, cancer of the respiratory system; sarcoma, skin cancer; stomach cancer, testicular cancer, thyroid cancer; uterine cancer, cancer of the urinary system, as well as other carcinomas and sarcomas. Cancer also includes neoplasias and malignant disorders in mammals that are well known in the art. In one embodiment, the present disclosure provides methods of treating cancer by intratumoral injection of the chimeric vectors described herein. In this regard, any cancer with an injectable tumor is contemplated herein for intratumoral injection with the chimeric vectors described herein.

The chimeric viral vectors herein can be used to treat a variety of autoimmune diseases such as, but not limited to, arthritis (including rheumatoid arthritis, reactive arthritis), systemic lupus erythematosus (SLE), psoriasis and inflammatory bowel disease (IBD), encephalomyelitis, uveitis, myasthenia gravis, multiple sclerosis, insulin dependent diabetes, Addison's disease, celiac disease, chronic fatigue syndrome, autoimmune hepatitis, autoimmune alopecia, ankylosing spondylitis, ulcerative colitis, Crohn's disease, fibromyalgia, pemphigus vulgaris, Sjogren's syndrome, Kawasaki's Disease, hyperthyroidism/Graves disease, hypothyroidism/Hashimoto's disease, endometriosis, scleroderma, pernicious anemia, Goodpasture syndrome, Guillain-Barré syndrome, Wegener's disease, glomerulonephritis, aplastic anemia (including multiply transfused aplastic anemia patients), paroxysmal nocturnal hemoglobinuria, myelodysplastic syndrome, idiopathic thrombocytopenic purpura, autoimmune hemolytic anemia, Evan's syndrome, Factor VIII inhibitor syndrome, systemic vasculitis, dermatomyositis, polymyositis and rheumatic fever, Autoimmune Lymphoproliferative Syndrome (ALPS), Autoimmune Bullous Pemphigoid, Parkinson's, sarcoidosis, vitiligo, primary biliary cirrhosis, autoimmune myocarditis.

Other diseases amenable to treatment with the chimeric vector disclosed herein include Crohn's disease, colitis, dermatitis, psoriasis, diverticulitis, hepatitis, irritable bowel syndrom (IBS), lupus erythematous, nephritis, Parkinson's disease, ulcerative colitis, multiple sclerosis (MS), Alzheimer's disease, arthritis, rheumatoid arthritis, asthma, and various cardiovascular diseases such as atherosclerosis and vasculitis. In certain embodiments, the disease is selected from the group consisting of rheumatoid arthritis, diabetes, gout, cryopyrin-associated periodic syndrome, and chronic obstructive pulmonary disorder. In this regard, one embodiment provides a method of treating, reducing the severity of or preventing inflammation or an inflammatory disease by administering to a patient in need thereof a therapeutically effective amount of a herein disclosed compositions.

F. Pharmaceutical Compositions and Kits

Also contemplated herein are pharmaceutical compositions and kits containing a virus provided herein and one or more components. Pharmaceutical compositions can include viral vector particles as provided herein and a pharmaceutical carrier. Kits can include the pharmaceutical compositions and/or combinations provided herein, and one or more components, such as instructions for use, a device for administering a compound to a subject, and a device for administering a compound to a subject.

Provided herein are pharmaceutical compositions containing viral particles as provided herein and a suitable pharmaceutical carrier. Pharmaceutical compositions provided herein can be in various forms, e.g., in solid, liquid, powder, aqueous, or lyophilized form. Examples of suitable pharmaceutical carriers are known in the art. Such carriers and/or additives can be formulated by conventional methods and can be administered to the subject at a suitable dose. Stabilizing agents such as lipids, nuclease inhibitors, polymers, and chelating agents can preserve the compositions from degradation within the body.

The chimeric viral vector particles provided herein can be packaged as kits. Kits can optionally include one or more components such as instructions for use, devices, and additional reagents, and components, such as tubes, containers and syringes for practice of the methods. Exemplary kits can include the viruses provided herein, and can optionally include instructions for use, a device for detecting a virus in a subject, a device for administering the virus to a subject, and a device for administering a compound to a subject.

Kits comprising polynucleotides comprising an RNA replicon comprising a gene of interest (typically encoding an antigen) are also contemplated herein. The kit may include at least one plasmid encoding virus packaging components and vector encoding envelope glycoprotein (e.g., Sindbis virus E2 glycoprotein variant). Some kits will contain at least one plasmid encoding virus packaging components, a vector encoding Sindbis virus E2 glycoprotein variant, and a vector encoding at least one immunomodulatory molecule.

Kits comprising a viral vector encoding a sequence of interest (typically an antigen) and optionally, a polynucleotide sequence encoding a DC maturation factor are also contemplated herein. In some kits, the kit includes at least one plasmid encoding virus packaging components and a vector encoding Sindbis virus E2 glycoprotein variant.

A kit may also contain instructions. Instructions typically include a tangible expression describing the virus and, optionally, other components included in the kit, and methods for administration, including methods for determining the proper state of the subject, the proper dosage amount, and the proper administration method, for administering the virus. Instructions can also include guidance for monitoring the subject over the duration of the treatment time.

Kits provided herein also can include a device for administering a virus to a subject. Any of a variety of devices known in the art for administering medications or vaccines can be included in the kits provided herein. Exemplary devices include, but are not limited to, a hypodermic needle, an intravenous needle, a catheter, a needle-less injection device, an inhaler, and a liquid dispenser, such as an eyedropper. Typically, the device for administering a virus of the kit will be compatible with the virus of the kit; for example, a needle-less injection device such as a high pressure injection device can be included in kits with viruses not damaged by high pressure injection, but is typically not included in kits with viruses damaged by high pressure injection.

Kits provided herein also can include a device for administering a compound, such as an immunomodulatory molecule or other therapeutic agent as described herein, to a subject. Any of a variety of devices known in the art for administering medications to a subject can be included in the kits provided herein. Exemplary devices include a hypodermic needle, an intravenous needle, a catheter, a needle-less injection, but are not limited to, a hypodermic needle, an intravenous needle, a catheter, a needle-less injection device, an inhaler, and a liquid dispenser such as an eyedropper. Typically the device for administering the compound of the kit will be compatible with the desired method of administration of the compound.

As used herein, the term "about" or "approximately" refers to a quantity, level, value, number, frequency, percentage, dimension, size, amount, weight or length that varies by as much as 15 percent, 10 percent, 9 percent, 8 percent, 7 percent, 6 percent, 5 percent, 4 percent, 3 percent, 2 percent or 1 percent to a reference quantity, level, value, number, frequency, percentage, dimension, size, amount, weight or length. In one aspect, the term "about" or "approximately" refers a range of quantity, level, value, number, frequency, percentage, dimension, size, amount, weight or length plus or minus 15 percent, plus or minus 10 percent, plus or minus 9 percent, plus or minus 8 percent, plus or minus 7 percent, plus or minus 6 percent, plus or minus 5 percent, plus or minus 4 percent, plus or minus 3 percent, plus or minus 2 percent, or plus or minus 1 percent about a reference quantity, level, value, number, frequency, percentage, dimension, size, amount, weight or length.

The following examples are offered by way of illustration, and not by way of limitation.

EXAMPLES

Example 1

Engineering of a Chimeric Lentiviral-RNA Replicon Vector

This example describes the cloning strategy for constructing a chimeric lentiviral-RNA replicon vector.

The alphaviral genome functions directly as an mRNA, is 5'-capped and 3' polyadenylated. Replication of the alphavirus self replicating RNA yields high levels of a shorter, sub-genomic RNA species derived from the 3' end of the RNA and driven from the 26S RNA dependent RNA polymerase promoter. The sub genomic RNA nucleotide sequence is translated at extremely high levels (up to 20% of total cell protein).

The starting lentiviral vector genome has been described previously (*Molecular Therapy* vol. 22 no. 3, 575-587, 2014). The alphaviral sequences (5'UTR, nonstructural proteins, 26S promoter, and 3'UTR sequences) were derived from GenBank accession number L01443.1, Venezuelan equine encephalitis virus strain TC-83 (attenuated). An illustrative wild type alphavirus sequence is provided in SEQ ID NO:1.

Two cloning strategies were taken using standard molecular biology techniques. The first was a chimeric genome with the alphaviral RNA replicon in the 5' to 3' direction as shown in FIG. 2A. The second strategy was a chimeric genome with the alphaviral RNA replicon in the 3' to 5' direction as shown in FIG. 2B. These strategies were taken due to the presence of an SV40 transcription stop/polyadenylation signal in the starting lentiviral vector which is likely to truncate the full-length lentiviral RNA message.

Example 2

Figure 3:
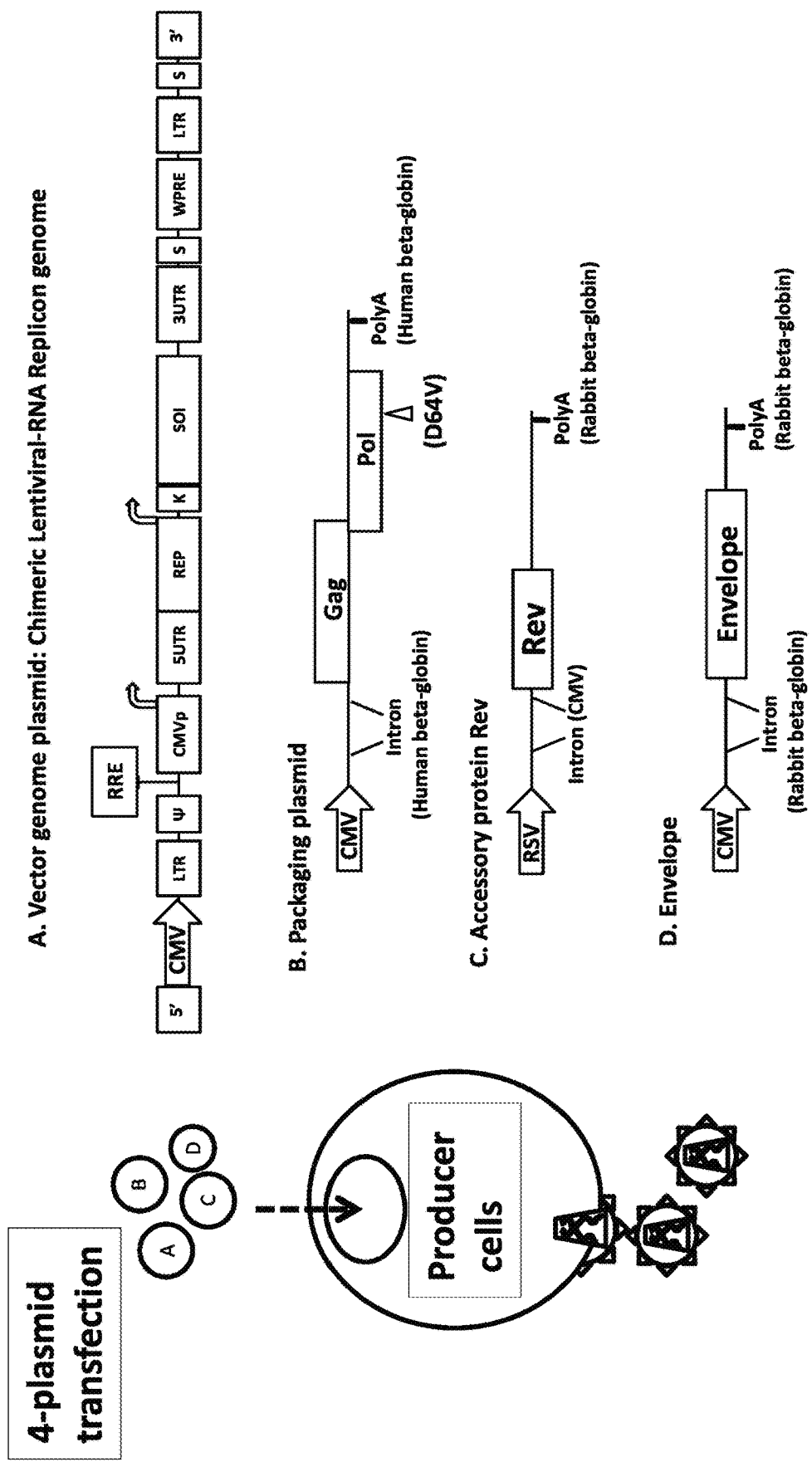
FIG. 3 is a schematic of an exemplary vector packaging system including illustrative vectors used in packaging chimeric lentiviral-RNA replicon vector particles.

Preparation of a Chimeric Lentiviral-RNA Replicon Vector Particle Comprising a Sindbis Virus E2 Envelope Glycoprotein Variant Using a packaging system similar to that outlined in FIG. 3, where the envelope protein was a modified Sindbis virus E2 envelope protein as described previously (see e.g. (*Molecular Therapy* vol. 22 no. 3, 575-587, 2014; U.S. Pat. No. 8,187,872), chimeric lentiviral-RNA replicon vector particles encoding the GFP reporter protein were produced in 293T producer cells expressing DC-SIGN. As shown in FIG. 6, the chimeric LV-replicon constructs were able to transduce 293T cells expressing DC-SIGN. Nevirapine only partially reduced LV-replicon transductions. As shown in FIG. 7, the GFP expression level (mean fluorescence intensity) in LV-replicon infected cells is about 10 to 50 fold higher than the mean fluorescence intensity of the parent lentiviral vector (Parent LV-704-GFP: see e.g., FIG. 2A; also as described in U.S. Pat. No. 8,187,872); 704-VEE-GFP-5'-3': the construct shown in FIG. 2B where the SOI is GFP; 704-VEE-GFP-3'-5': the construct shown in FIG. 2C where the SOI is GFP).

In a related experiment, chimeric lentiviral-RNA replicon vector was constructed expressing the NY-ESO-1 protein. Vector particles were produced as described above, cells were transduced, and transduced cell lysates run on SDS—PAGE and blotted for NY-ESO-1. The results showed that the LV-replicon constructs were able to produce NY-ESO-1 upon cell transduction. Protein levels were significantly higher than the level of protein produced by the parent lentiviral vector.

This Example confirms that the chimeric lentiviral-RNA replicon vector greatly improves expression of the sequence of interest from the chimeric vector genome when transduced into the host cells.

Example 3

Engineering of Functional RNA Replicon Vectors Containing RNA Packaging Signal This Example describes various strategies for engineering an alphavirus replicon-encoding sequence that has a HIV packaging signal to direct selective packaging of fully functional RNA replicon genomes.

As has been shown previously a semliki forest virus (US20080118956) or a sindbis virus replicon (US2015050243) can be passively encapsidated into a virus particle having a retroviral envelope even when the RNA sequence does not contain a specific packaging signal. It is generally understood that the inclusion of a packaging signal results in selective encapsidation of an RNA transcript and, thus, a larger number of produced virus particles containing the RNA of interest.

It is not obvious how an alphavirus replicon genome can be engineered to successfully contain a retro or lentiviral packaging signal. While sequences can readily be inserted downstream of the sequence of interest (SOI) but upstream of the 3' replication signal (see FIG. 8A), this results in an overwhelming encapsidation of the subgenomic RNA species, which is transcribed from the 26S promoter (indicated by the curved arrow in FIG. 8). The subgenomic RNA alone is not a functional replicon since it lacks the genes for the alphavirus nonstructural replicase proteins (REP in FIG. 8). Published US patent application US2008011895 describes a replicon with a genetically inactivated 26S promoter, which can be encapsidated into a retroviral particle without concomitant encapsidation of subgenomic RNA. However, this replicon would not be able to produce subgenomic transcripts in vector-transduced cells and, thus, would not mediate the same high SOI expression levels as a functional replicon that contains the 26S promoter. Moreover, this publication does not propose a solution for where a packaging signal can be inserted. Published US patent application US2015050243 mentions a plasmid that is engineered to have a packaging signal from Rous Sarcoma virus downstream of the eukaryotic CMV promoter but upstream of the replicon REP sequence. Note that since an intact 5' replication signal is required for alphavirus replicon replication, this construct would not result in a functional replicon. Indeed, the sequence included in the US2015050243 publication does not contain a packaging signal (even though the text refers to it as such).

FIG. 8B depicts an alphavirus replicon-encoding sequence that has a HIV packaging signal inserted downstream of the 5' replication signal. The replication signal spans across an untranslated region (5'UTR) and approximately 141 nucleotides into the translated region of the nsP1 gene of the replicase structural proteins (encoding the first 47 amino acids and encompassing the conserved sequence element). To allow for the translation of a functional replicase, a codon optimized sequence encoding these 47 amino acids is inserted in frame with the rest of the replicase-encoding gene, downstream of the inserted packaging signal, and preceded by an internal ribosome entry site (IRES). FIGS. 8B and 8C differ in their 3' ends with 8B containing a hepatitis delta virus ribozyme which acts to process the RNA transcripts to unit lengths in a self-cleavage reaction.

In another embodiment, translation of the replicase in achieved through a 2A endoprotease cleavage immediately at the beginning of the replicase (FIG. 8D). This requires translational read-through from the 5' end of the transcript, which is achieved by site-directed mutations that remove stop codons in the sequence upstream of the replicase gene. The constructs in FIGS. 8D and 8E differ in their 3' ends with the construct of 8D containing a hepatitis delta virus ribozyme which acts to process the RNA transcripts to unit lengths in a self-cleavage reaction.

In another embodiment the packaging signal is inserted in between the nsP3 and nsP4 genes. The alphavirus replicase is translated as an nsP1-3 polyprotein called P123. During normal translation, an arginine residue is incorporated at low frequency at the site of an opal stop codon, which thus results in translational read-through. This leads to a P1234 polyprotein, which subsequently is proteolytically cleaved at a site six amino acids downstream of the opal/arginine to produce mature nsP4 protein (see FIG. 8F). In the construct shown in FIG. 8G, a lentiviral packaging signal and an IRES sequence are inserted in between the nsP3 and nsP4 genes, flanked on both ends by a motif for proteolytic cleavage recognition. A similar approach has been described by Tamberg et al (J. Gen. Virol. 2007, doi:10.1099/vir.0.82436-0) for inserting a GFP gene in between nsP3 and nsP4 of Semliki Forest virus, albeit without the IRES. In a similar example shown in FIG. 8G, a short PSI mutated not to encode a stop codon is used by itself without an IRES but flanked on both ends by the proteolytic cleavage recognition motif.

Example 4

Evaluation of Transduction Efficiency Evaluation of Chimeric Lentiviral-Replicon Vector In Vivo This example describes the evaluation of the chimeric lentiviral-replicon vector systems in an in vivo murine model.

Female Balb/c mice were injected with the chimeric lentiviral-replicon vector constructs described in previous examples encoding for firefly luciferase.

The following vectors were tested in this experiment:

TABLE 1

| Prep Number | Prep | Genomes/mL | Particles/mL |
|---|---|---|---|
| 477 | 703 luc2 (integrating lentiviral vector as described in U.S. Pat. No. 8,187,872) | 2.78E+11 | ND |
| 478 | 704 luc2 (integration deficient lentiviral vector as described in U.S. Pat. No. 8,187,872) | 2.34E+11 | 6.5E+12 |
| 769 | FLUC (VEE 5-3) as shown in FIG. 2B | 3.39E+10 | 1.5E+12 |
| 770 | FLUC (VEE 3-5) as shown in FIG. 2C | 1.25E+11 | 3.0E+12 |
| 771 | RT independent construct as shown in FIG. 8E | NA | 4.4E-12 |
| 772 | RT independent construct as shown in FIG. 8D | NA | 3.2E-12 |

These injections were performed subcutaneously into their right footpads. The mice were then evaluated daily for luminescent signal at the site of injection using an IVIS Lumina system. These measurements were performed every 24 hours, including immediately after initial injection into the footpad. As shown in FIG. 9, all chimeric constructs successfully transduced murine cells at the site of injection and luciferase-specific luminescence was detected at least 4 days following initial immunization. The two RT independent constructs (#771 and #772) showed a high peak of expression at day 1 followed by decrease of expression out to day 4. Chimeric lentiviral-RNA replicon vectors (#769 and #770) also peaked at day 2. DC-targeting lentiviral vector as previously described (see e.g., U.S. Pat. No. 8,187,872) as expected showed an increase in transgene expression from days 1-4. Therefore, the present experiments confirm that the chimeric retroviral-RNA replicon vectors function in vivo to express high levels of the sequence of interest.

The various embodiments described above can be combined to provide further embodiments. All U.S. patents, U.S. patent application publications, U.S. patent application, foreign patents, foreign patent application, non-patent publications, protein and polynucleotide sequences referred to by accession numbers referred to in this specification and/or listed in the Application Data Sheet are incorporated herein by reference, in their entirety. Aspects of the embodiments can be modified if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

SEQUENCE LISTING

<160> NUMBER OF SEQ ID NOS: 4

<210> SEQ ID NO 1
<211> LENGTH: 8441
<212> TYPE: DNA
<213> ORGANISM: Alphavirus replicon
<220> FEATURE:
<221> NAME/KEY: 5'UTR

```
<222> LOCATION: (1)..(44)
<220> FEATURE:
<221> NAME/KEY: misc_feature
<222> LOCATION: (45)..(7523)
<223> OTHER INFORMATION: REP (nsP1-4)
<220> FEATURE:
<221> NAME/KEY: misc_feature
<222> LOCATION: (7574)..(8293)
<223> OTHER INFORMATION: SOI (i.e. GFP)
<220> FEATURE:
<221> NAME/KEY: 3'UTR
<222> LOCATION: (8325)..(8441)

<400> SEQUENCE: 1
```

| | | | | | |
|---|---|---|---|---|---|
| ataggcggcg | catgagagaa | gcccagacca | attacctacc | caaaatggag | aaagttcacg | 60 |
| ttgacatcga | ggaagacagc | ccattcctca | gagctttgca | gcggagcttc | ccgcagtttg | 120 |
| aggtagaagc | caagcaggtc | actgataatg | accatgctaa | tgccagagcg | ttttcgcatc | 180 |
| tggcttcaaa | actgatcgaa | acggaggtgg | acccatccga | cacgatcctt | gacattggaa | 240 |
| gtgcgcccgc | ccgcagaatg | tattctaagc | acaagtatca | ttgtatctgt | ccgatgagat | 300 |
| gtgcggaaga | tccggacaga | ttgtataagt | atgcaactaa | gctgaagaaa | aactgtaagg | 360 |
| aaataactga | taaggaattg | gacaagaaaa | tgaaggagct | ggccgccgtc | atgagcgacc | 420 |
| ctgacctgga | aactgagact | atgtgcctcc | acgacgacga | gtcgtgtcgc | tacgaagggc | 480 |
| aagtcgctgt | ttaccaggat | gtatacgcgg | ttgacggacc | gacaagtctc | tatcaccaag | 540 |
| ccaataaggg | agttagagtc | gcctactgga | taggctttga | caccaccccct | tttatgttta | 600 |
| agaacttggc | tggagcatat | ccatcatact | ctaccaactg | ggccgacgaa | accgtgttaa | 660 |
| cggctcgtaa | cataggccta | tgcagctctg | acgttatgga | gcggtcacgt | agagggatgt | 720 |
| ccattcttag | aaagaagtat | ttgaaaccat | ccaacaatgt | tctattctct | gttggctcga | 780 |
| ccatctacca | cgagaagagg | gacttactga | ggagctggca | cctgccgtct | gtatttcact | 840 |
| tacgtggcaa | gcaaaattac | acatgtcggt | gtgagactat | agttagttgc | gacgggtacg | 900 |
| tcgttaaaag | aatagctatc | agtccaggcc | tgtatgggaa | gccttcaggc | tatgctgcta | 960 |
| cgatgcaccg | cgagggattc | ttgtgctgca | aagtgacaga | cacattgaac | ggggagaggg | 1020 |
| tctcttttcc | cgtgtgcacg | tatgtgccag | ctacattgtg | tgaccaaatg | actggcatac | 1080 |
| tggcaacaga | tgtcagtgcg | gacgacgcgc | aaaaactgct | ggttgggctc | aaccagcgta | 1140 |
| tagtcgtcaa | cggtcgcacc | cagagaaaca | ccaataccat | gaaaaattac | cttttgcccg | 1200 |
| tagtggccca | ggcatttgct | aggtgggcaa | aggaatataa | ggaagatcaa | gaagatgaaa | 1260 |
| ggccactagg | actacgagat | agacagttag | tcatggggtg | ttgttgggct | tttagaaggc | 1320 |
| acaagataac | atctatttat | aagcgcccgg | atacccaaac | catcatcaaa | gtgaacagcg | 1380 |
| atttccactc | attcgtgctg | cccaggatag | cagtaacac | attggagatc | gggctgagaa | 1440 |
| caagaatcag | gaaaatgtta | gaggagcaca | aggagccgtc | acctctcatt | accgccgagg | 1500 |
| acgtacaaga | agctaagtgc | gcagccgatg | aggctaagga | ggtgcgtgaa | gccgaggagt | 1560 |
| tgcgcgcagc | tctaccacct | ttggcagctg | atgttgagga | gcccactctg | gaagccgatg | 1620 |
| tcgacttgat | gttacaagag | gctgggggccg | gctcagtgga | gacacctcgt | ggcttgataa | 1680 |
| aggttaccag | ctacgatggc | gaggacaaga | tcggctctta | cgctgtgctt | tctccgcagg | 1740 |
| ctgtactcaa | gagtgaaaaa | ttatcttgca | tccaccctct | cgctgaacaa | gtcatagtga | 1800 |
| taacacactc | tggccgaaaa | gggcgttatg | ccgtggaacc | ataccatggt | aaagtagtgg | 1860 |
| tgccagaggg | acatgcaata | cccgtccagg | actttcaagc | tctgagtgaa | agtgccacca | 1920 |

-continued

```
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccatagggtg tatggcgtg ccaggatcag     2220
gcaagtctgg catcattaaa agcgcagtca ccaaaaaaga tctagtggtg agcgccaaga    2280
aagaaaactg tgcagaaatt ataagggacg tcaagaaaat gaaagggctg acgtcaatg     2340
ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg ttttttaac atgatgtgcc      2520
tgaaagtgca ttttaaccac gagatttgca cacaagtctt ccacaaaagc atctctcgcc    2580
gttgcactaa atctgtgact tcggtcgtct caaccttgtt ttacgacaaa aaatgagaa     2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct ggagagacc ggaccctacc gacgtcttcc    3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctatttc tgcacccact gttccgttat ccattaggaa taatcactgg gataactccc    3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggaccc atataatac catcactatc     3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa gcttcgatt tacagccgat cgaagtagga aaagcgcgac    4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
```

```
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgc caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tccttttccat  4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga ccgatcatc atcgaagagg    5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aataggtga    5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca agctgcgca gctttccaaa gaaacactcc tatttggaac   6240
ccacaatacg atcggcagtg ccttcagcga tccagaacac gctccagaac gtcctggcag   6300
ctgccacaaa agaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
```

```
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg aatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatgcag    7140 acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga ccccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtccgccaa    7560
ggcgatcgcc accatggtga caagggcga ggagctgttc accggggtgg tgcccatcct    7620
ggtcgagctg gacggcgacg taaacggcca caagttcagc gtgtccggcg agggcgaggg    7680
cgatgccacc tacggcaagc tgaccctgaa gttcatctgc accaccggca agctgcccgt    7740
gccctggccc accctcgtga ccaccctgac ctacggcgtg cagtgcttca gccgctaccc    7800
cgaccacatg aagcagcacg acttcttcaa gtccgccatg cccgaaggct acgtccagga    7860
gcgcaccatc ttcttcaagg acgacggcaa ctacaagacc cgcgccgagg tgaagttcga    7920
gggcgacacc ctggtgaacc gcatcgagct gaagggcatc gacttcaagg aggacggcaa    7980
catcctgggg cacaagctgg agtacaacta caacagccac aacgtctata tcatggccga    8040
caagcagaag aacggcatca aggtgaactt caagatccgc cacaacatcg aggacggcag    8100
cgtgcagctc gccgaccact accagcagaa caccccatc ggcgacggcc ccgtgctgct    8160
gcccgacaac cactacctga gcacccagtc cgccctgagc aaagaccca acgagaagcg    8220 cgatcacatg gtcctgctgg agttcgtgac cgccgccggg atcactctcg gcatggacga    8280
gctgtacaag taaggcgcgc ctaagtaact aactgactga gtgaatacag cagcaattgg    8340
caagctgctt acatagaact cgcggcgatt ggcatgccgc cttaaaattt ttattttatt    8400
tttcttttct ttttccgaatc ggattttgtt tttaatattt c                      8441
```

<210> SEQ ID NO 2
<211> LENGTH: 1154
<212> TYPE: DNA
<213> ORGANISM: Alphavirus replicon
<220> FEATURE:
<221> NAME/KEY: 5'UTR
<222> LOCATION: (1)..(44)
<220> FEATURE:
<221> NAME/KEY: misc_feature
<222> LOCATION: (45)..(185)
<223> OTHER INFORMATION: Partial nsP1
<220> FEATURE:
<221> NAME/KEY: misc_feature
<222> LOCATION: (133)..(183)
<223> OTHER INFORMATION: 51NT conserved sequence domain
<220> FEATURE:
<221> NAME/KEY: misc_feature
<222> LOCATION: (186)..(425)

```
<223> OTHER INFORMATION: HIV core encapsidation sequence
<220> FEATURE:
<221> NAME/KEY: misc_feature
<222> LOCATION: (338)..(434)
<223> OTHER INFORMATION: HIV DIS
<220> FEATURE:
<221> NAME/KEY: misc_feature
<222> LOCATION: (393)..(406)
<223> OTHER INFORMATION: HIV PSI
<220> FEATURE:
<221> NAME/KEY: misc_feature
<222> LOCATION: (426)..(1013)
<223> OTHER INFORMATION: IRES of EMCV
<220> FEATURE:
<221> NAME/KEY: misc_feature
<222> LOCATION: (1014)..(1154)
<223> OTHER INFORMATION: nsP1 duplication (codon-modified)

<400> SEQUENCE: 2
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttgtgc ccgtctgttg tgtgactctg gtaactagag atccctcaga cccttttagt 240
cagtgtggaa aatctctagc agtggcgccc gaacagggac ttgaaagcga aagggaaacc 300
agaggagctc tctcgacgca ggactcggct tgctgaagcg cgcacggcaa gaggcgaggg 360
gcggcgactg gtgagtacgc caaaaatttt gactagcgga ggctagaagg agagagatgg 420
gtgcggcccc tctccctccc ccccccctaa cgttactggc cgaagccgct tggaataagg 480
ccggtgtgcg tttgtctata tgttattttc caccatattg ccgtcttttg gcaatgtgag 540
ggcccggaaa cctggccctg tcttcttgac gagcattcct aggggtcttt cccctctcgc 600
caaaggaatg caaggtctgt tgaatgtcgt gaaggaagca gttcctctgg aagcttcttg 660
aagacaaaca acgtctgtag cgaccctttg caggcagcgg aaccccccac ctggcgacag 720
gtgcctctgc ggccaaaagc cacgtgtata agatacacct gcaaaggcgg cacaacccca 780
gtgccacgtt gtgagttgga tagttgtgga aagagtcaaa tggctctcct caagcgtatt 840
caacaagggg ctgaaggatg cccagaaggt accccattgt atgggatctg atctggggcc 900
tcggtacaca tgctttacat gtgtttagtc gaggttaaaa aaacgtctag gccccccgaa 960
ccacggggac gtggttttcc tttgaaaaac acgatgataa tatggccaca accatggaaa 1020
aggtgcatgt ggatattgaa gaggattcac cttttctgcg ggccttgcaa cgctcttttc 1080
cccaattcga agtggaggct aaacaagtga ccgacaacga tcacgccaac gcacgcgcct 1140
tctcacacct cgcc 1154

<210> SEQ ID NO 3
<211> LENGTH: 621
<212> TYPE: DNA
<213> ORGANISM: Alphavirus replicon
<220> FEATURE:
<221> NAME/KEY: 5'UTR
<222> LOCATION: (1)..(44)
<220> FEATURE:
<221> NAME/KEY: misc_feature
<222> LOCATION: (45)..(185)
<223> OTHER INFORMATION: Partial nsP1
<220> FEATURE:
<221> NAME/KEY: misc_feature
<222> LOCATION: (133)..(183)
<223> OTHER INFORMATION: 51NT conserved sequence domain
<220> FEATURE:
<221> NAME/KEY: misc_feature
<222> LOCATION: (186)..(425)

```
<223> OTHER INFORMATION: HIV core encapsidation sequence
<220> FEATURE:
<221> NAME/KEY: misc_feature
<222> LOCATION: (338

VSVg, an alphavirus E2 glycoprotein, a retroviral envelope glycoprotein, or a targeting antibody.

6. The chimeric retroviral-RNA replicon vector particle claim 1, wherein the alphaviral replicon sequence of d) comprises the polynucleotide sequence set forth in SEQ ID NO:3.

7. The chimeric retroviral-RNA replicon vector particle of claim 1, wherein the SOI encodes a tumor associated antigen, a viral antigen, a bacterial antigen, or a fungal antigen.

8. The chimeric retroviral-RNA replicon vector particle of claim 1, wherein the retroviral vector is a lentiviral vector.

9. A pharmaceutical composition comprising the chimeric retroviral-RNA replicon vector particle of claim 1.

10. A method of inducing an immune response in a subject, comprising administering to the subject a pharmaceutical composition comprising the chimeric retroviral-RNA replicon vector particle of claim 7.

11. A method of treating cancer in a subject, comprising administering to the subject the pharmaceutical composition of claim 9, wherein the SOI encodes one or more tumor associated antigens and optionally one or more immune checkpoint inhibitors or one or more cytokines, or a combination thereof.

12. The method of claim 11, further comprising administering an additional therapeutic agent.

13. The method of claim 12, wherein the additional therapeutic agent is selected from the group consisting of a cytokine, an immune checkpoint inhibitor, a TLR agonist, a chemotherapeutic agent, and radiation.

14. A method of treating an infectious disease in a subject, comprising administering to the subject a pharmaceutical composition of claim 9 wherein the SOI encodes an antigen associated with the infectious disease.

15. A packaging system for producing a chimeric retroviral-RNA replicon vector particle, wherein the particle is reverse transcriptase independent, comprising a packaging cell transfected or otherwise modified to contain:

a) a first nucleic acid molecule encoding an envelope;
b) a second nucleic acid molecule encoding gag and pol proteins, wherein the second nucleic acid molecule optionally encodes a nonfunctional reverse transcriptase protein;
c) a third nucleic acid molecule comprising an alphaviral replicon sequence comprising in a 5' to 3' direction: i) a polynucleotide sequence comprising an alphavirus replication signal comprising at least a 5' untranslated region (5'UTR) and a first copy of a polynucleotide sequence comprising a portion of the nsP1 coding sequence which comprises at least a conserved sequence element (CSE); ii) a retroviral packaging sequence modified to contain no stop condons; iii) a polynucleotide sequence encoding a 2A endoprotease cleavage site; iv) a polynucleotide sequence encoding a full-length replicase polyprotein (REP) comprising a second copy of the nucleotide sequence comprising a portion of the nsP1 coding sequence comprising at least the CSE, wherein the second copy of the polynucleotide sequence is codon modified and in frame with the remainder of the sequence encoding the full-length REP; and v) a heterologous nucleic acid sequence of interest (SOI).

16. The packaging system of claim 15, wherein the envelope comprises a VSVg or an alphavirus E2 glycoprotein.

17. The packaging system of claim 15, wherein the retroviral vector comprises a 3' polypurine tract (PPT) which has been deleted or otherwise mutated to be nonfunctional.

18. The packaging system of claim 15, wherein the pol protein comprises a nonfunctional integrase.

19. A method of producing a chimeric retroviral-RNA replicon vector particle comprising culturing the packaging cell of claim 15.

20. A therapeutic or prophylactic vaccine comprising the chimeric retroviral-RNA replicon vector particle of claim 1 and a pharmaceutically acceptable excipient.

* * * * *

UNITED STATES PATENT AND TRADEMARK OFFICE
CERTIFICATE OF CORRECTION

| | |
|---|---|
| PATENT NO. | : 11,135,283 B2 |
| APPLICATION NO. | : 15/774465 |
| DATED | : October 5, 2021 |
| INVENTOR(S) | : Berglund et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 499 days.

Signed and Sealed this
Thirty-first Day of January, 2023

Katherine Kelly Vidal
*Director of the United States Patent and Trademark Office*